(12) United States Patent  
Selifonov et al.

(10) Patent No.: US 8,653,223 B2  
(45) Date of Patent: Feb. 18, 2014

(54) TRANSKETALIZED COMPOSITIONS, SYNTHESIS, AND APPLICATIONS

(75) Inventors: Sergey Selifonov, Plymouth, MN (US); Adam Edward Goetz, Los Angeles, CA (US); Feng Jing, Alpharetta, GA (US)

(73) Assignee: Segetis, Inc., Golden Valley, MN (US)

( * ) Notice: Subject to any disclaimer, the term of this patent is extended or adjusted under 35 U.S.C. 154(b) by 49 days.

(21) Appl. No.: 12/988,034

(22) PCT Filed: Apr. 16, 2009

(86) PCT No.: PCT/US2009/040841  
§ 371 (c)(1),  
(2), (4) Date: Dec. 6, 2010

(87) PCT Pub. No.: WO2009/146202  
PCT Pub. Date: Dec. 3, 2009

(65) Prior Publication Data  
US 2011/0082264 A1  Apr. 7, 2011

Related U.S. Application Data

(60) Provisional application No. 61/045,342, filed on Apr. 16, 2008.

(51) Int. Cl.  
*C07D 317/22* (2006.01)  
*C08G 16/00* (2006.01)  
*C08G 65/00* (2006.01)

(52) U.S. Cl.  
USPC ........... 528/220; 528/425; 528/486; 528/493; 549/267; 549/335; 549/341; 549/361; 549/448

(58) Field of Classification Search  
USPC .......... 528/220, 425, 486, 493; 549/267, 335, 549/341, 361, 448  
See application file for complete search history.

(56) References Cited

U.S. PATENT DOCUMENTS

| | | | |
|---|---|---|---|
| 3,183,215 A | 5/1965 | Pryde | |
| 3,223,683 A | 12/1965 | Pryde | |
| 5,998,092 A | 12/1999 | McCulloch et al. | |
| 6,528,025 B1 | 3/2003 | Boesch et al. | |
| 8,053,468 B2 * | 11/2011 | Selifonov | 514/467 |
| 2004/0024260 A1 | 2/2004 | Winkler et al. | |
| 2006/0069230 A1 | 3/2006 | Papisov | |
| 2007/0042936 A1 | 2/2007 | Bundle et al. | |
| 2008/0242721 A1 | 10/2008 | Selifonov | |

FOREIGN PATENT DOCUMENTS

| | | |
|---|---|---|
| CA | 2648012 A1 | 3/2009 |
| JP | 2004-217972 A | 8/2004 |
| SU | 722912 A1 | 3/1980 |
| WO | WO2009/032905 A1 | 3/2009 |
| WO | WO2009/048874 A1 | 4/2009 |
| WO | WO2009/049041 A2 | 4/2009 |

OTHER PUBLICATIONS

Ariza, X. et al., "New Protecting Groups for 1,2-Diols (Boc- and Moc-ethylidene). Cleavage of Acetals with Bases," Organic Letters, 2000, pp. 2809-2811, vol. 2, No. 18, American Chemical Society.

Bock, K. et al., "Acid Catalyzed Dehydration of Alditols. Part I. d-Glucitol and D-Mannitol," Acta Chemica Scandinavica, 1981, pp. 441-449, B 35, No. 6.

Carey, F. et al., "Advanced Organic Chemistry, Part B: Reactions and Synthesis, Second Edition," Chapter 11, 1983, pp. 539-552, Plenum Press, New York, NY USA.

Chirila, T., "Cicloacetal-esteri penta-si hexaatomici. Sinteza si caracterizarea unor 2-carboalcoximetil-1, 3-dioxolani (dioxani)," Revista De Chimie, 1977, pp. 730-733, vol. 28, No. 8, with English Abstract.

Criegee, R., "Mechanism of Ozonolysis," Angew. Chem Internat. Edt., 1975, pp. 745-751, vol. 14, No. 11.

Gelas, J. et al., "Recherches Dans la Serie Des Acetals Cycliques, XII*. Synthese du 4-oxo et de 4-Hydroxy-3,6,8-Trioxabicyclo[3.2.1]Octanes," Carbohydrate Research, 1973, pp. 21-34, vol. 30., Elsevier Scientific Publishing Company, Amsterdam, NL; No English Abstract Available.

International Search Report for PCT/US2009/040841 mailed Dec. 3, 2009, 5 pages.

Lichtenthaler, F., "Sugar-Derived Building Blocks for the Synthesis of Non-Carbohydrate Natural Products," Chapter 4 of Carbohydrate Synthons in Natural Products Chemisty, 2003, pp. 47-83, American Chemical Society, Washington D.C. USA.

Lukes, R., "Preparation of Methyl Esters Containing the 1,3-Dioxane or 2,4,8,10-Tetroxaspiro[5.5]undecane Structure by Ketal Exchange," Journal of Organic Chemistry, 1961, pp. 2515-2518, vol. 26, No. 7. Meltzer, R. et al., "2,2-Disubstituted 1,3-Dioxolanes and 2,2-Disubstituted 1,3-Dioxanes," Journal of Organic Chemistry, May 1960, pp. 712-715, vol. 25, No. 5).

Meskens, F., "Methods for the Preparation of Acetals* from Alchohols or Oxiranes and Carbonyl Compounds," Synthesis, Jul. 1981, pp. 501-522, No. 7, Georg Thieme Verlag, New York, NY USA.

Moncrieff, R.W., "Ketals," The Journal of the American Oil Chemists' Society, Aug. 1947, pp. 259-261.

Ono, D. et al., "Preparation, Surface-Active Properties and Acid Decomposition Profiles of a New "Soap" Bearing a 1,3-Diocolan Ring," JAOCS, Jan. 1993, pp. 29-36, vol. 70, No. 1, The American Oil Chemists' Society.

International Preliminary Report on Patentability and Written Opinion for PCT/US2009/040841, mailed Oct. 28, 2010, 10 pages.

* cited by examiner

*Primary Examiner* — Ana Woodward  
(74) *Attorney, Agent, or Firm* — Cantor Colburn LLP

(57) ABSTRACT

Ketal compounds of the structure I

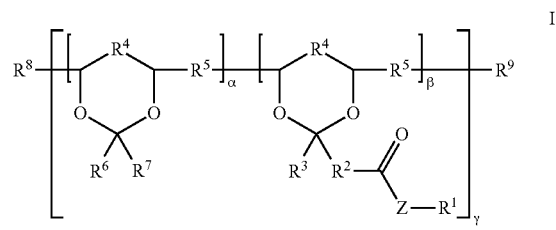

and a method of preparation of the compound from polyols and oxocarboxylates, as well as uses thereof.

7 Claims, 4 Drawing Sheets

TRANSKETALIZED COMPOSITIONS, SYNTHESIS, AND APPLICATIONS

This application is a National Stage filing of WO2009/146202, filed on 16 Apr. 2009, which claims the benefit of U.S. Provisional patent application Ser. No. 61/045,342 entitled "Ketal Diolide Compounds, Their Synthesis, and Applications", filed on Apr. 16, 2008, both of which are incorporated by reference in their entirety herein.

FIELD OF THE INVENTION

The invention relates to ketal compounds. The invention further relates to polymers and other compounds formed from the ketal compounds, and applications of the compounds in formulations or articles. The invention further relates to a method of forming the ketal compounds.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

It is desirable to provide commonly used materials, such as surfactants, plasticizers, solvents, and polymers, from renewable feedstocks as a source of chemical building blocks. It is desirable to provide chemical building blocks that are chemically and thermally stable. It is desirable to provide chemical building blocks having multiple functionalities for subsequent reactions. It is desirable to provide such materials by simple and reproducible methods that can be carried out with ease.

A potential source of materials that are useful as chemical building blocks are cyclic ketals and acetals of oxocarboxylates with polyols. It is known, for example, that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" $2^{nd}$ ed., 1983, Plenum Press, NY, N.Y., p. 544). The 1,2 and 1,3 configurations of hydroxyl groups on a hydrocarbon chain are shown below as (a) and (b), respectively.

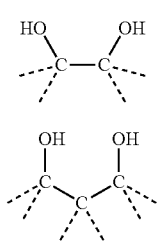

Diols such as 1,2-ethane diol (ethylene glycol) and 1,3 propanediol (propylene glycol) are examples of such polyols. Diols having a 1,2 hydroxyl group configuration form dioxolanes when reacted with ketone or aldehyde moieties, while 1,3 diols form dioxanes.

Various ketals arising from the reaction of oxocarboxylic acids and esters thereof with diols and triols are known. Ono et al., *J. Am. Oil Chem. Soc.* 70(1), 29 (1993) disclose ketalization of ethyl pyruvate, ethyl acetoacetate, and ethyl levulinate with various 1-O-alkyl glycerols (diols). Okohara et al., JP 04217972, similarly disclose ketalization of ethyl levulinate with 1-O-alkyl glycerols, followed by saponification of the ester moiety. McCullough et al., U.S. Pat. No. 5,998,092 disclose the ketalization of two keto acids with ethylene glycol. Chirila, *Revistade Chimie* 28(8), 730-3 (1977) discloses the 1:1 adduct of acetoacetate esters with glycerol. Gelas, *Carbohydrate Research* 30(1), 21-34 (1973) and Rakhmankulov et al., SU 722912 disclose the 1:1 adduct of pyruvate esters with glycerol and subsequent bicyclic lactone formation.

Ketals of glycerol and levulinic acid or an ester thereof are described in U.S. Patent Publication No. 2008/0242721, the entirety of which is incorporated herein by reference. The ketal reaction product of glycerol with a levulinate results in the ketal acid or ketal carboxylate shown below, along with one mole of water per mole of ketal formed:

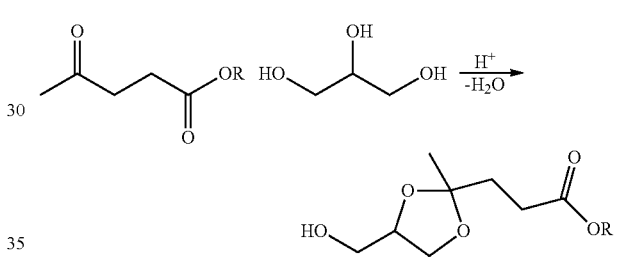

wherein R is hydrogen or an alkyl group. The use of levulinate compounds and glycerol based compounds is particularly useful as both of these starting materials arise from renewable feedstocks. Further, the ketal reaction products are useful for synthesis of a wide variety of surfactants, plasticizers, polymers, and the like. Other reaction products of oxocarboxylates (such as pyruvic acid, acetoacetic acid, or esters thereof, and the like) with triols (such as trimethylolpropane, trimethylolethane, and the like) are disclosed in International Patent Application No. PCT/U.S.08/75225. The methods employed to synthesize these compounds involve the formation of one mole of water with each mole of ketal formed. Likewise, polyketal compounds are formed from oxocarboxylates and tetrols and higher polyols using similar methods, with one mole of water formed for each mole of ketal functionality formed. Polyketal compounds are described in International Patent Application No. PCT/U.S.08/079,337. One example of a polyketal is a bisketal formed from a levulinate ester and erythritol (or a stereoisomer thereof):

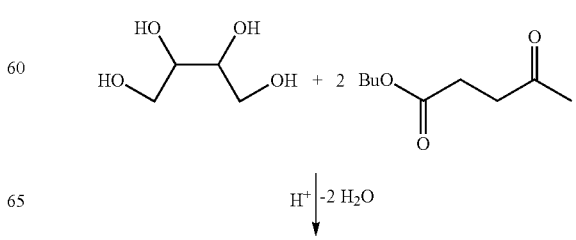

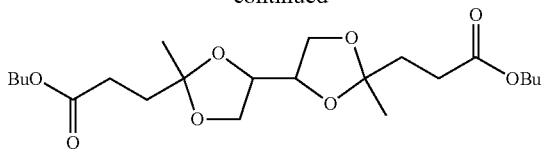

Other compounds formed from such reactions include the reaction product of three moles of a pyruvate ester (r=alkyl) with sorbitol or mannitol, to result in three moles of water and a trisketal:

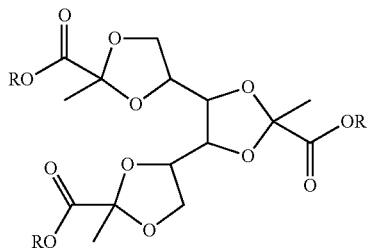

and the reaction of multiple moles of an acetoacetate ester (R=alkyl) with poly(vinyl alcohol) or an ethylene or propylene copolymer thereof, for example:

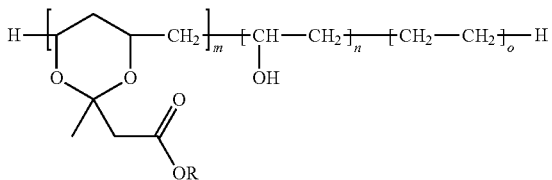

wherein m, n, and o are integers and o may be zero.

Synthetic routes to form ketals of oxocarboxylic acids or the esters thereof are described in International Patent Application No. PCT/U.S.08/079,083. The methodology disclosed therein employs very low levels of acid catalyst and certain stoichiometric ratios of oxocarboxylate to polyol to result in high yields of ketal compounds with short reaction times. However, this methodology, as well as previous methods used to form ketals from oxocarboxylates and polyols, necessarily involves the formation of water in conjunction with formation of the ketal end product. Because ketal formation is reversible in the presence of water and the acid catalyst, rigorous removal of water is necessary in order to drive the reaction and maintain high yields and product stability. Additionally, the main side products in the reaction of tetrols and higher polyols to form polyketals are typically those where less than the full desired complement of oxocarboxylate is reacted— e.g., a tetrol such as erythritol or diglycerol having one ketal functionality instead of two; or a hexitol such as mannitol having one or two ketal functionalities instead of three. Such side products are difficult to separate from the desired end product, necessitating fractionation. Further, the free hydroxyl groups present in these side products can undergo side reactions in subsequent polymerization reactions or create incompatibility with one or more formulation components in the application of bisketal and trisketal compounds as plasticizers, solvents, and the like.

Additionally, the structural variation of the ketal and polyketal compounds disclosed in the above cited patent applications and publications are limited to the variation in the polyol and oxocarboxylate compounds employed.

It is desirable to provide new starting materials and synthetic routes to form new varieties of chemical building blocks for monomers, plasticizers, surfactants, and polymers. It is desirable to provide chemical building blocks that arise solely from renewable feedstocks. It is desirable to facilitate synthesis of chemical building blocks that is simple, inexpensive, and scalable for commercialization purposes. It is desirable to avoid the problem of water formation in the ketalization of oxocarboxylic acids or their esters.

SUMMARY

Disclosed herein are compounds formed by the ketalization, transketalization, or partial transketalization of a polyol or alkyl ketal with an oxocarboxylic acid or an ester thereof. In embodiments, compounds of the invention are formed by first reacting a polyol, such as a tetrol or higher polyol having at least two hydroxyl pairs situated in 1, 2 or 1,3 configurations, with a two or more equivalents of a dialkyl ketone to give a fully ketalized polyol that is an alkylketal. The alkylketal is the reacted in a second step with one or more equivalents of an oxocarboxylic acid or ester thereof to displace some of the ketone equivalents and provide a partially transketalized ketal, or a hybrid ketal, having both alkyl ketal moieties and ketal carboxylate moieties. Alternatively, hybrid ketal compounds are formed by first reacting a polyol, such as a tetrol or higher polyol having at least two hydroxyl pairs situated in 1, 2 or 1,3 configurations, with one or more oxocarboxylic acids or esters thereof to give a ketal carboxylate. The ketal carboxylate is the reacted in a second step with one or more equivalents of a dialkyl ketone to displace some of the oxocarboxylate equivalents and provide the hybrid ketal. Which method is used depends on reaction conditions employed and the relative ease of removing either ketone vs. oxocarboxylate in the second step. In still other embodiments, the reaction of a polyol with a dialkyl ketone leads to novel alkylketal structures that in turn may be partially or completely transketalized to result in novel ketal structures.

The transketalized compounds offer a variety of advantages that could not previously be obtained in ketal structures. The combination of ketal moieties based on oxocarboxylate and dialkyl ketone in one molecule, for example, adds structural variation to the hybrid ketal compound, providing a combinatorial aspect to the synthesis and increasing the range of properties achievable by varying the ketone and oxocarboxylate structures. Additionally, the partially transketalized compounds offer differentiable functionality. For example, sorbitol—a hexitol—reacted with three equivalents of a ketone, then transketalized with two equivalents of oxocarboxylate, results in a trisketal dicarboxylate: three ketal functionalities and two carboxylate functionalities on a single molecule. Such a compound is suitable, for example, to make linear polyesters or polyamides. Alternatively, the same sorbitol-ketone precursor transketalized with one equivalent of an oxocarboxylate results in a trisketal monocarboxylate; such a compound is suitable, for example, as a surfactant or as a coalescing solvent. Further reactions of the monocarboxylate, such as saponification or reaction with a primary amine to form the corresponding amide, may be employed to enhance surfactant properties for one or more specific applications.

Also disclosed herein are the trisketals of sorbitol or mannitol and lower asymmetrical ketones. Lower asymmetrical ketones are those having different alkyl groups on either side of the oxo moiety and a total of less than 12 carbon atoms.

Examples of lower asymmetrical ketones include methyl ethyl ketone (MEK) and methyl isobutyl ketone (MIBK). The sorbitol and mannitol ketals of these compounds offer unexpected advantages in subsequent transketalization reactions with one or more oxocarboxylates when compared to sorbitol trisketals of symmetric ketones such as acetone, diethyl ketone, and the like.

Also disclosed herein is a method of making a partially or completely transketalized compound. In some embodiments, the method is used to make ketal compounds disclosed, for example, in International Patent Application No. PCT/U.S.08/079,337. This application is summarized above. However, the methodology of the synthesis offers advantages over the known art employed in the synthesis of ketals of oxocarboxylic acids and esters thereof.

Additional advantages and novel features of the invention will be set forth in part in the description that follows, and in part will become apparent upon examination of the following, or may be learned through routine experimentation upon practice of the invention.

DETAILED DESCRIPTION

Figure 1:
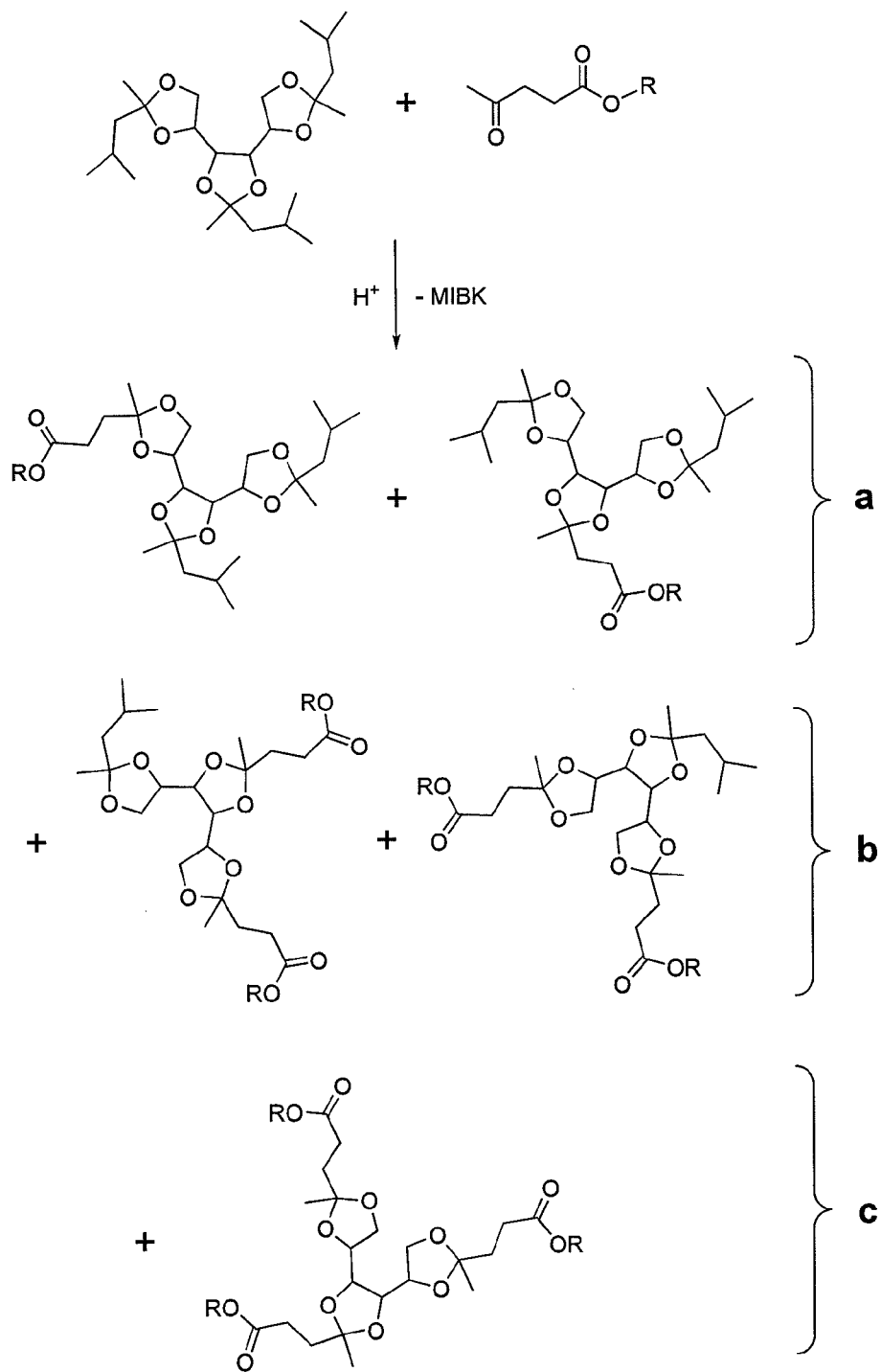
FIG. 1 shows one embodiment of a reaction of the invention.

Various embodiments will be described in detail. Reference to various embodiments does not limit the scope of the claims attached hereto. Additionally, any examples set forth in this specification are not intended to be limiting and merely set forth some of the many possible embodiments for the appended claims.

The compounds of the invention have, in embodiments, one or more isomers. Where an isomer can exist, it should be understood that the invention embodies all isomers thereof, including stereoisomers, conformational isomers, and cis, trans isomers; isolated isomers thereof; and mixtures thereof.

An embodiment of the invention is the class of compounds having structure

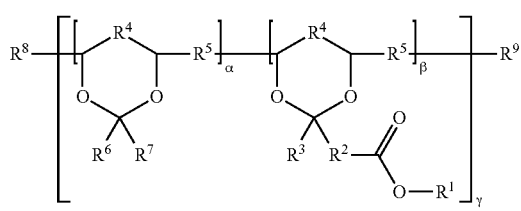

I wherein
$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$ is a covalent bond or a linear or branched alkyl group optionally containing one or more heteroatoms; and $R^2$ is the same or different for each occurrence;

$R^3$ is hydrogen, a linear, branched, or cyclic alkyl optionally containing one or more heteroatoms; and $R^3$ is the same or different for each occurrence;

$R^4$ is a covalent bond, methylene, or alkylmethylene, wherein a covalent bond indicates a 5-membered ring and a methylene or alkylmethylene indicates a 6-membered ring, and $R^4$ is the same or different for each occurrence;

$R^5$ is a covalent bond, methylene, ethylene, hydroxymethylene, oxygen, —$CH_2$—O—$CH_2$—, or a polymeric moiety, and $R^5$ is the same or different for each occurrence;

$R^6$ and $R^7$ are independently linear, branched, or cyclic alkyl groups;

$R^8$ and $R^9$ are independently hydrogen, a linear, branched, or cyclic alkyl, a linear, branched, or cyclic alkenyl, alkynyl, aryl, alkaryl, or a polymeric moiety and optionally contain one or more heteroatoms;

γ is an integer of at least 1; and

α and β are independently 0 or 1 for each γ.

Heteroatoms that are contained in one or more R groups of compounds I include, in some embodiments, O, N, S, Cl, Br, I, or. F; in some such embodiments, O may be contained as an oxo moiety. In embodiments where at least one α is 1 and at least one β is 1, the class of compounds I contemplates structures such as, for example,

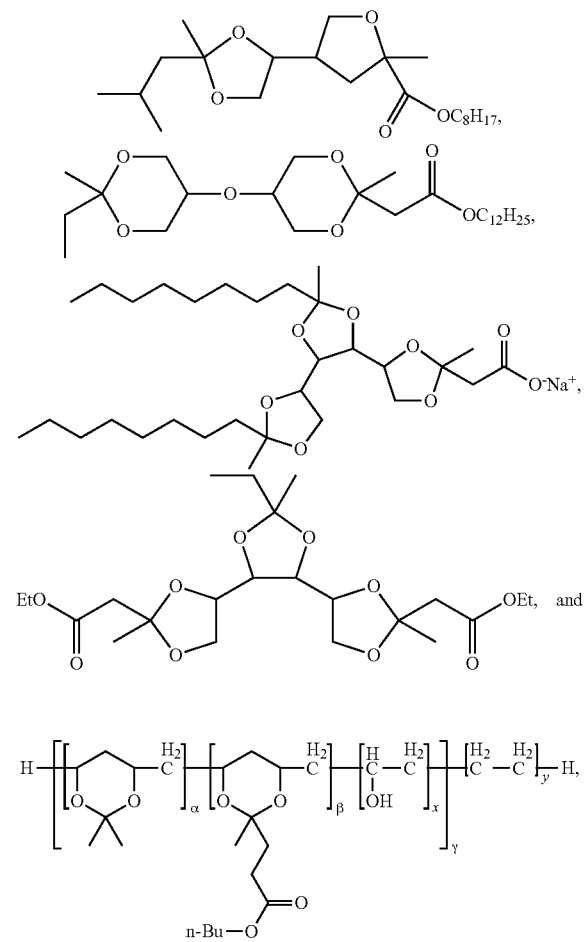

where α, β, and γ are as defined above, x is 0 or an integer, and y is an integer.

Another embodiment of the invention is the class of compounds having structure II:

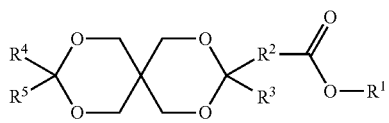

wherein
- $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms;
- $R^2$ is a covalent bond or a linear or branched alkyl group optionally containing one or more heteroatoms;
- $R^3$ is hydrogen, a linear, branched, or cyclic alkyl optionally containing one or more heteroatoms; and
- $R^4$ and $R^5$ are independently linear, branched, or cyclic alkyl groups.

Heteroatoms that are contained in one or more R groups of compounds II include, in some embodiments, O, N, S, Cl, Br, I, or. F; in some such embodiments, O may be contained as an oxo moiety. The class of compounds II contemplates structures such as, for example:

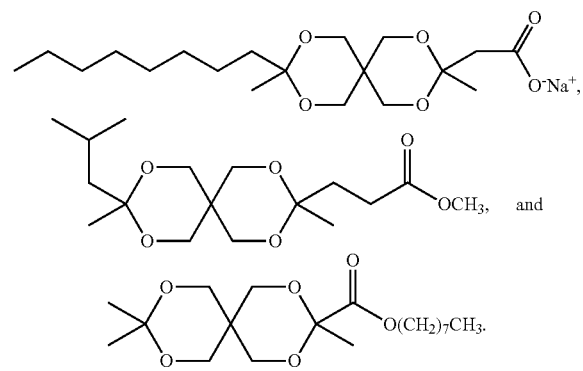

Compounds I and II are, in embodiments, formed in two steps.

Step 1—Alkylketal Formation

In embodiments, the first step of the reaction is reacting a dialkyl ketone with a tetrol or higher polyol, the polyol having at least two pairs of hydroxyl groups situated in a 1, 2 or 1,3 configuration. The 1,2 and 1,3 configurations of hydroxyl groups on a hydrocarbon chain are shown below as (a) and (b), respectively.

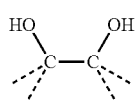

(a)

-continued

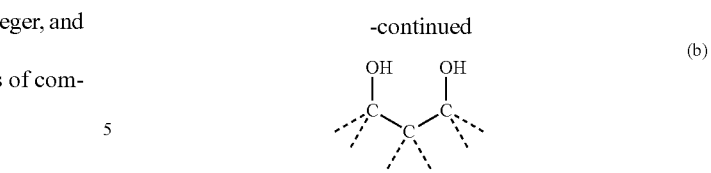

(b)

Configurations (a) and (b) facilitate formation, in embodiments, of ketals when reacted with a dialkyl ketone. Thus, the dialkyl ketone is reacted with a polyol in an amount corresponding to the number of moles of hydroxyl pairs of the polyol that have configurations (a) or (b) to result in an bisketal. For example, erythritol or pentaerythritol are reacted with two moles of acetone to give the corresponding bisacetonide. Similarly, mannitol or sorbitol is reacted with three moles of a dialkyl ketone, to form the corresponding trisketal. Higher polyols having additional hydroxyl pairs in configurations (a) or (b) are suitably reacted with additional molar equivalents of dialkyl ketones to form the corresponding polyketals.

Cyclic ketals formed from tetrols or higher polyols with dialkyl ketones are referred to herein as "alkylketals."

Polyols that are useful in the synthesis of alkylketals include those having at least two pairs of hydroxyl groups situated in a 1, 2 or 1,3 configuration. Examples of useful polyols include erythritol, threitol, pentaerythritol, diglycerol, xylitol, apiitol (2-hydroxymethyl erythritol), mannitol, sorbitol, maltitol, lactitol, dipentaerythritol, tripentaerythritol, and higher oligomers of pentaerythritol, raffinose, and stachyose; and poly(vinyl alcohol) and copolymers thereof, such as MOWITAL™ resin available from the Kuraray Company of Osaka, Japan; AQUASOL™ resin available from A. Schulman, Inc. of Akron, Ohio; or ELVANOL® resin available from the DuPont Company of Wilmington, Del. In some embodiments, the polyol employed is erythritol. In other embodiments, the polyol employed is sorbitol. In other embodiments, the polyol employed is diglycerol (a tetrol that is a mixture of glycerol dimers). As used herein, erythritol and threitol, which are diastereomers, are used interchangeably in various embodiments of the reaction. Similarly, sorbitol and its stereoisomer mannitol are used interchangeably in various embodiments. Where no stereochemistry is indicated in a chemical structure, any stereoisomer may be employed in the embodiments of the invention.

Ketones that are useful in forming the alkylketals are linear, branched, or cyclic dialkyl ketones. Examples of useful dialkyl ketones include propan-2-one (acetone), butan-2-one (methyl ethyl ketone, or MEK), 3-methylbutan-2-one, 3,3-dimethylbutan-2-one, pentan-2-one, pentan-3-one, 2-methylpentan-3-one, 2,4-dimethylpentan-3-one, 2,2-dimethylpentan-3-one, 2,2,4-trimethylpentan-3-one, 2,2,4,4-tetramethylpentan-3-one, 3-methylpentan-2-one, 4-methylpentan-2-one (methyl isobutyl ketone, or MIBK), 4,4-dimethylpentan-2-one, hexan-2-one, hexan-3-one, 5-methylhexan-2-one, 5-methylhexan-3-one, 2-methylhexan-3-one, 4-methylhexan-3-one, 2,2-dimethylhexan-3-one, 2,5-dimethylhexan-3-one, 2,2,5,5-tetramethylhexan-3-one, heptan-2-one, heptan-3-one, heptan-4-one, 5-methylheptan-3-one (ethyl amyl ketone), 6-methylheptan-3-one, 2-methylheptan-4-one, 2,6-dimethylheptan-4-one, octan-2-one, octan-3-one, octan-4-one, 2-methyloctan-3-one, nonan-2-one, nonan-3-one, nonan-4-one, nonan-5-one, 2-methylnonan-3-one, 2,6,8-trimethylnonan-4-one, decan-2-one, decan-3-one, decan-4-one, decan-5-one, undecan-2-one, undecan-3-one, undecan-4-one, undecan-5-one, undecan-6-one, 2-methylundecan-4-one, dodecan-2-one, dodecan-3- one, dodecan-4-one, hexadecane-10-one, and the like. Dialkyl ketones optionally contain one or more halogen atoms; thus, for example, 1-fluoropropan-2-one, 1,3-dichloropropan-2-one, 1-bromo-3,3-dimethylbutan-2-one, and 5-chloropentan-2-one are also useful ketones for forming the polyketal precursors of the invention.

In some embodiments, asymmetric ketones are employed in the formation of the alkylketals. Asymmetric ketones are those having two different alkyl groups attached to the oxo carbon. Examples of asymmetric ketones include MEK and MIBK. The alkylketals formed with asymmetric ketones are, in some embodiments, liquids at common room temperatures whereas the alkylketals formed from symmetrical ketones with the same polyol are crystalline solids with a tendency to sublime. For example, the MIBK trisketal of sorbitol is a liquid, while the acetone trisketal of sorbitol is a crystalline solid that is known to sublime under common use conditions. Sublimation is problematic for large scale industrial processes because material can be deposited within apparatuses, causing clogging and/or necessitating time consuming and difficult cleaning operations. In such embodiments, it is preferable to employ a ketone that is both asymmetric, thereby a non-subliming liquid at typical ambient temperatures, and low boiling enough to be efficiently collected in the transketalization step, when some ketone is replaced by oxocarboxylate. Accordingly, one embodiment of the invention is the class of compounds referred to herein as the asymmetric ketals of sorbitol or mannitol:

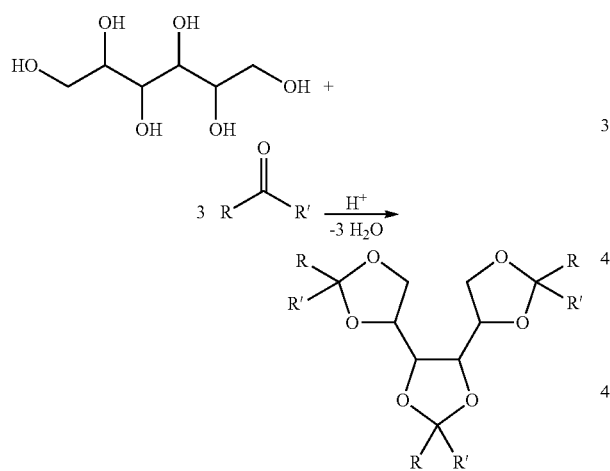

wherein R and R' are linear, branched, or cyclic alkyl groups that are not the same, and the sum of the number of carbon atoms in R and R' are less than 36. In such embodiments, MEK (R=—CH$_3$, R'=—CH$_2$—CH$_3$) and MIBK (R=—CH$_3$, R'=—CH$_2$CH(CH$_3$)$_2$) are both suitable asymmetric ketones. Because the trisketals of sorbitol with MEK or MIBK are liquids, they provide a surprising advantage in terms of ease of use in subsequent transketalization reactions.

The synthesis of the alkylketals may be carried out using any of the known techniques of forming cyclic ketals from dialkyl ketones and polyols. It is known, for example, that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" 2$^{nd}$ ed., © 1983, Plenum Press, NY, N.Y., p. 544). Exemplary techniques for the synthesis of cyclic ketals of polyols and ketones are described by Meltzer et al., *J. Org. Chem.,* 1960, 25 (5), pp 712-715; Lichtenthaler, F., ACS Symposium Series 841, 2003, 47-83; Moncrieff, R. W., J. Am. Oil Chem. Soc., 1947, 24(8), 259-61, and Meskens, F., Synthesis, 1981, 501-22. Industrial processes that are useful in forming the polyketal precursors are also described, for example, in Boesch et al., U.S. Pat. No. 6,528,025 and Winkler et al., US Patent Publication No. 2004/0024260. Synthetic methods for forming polyketal precursors from polymeric polyols are described in, for example, Papisov, U.S. Patent Publication No. 2006/0069230. The reaction is typically catalyzed by a strong protic acid, such as sulfuric acid, hydrochloric acid, toluenesulfonic acid, and the like. The synthesis of the alkylketals necessitates the evolution of water as an integral aspect of ketal formation. In all these syntheses, water must be removed from the reaction system in order to drive the ketalization to completion, because the reaction is reversible in the presence of the acid catalyst. Typical synthetic procedures employ a Dean Stark trap or a pervaporization membrane to facilitate separation of water from the reaction vessel as it is evolved.

In some embodiments, the ketone employed in making the alkylketals is known to form an azeotrope with water. In embodiments where such ketones are employed, use of a molar excess of the ketone in the first step of the reaction provides for ease of removal of the water that is a product of the ketalization of the polyol because the water can be removed as the azeotrope at elevated temperatures. After the azeotrope is collected, the ketone and water are, in embodiments, separated in order to recycle the ketone in the production of additional alkylketal. Such a method can, in embodiments, be employed in a continuous reaction process to form the alkylketals.

In an alternative first step, a polyol is ketalized with an acyclic or cyclic ketal of the ketone to yield the alkylketals. Thus, in a representative example, three moles of the bisacetonide of acetone, e.g. 2,2-dimethoxypropane, is reacted with one mole of D-sorbitol employing an acid catalyst:

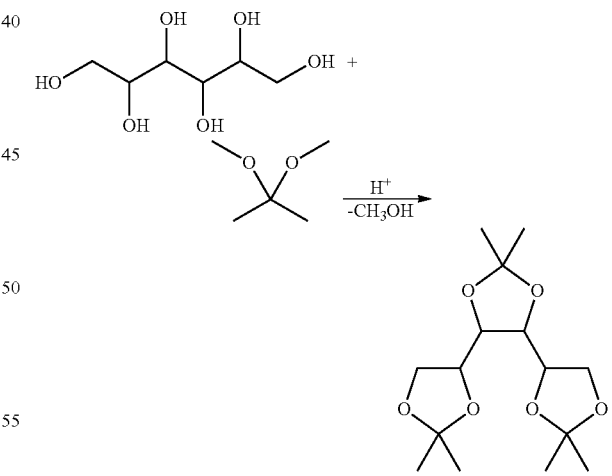

such that removal of methanol drives the transketalization to completion, resulting in the trisacetonide of sorbitol. Other similar examples will be readily envisioned.

Step 2—Transketalization

In embodiments, the second step of the reaction is the partial transketalization of the alkylketal with one or more molar equivalents of an oxocarboxylate to give the hybrid ketals of compounds I and II. An "oxocarboxylate" is defined as a keto acid, semialdehyde, or an ester or carboxylate salt thereof. Partial transketalization results in compounds I, having both alkylketal moieties and ketal carboxylate moieties, which are the α and β moieties of compound I, respectively; partial transketalization also results in compounds II with one alkylketal moiety and one ketal carboxylate moiety. As used herein, "ketal carboxylate" includes carboxylic ester, free carboxylic acid, and ionic carboxylate salt moieties; it further includes both ketal and acetal functionalities, wherein "ketal" is defined as a dioxolane or dioxane adduct of a ketone and "acetal" is defined as a dioxolane or dioxane adduct of an aldehyde. The compounds I and II having both one or more alkyl ketal moieties and one or more ketal carboxylate moieties may be referred to as "hybrid ketals" or "partially transketalized ketals."

Suitable oxocarboxylates that are used to form one or more hybrid ketals of the invention include keto acids, keto esters, semialdehydes, and semialdehyde esters. "Keto acid" refers to an oxocarboxylate having one or more ketone moiety and one or more carboxylate moiety. As used herein, "carboxylate" includes carboxylic acid, carboxylic ester, or carboxylic acid salt moieties. A compound may have more than one ketone functionality or more than one carboxylate functionality. The keto acid is not particularly limited as to additional moieties or functionalities present in addition to the ketone and carboxylate functionalities. In some embodiments, the compound may also contain one or more halogen, ester, amine, thiol, ether, phosphate, or silane groups. Some examples of suitable keto acids include pyruvic acid, acetoacetic acid, levulinic acid, 5-aminolevulinic acid, oxaloacetic acid, α-ketobutyric acid, α-ketoglutaric acid, α-ketoisovaleric acid, 5-ketohexanoic acid, α-ketoisocaproic acid, α-ketoadipic acid, 3-ketoadipic acid, 2-keto-4-methylthiobutyric acid, 4-acetylbutyric acid, 2-keto-3-bromobutyric acid, phenylpyruvic acid, 2-keto-3-phenylpropanoic acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, 13-keto-9,11-octadecadienoic acid, 4-ketostearic acid, 9-ketopalmitic acid, 4-ketoheptanedioic acid, pimelic acid, penicillic acid, 8-keto-8-aminopelargonic acid, 2-keto-5-aminovaleric acid, 2-succinylamino-6-oxoheptanedioic acid, 2-oxo-3-butynoate, 3-keto-6-acetamidohexanoate, and the like. Additionally, a keto acid may contain hydroxyl or mercapto functionality provided it is protected, e.g. by one or more trimethylsilyl or t-butyl groups, or one or more other protecting groups known to those of skill in the art.

In some embodiments of the invention, the keto acid employed is levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. In other embodiments, pyruvic acid and acetoacetic acid are other acids employed.

"Keto ester" refers to the carboxylic ester of the one or more carboxylate ester functionalities of any of the above described keto acid compounds. Thus, in embodiments of compound I, one or more $R_1$ is a linear, branched, or cyclic alkyl or alkenyl group having 1 to 18 carbon atoms, or an aryl or alkaryl group, wherein the alkyl, alkenyl, aryl, or alkaryl groups can have one or more additional functional groups that can include, for example, halogen, ester, amine, thiol, ether, or silane functionalities and are not particularly limited except that the one or more additional functional groups do not include hydroxyl or mercapto functionality. Thus, one or more $R_1$ is, in embodiments, methyl or ethyl; a linear or branched isomer of an alkyl group such as propyl, butyl, pentyl, hexyl, septyl, octyl, nonyl, decyl, undecyl, dodecyl, tetradecyl, cetyl, or stearyl; a cycloalkyl group such as cyclohexyl, cyclooctyl, norbornyl, and the like; an alkynyl group such as ethynyl, 3-methylpent-1-yn-3-yl, tetradec-9-yn-1-yl, and the like; an aryl and alkaryl group such as phenyl, benzyl, tolyl, xylyl, 5-phenylpent-1-yl, and the like; wherein the alkyl, alkenyl, alkynyl, aryl, or alkaryl may additionally have one or more functional groups, for example, 1,1,1-trichloro-2-methyl-2-propyl, 5-fluoro-1-pentyl, 5-amino-1-pentyl, 5-benzyloxy-1-pentyl, 5-methoxy-1-pentyl, 3-nitro-2-pentyl, 4-methylthio-1-butyl, 1-carboxyhex-6-yl, propionamid-2-yl, and the like. In some embodiments, $R_1$ contains a protecting group, such as trimethylsilyl, phosphonooxy, or a phosphatidyl group. The composition of the $R_1$ group is not particularly limited; however, if there are hydroxyl or thiol functionalities present on the $R_1$ group they should further be protected by a protecting group, such as trimethylsilyl, t-butyl, phosphonooxy, or another group generally known in the art to be a protecting group, to avoid side reactions of the free hydroxyl or thiol with a neighboring oxo group.

In some embodiments of the invention, esters of levulinic acid, pyruvic acid, or acetoacetic acid are employed as the keto esters in the polyols. For example, ethyl levulinate or n-butyl levulinate can be employed in some embodiments of the invention. Levulinic esters are based on levulinic acid, an abundant feedstock that is prepared on an industrial scale by acidic degradation of hexoses and hexose-containing polysaccharides such as cellulose, starch, sucrose, and the like.

"Semialdehyde" refers to an oxocarboxylate having one or more aldehyde functionalities and one or more carboxylate functionalities. The semialdehyde is not particularly limited as to additional moieties or functionalities present in addition to the aldehyde and carboxylic acid functionalities. In some embodiments, the semialdehyde may also contain one or more halogen, ester, phosphate, amine, thiol, ether, or silane groups. Some examples of suitable semialdehydes include aspartic semialdehyde, 4-oxobutanoic acid, 5-oxopentanoic acid, 6-oxohexanoic acid, 7-oxoheptanoic acid, α-formylglycine, 3-oxo-2-(phosphonooxy)-propanoic acid (tartronic semialdehyde wherein the hydroxyl group is protected by phosphate), 3-oxopropanoic acid (malonic semialdehyde), 2-methyl-3-oxopropanoic acid (methylmalonic semialdehyde), succinic semialdehyde, adipic semialdehyde, 5-glutamyl semialdehyde, allysine, 2-aminomuconic semialdehyde, 4-amino-5-oxopentanoic acid, N-acetylglutamic semialdehyde, 2-amino-3-(3-oxoprop-1-enyl)-but-2-enedioic acid, and N2-succinyl-L-glutamic-5-semialdehyde. Many other semialdehydes are available by carrying out ozonolysis of unsaturated fatty acid esters to form an aldehyde moiety at an unsaturated site, as described by Criegee, *Angew. Chem. Int. Ed.,* 1975, 87, 745.

"Semialdehyde ester" refers to the carboxylic ester of the one or more carboxylate functionalities of any of the above described semialdehyde compounds. The nature of the ester group is generally the same as those described above for the keto ester functionalities. The composition of the ester $R_1$ group, as shown in Reaction I, is not particularly limited; however, if there are hydroxyl or thiol functionalities present on the $R_1$ group they should further be protected by a protecting group, such as a trimethylsilyl group or another group generally known in the art to be a protecting group, to avoid side reactions of the free hydroxyl or thiol with a neighboring oxo group.

In embodiments, the hybrid ketals are formed from the corresponding alkylketals using an acid catalyst and a molar ratio of oxocarboxylate to alkylketal corresponding to about the number of moles of oxocarboxylate that are desired to replace alkyl ketal moieties with ketal carboxylate moieties. In some embodiments, the transketalization reaction is carried out neat; no additional solvents or other additives are required. The product ketone is simply separated from the reaction vessel, in embodiments by vaporization and collection by condensation, or by membrane separation, to drive the transketalization to the desired extent. Such methods are easily employed in continuous processes.

Other methods of transketalization have been employed; for example, transketalization of pentaerythritol is disclosed by Lukes, *J. Org. Chem.*, 1961, 26 (7), pp 2515-2518. Lukes employs the bisacetonide and a solution of an alkanol and a molar excess of two equivalents of oxocarboxylate ester to form the bisketal carboxylate of pentaerythritol. Pryde, U.S. Pat. Nos. 3,183,215 and 3,223,683 discloses ketal exchange of the dimethoxy ketal of azelaic semialdehyde with pentaerythritol. However, none of these methods are directed to partial transketalization and none of these methods result in a hybrid ketal.

We have found that transketalization is a desirable way to provide hybrid ketals of the invention. In embodiments, the ratio of oxocarboxylate employed per mole of transketalized moiety desired is about 10 to 1, in other embodiments about 6 to 1, in yet other embodiments less than 2. In embodiments, transketalization is carried out at elevated temperatures. In some such embodiments, the temperature employed to facilitate transketalization is about 20° C. to 200° C.; in other embodiments about 50° C. to 100° C. The transketalization employs, in embodiments, a strong protic acid catalyst. Strong protic acids (Brønsted-Lowry acids) are those that have a $K_a$ of 55 or greater. Examples of suitable strong protic acid catalysts include sulfuric acid, arylsulfonic acids and hydrates thereof such as p-toluenesulfonic acid monohydrate, perchloric acid, hydrobromic acid, and hydrochloric acid. In other embodiments, the acid catalysts employed in the method of the invention are weak protic acid catalysts. Weak protic acid catalysts are those having a $K_a$ of less than 55. Examples of suitable weak protic acid catalysts include phosphoric acid or orthophosphoric acid, polyphosphoric acid, and sulfamic acid. In some embodiments, more than one type of acid catalyst is used; thus, blends of one or more of the acids mentioned above may be used in a mixture to catalyze the reactions according to the method of the invention. In some embodiments, the acid catalyst is incorporated into, or onto, or covalently bound to, a solid support material. Resin beads, membranes, porous carbon particles, zeolite materials, and other solid support materials may be functionalized with acid moieties that are, in embodiments, covalently bound or strongly sorbed to one or more surfaces of the solid support. In a nonlimiting example, sulfonated resin is used in embodiments of the invention, which provide active sulfonic acid groups that are covalently bonded to the resin.

In embodiments, the acid catalyst is employed in the partial transketalization in amounts of about 10 ppm to 500 ppm based on total weight of all reagents; in some embodiments the catalyst is employed in amounts of about 50 ppm to 100 ppm based on the total weight of all reagents. In some embodiments, it is desirable to neutralize the acid catalyst after the transketalization reaction is complete. In these embodiments, the acid catalyst may be neutralized by addition to the reaction mixture of one or more metal oxides, metal hydroxides, or metal carbonates. Nonlimiting examples of such materials include basic aluminum oxide, magnesium oxide, sodium hydroxide, or sodium carbonate. In other embodiments the need to neutralize the acid catalyst is obviated either by the very low amounts of acid catalyst employed in the reaction, or the ability to use the acid catalyst in a subsequent reaction step such as polymerization, or by use of a catalyst that is covalently bound to a polymeric support and thus is separated from the reaction products by simple filtration.

In some embodiments, transketalization is carried out neat, without further addition of solvents. In other embodiments, a solvent is employed. The solvent may be inert, such as benzene, toluene, and the like; or the solvent may be reactive in the system, such as an alkanol or a ketone. In embodiments, transketalization is carried out at elevated temperatures in order to drive the removal of the ketone that is the reaction product of transketalization. In embodiments, reduced pressure is employed in the transketalization in order to drive the removal of the ketone that is the reaction product of transketalization. In some embodiments, the oxocarboxylate is employed in an amount corresponding to the stoichiometric number of transketalized groups desired, i.e. no excess oxocarboxylate is employed. In such embodiments, the temperature and pressure of the transketalization step is adjusted to maximize transketalization reaction and minimize loss of the oxocarboxylate by evaporation.

In embodiments, hybrid ketals of the invention are not purified after synthesis, e.g. where varying amounts of transketalized products arise, the products are, in embodiments, employed as a mixture. In other embodiments, the hybrid ketals of the invention are separated from the reaction mixture by fractional distillation. In other embodiments, techniques such as extraction, pervaporation, falling film evaporation, wiped film evaporation, membrane separation, or another conventional technique known in the art is employed to separate the product from one or more reaction mixtures.

Surprisingly, in some embodiments, the second step is selective for displacement, by oxocarboxylate, of certain alkyl ketal groups over others. This observed selectivity translates to higher yield of certain transketalized reaction products, rather than a simple statistical mixture of transketalized groups based on the ratio of oxocarboxylate to alkyl ketal moieties provided in the second step. This observed selectivity also imparts, in embodiments, ease of use in selecting amounts of reagents and reaction conditions, because a broader range of stoichiometries, reaction times, mode of addition of reagents, and so on may be employed. In embodiments, the observed selectivity is provided the choice of reagents. For example, in the synthesis of the hybrid ketal of sorbitol or mannitol, we have found that employing the MIBK trisketonide of sorbitol imparts selectivity for the two end pairs of hydroxyl to undergo subsequent transketalization with an oxocarboxylate. Referring to FIG. 1, stereoisomers aside, a range of transketalization conditions results in ratios of products a, b, and c such that the amount of c products is, in embodiments, about 20 wt % to 1 wt %, or about 10 wt % to 5 wt %.

In some embodiments, it is desirable to employ the methodologies above to bring about complete transketalization of all alkyl ketal groups to form only ketal carboxylate groups. Thus, in some embodiments, erythritol is functionalized with two equivalents of a dialkyl ketone, then the dialkyl ketone is transketalized with two equivalents of an oxocarboxylate. Bisketal carboxylates of erythritol are disclosed in International Patent Application No. PCT/U.S.08/79337. Employing transketalization methodology instead of direct ketalization to form these bisketal carboxylates, and other ketal carboxylates such as any of those described in International Patent Application No. PCT/U.S.08/79337, provides one or more advantages in the final product. Most notably, we have observed that using transketalization methodology results in lower residual hydroxyl functionality, as described above, in the final product ketal. This in turn translates to higher yield of the desired end product and in some cases obviates the need for purification steps such as fractional distillation. Additionally, employing transketalization methodology obviates the need to remove water from the reaction vessel in order to drive the reaction to the desired end product. Rather, a dialkyl ketone is collected and can be recycled in the first step (ketalization of polyol with dialkyl ketone). This advantage lends itself readily to efficient continuous processes.

Steps 1 and 2

Alternative embodiments

In some embodiments, hybrid ketals are formed by first reacting an oxocarboxylate with a tetrol or higher polyol, the polyol having at least two pairs of hydroxyl groups situated in a 1, 2 or 1,3 configuration, to result in a ketal carboxylate; the polyketal carboxylate is then reacted with one or more equivalents of a dialkyl ketone to form the hybrid ketal. Polyketal carboxylates, and the method of making them, are disclosed in International Patent Application No. PCT/U.S.08/79337. The second step forming the hybrid ketal is accomplished using standard methods as disclosed above for synthesis of alkylketals, except that stoichiometry should be adjusted, in the present case, to facilitate partial transketalization. The types of polyols, dialkyl ketones, oxocarboxylates, and catalysts employed in the presently described embodiment are the same as those disclosed above.

It will be understood that the choice of whether to make the alkylketal in the first step, followed by partial exchange with an oxocarboxylate in the second step, or to make the ketal carboxylate in the first step, followed by partial exchange with a dialkyl ketone in the second step, will depend on the choice of ketone and oxocarboxylate. For the purposes of understanding how the choice of ketone and oxocarboxylate affect the method employed to make the hybrid ketals of the invention without limiting the method or compounds formed, a "first reagent" is reacted with the polyol in the first step forms an "intermediate ketal" (alkylketal or ketal carboxylate). The compound used to displace the first reagent by transketalization in the second step is the "second reagent." Of the two reagents, the reagent with the lower boiling point is, in embodiments, advantageously used as the first reagent. This is because in the second step, some or all equivalents of the first reagent must be removed from the reaction vessel or system in order to drive the transketalization with the second reagent to result in the final product ketal. Since many conventional methods employ evaporation of the first reagent, it is preferable that the first reagent has a lower boiling point than the second reagent in order to facilitate ease of removal of the first reagent without concomitant loss of the second reagent.

In yet another embodiment of the invention, synthesis of the MIBK ketal of sorbitol results in the formation of an amount of cyclic ether bis-MIBK ketals

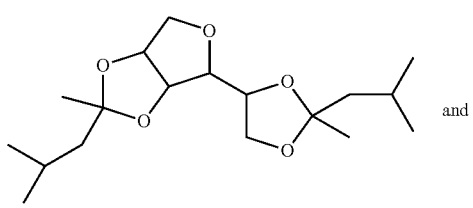
and

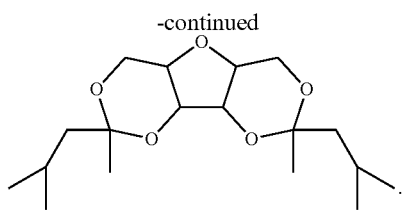

The bis-MIBK ketals form when the rate of cyclic ether formation is competitive with the rate of ketalization. The former compound is the result of condensation at the 1,4 position of sorbitol, followed by ketalization with MIBK; the latter compound is the result of condensation at the 2,5 position of sorbitol, followed by ketalization with MIBK:

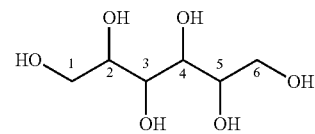

Without wishing to be limited by any theory, we believe that the cyclic ether formation is kinetically favored over ketalization with MIBK at the reaction temperature employed, and that cyclic ether formation is kinetically favored in sorbitol vs. its stereoisomer, mannitol. The latter theory is consistent with Bock et al., *Acta Chemica Scandinavica* 1981, B 35, 441-9. Also consistent with Bock et al. is that 1,4 condensation and 2,5 condensation of sorbitol are competitive with each other, such that both products are expected where one such product is encountered. The compounds are, in various embodiments, subsequently employed in one or more reactions as a blend; in other embodiments the compounds are separated before one or more subsequent reactions; in still other embodiments the compounds are employed in one or more reactions as a blend and then subsequently separated. The means of separating the compounds are, in general, any of those conventional means employed in the industry; for example, fractional distillation, reactive distillation, chromatographic separation, pervaporization, falling film evaporation, or wiped film evaporation.

In embodiments, the cyclic ether bis-MIBK ketals are readily transketalized, using the techniques described above, with one or two equivalents of an oxocarboxylate to result in the corresponding compounds IIIa and IIIb:

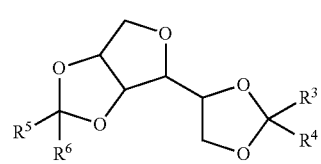

IIIa

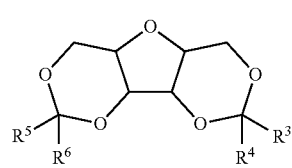

IIIb wherein for both IIIa and IIIb
$R^3$ and $R^5$ are independently isobutyl or

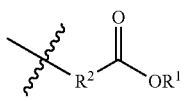

wherein $R^2$ is a covalent bond or a linear or branched alkyl group and optionally contains one or more heteroatoms, and $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety and optionally contains one or more heteroatoms; and $R^4$ and $R^6$ are independently hydrogen or linear, branched, or cyclic alkyl and optionally contain one or more heteroatoms.

Heteroatoms that are contained in one or more R groups of compounds I include, in some embodiments, O, N, S, Cl, Br, I, or. F; in some such embodiments, O may be contained as an oxo moiety. Compounds IIIa and IIIb are, in various embodiments, bisalkylketals of MIBK, hybrid ketals of MIBK and oxocarboxylate, or bisketal carboxylates. For the purposes of the discussion below, compounds IIIa and IIIb are collectively referred to as "compounds III."

The compounds I, II, and III of the invention have many unexpected and advantageous features that are, in various embodiments, exploited to produce monomers, polymers and copolymers, surfactants, plasticizers, and solvents for various useful industrial applications. Various embodiments described below include the synthesis of compounds I, II, and III; applications of compounds I, II, and III; subsequent reactions of compounds I, II, and III to form additional useful species; and applications of those species.

Embodiments of Compounds I and III

In embodiments, compounds I and III are useful as, or to make, one or more surfactants, solvents, stabilizers, plasticizers. In embodiments, compounds I are useful as, or to make, one or more monomers. The monomers are, in embodiments, useful to make one or more linear, branched, or crosslinked polymeric compounds. The reaction to form compound I is represented as:

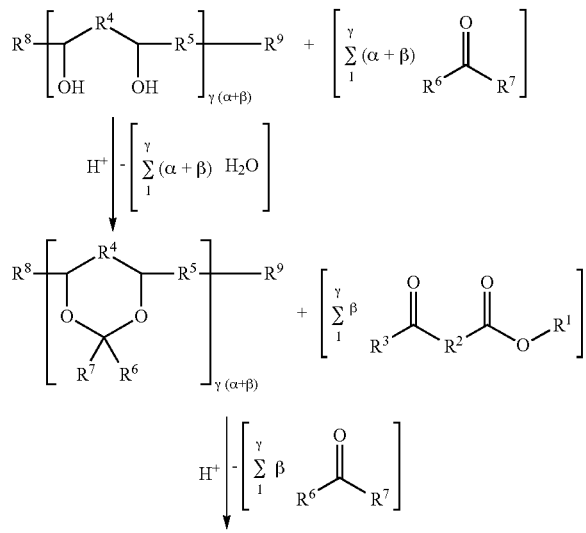

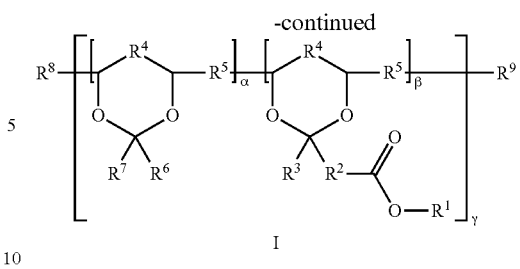

I wherein $R^1$, $R^2$, $R^3$, $R^4$, $R^5$, $R^6$, $R^7$, $R^8$, $R^9$, $\alpha$, $\beta$, and $\gamma$ are as defined above. The reactions of compounds III are analogous to the above reaction scheme. In some alternative embodiments of the reaction to form compounds I and III, an acyclic ketal of the ketone $R^6R^7C=O$ may be used in the first step of the reaction. For example, where the ketone to be employed in the first step is acetone, 2,2-dimethoxypropane may be used in its place. In such embodiments, methanol is displaced instead of water. In some such embodiments, the ease of removing of methanol is advantageous; this is particularly true where large scale reaction processes are employed, as the use of an acyclic ketal as a starting material instead of a ketone ameliorates the problem of removing water and issues with residual water in the system. In other embodiments, it is advantageous to use the ketone and displace water, as water need not be stored or disposed of, and is not flammable or combustible.

In embodiments of compound I, the total number of alkyl ketal and ketal carboxylate moieties in the hybrid ketals of compound I is determined by the values of $\alpha$, $\beta$, and $\gamma$. The sum from 1 to $\gamma$ of all $\alpha$ is at least 1, and the sum from 1 to of all $\beta$ is at least one. Thus, a bisketal having one alkyl ketal moiety and one ketal carboxylate moiety is the simplest form of compound I. These embodiments, and many others, are described below in greater detail.

In embodiments of compounds III, the total number of ketal moieties is 2, and the ketals are alkyl ketals, ketal carboxylates, or one each of an alkyl ketal and a ketal carboxylate—e.g. a hybrid ketal. It will be understood that for embodiments of compounds III that are hybrid ketals, the applications and reactions thereof are analogous to those of compounds I wherein the total sum of all $\beta$ is 1. Similarly, for embodiments of compounds III that contain 2 ketal carboxylates, the applications and reactions thereof are analogous to those of compounds I wherein the total sum of all $\beta$ is 2.

Hybrid ketals I wherein $\gamma$ is at least 2 and the sum of all $\beta$ is 2, or wherein the average sum of all $\beta$ is about 2, comprise a combinatorial group of dicarboxylate compounds that are, in embodiments, employed in the formation of cyclic or polymeric compounds. These embodiments are described in detail below in greater detail, in the sections entitled "Cyclic Polyketal Compounds" and "Oligomers and Polymers of Structures I and III."

Salts, Esters, and Amides of Compounds I

Salts.

In embodiments of compound I, one or more $R^1$ is a cation, for example a sodium, lithium, ammonium, or alkylammonium cation. In such embodiments compound I is a surfactant or an additive for one or more aqueous formulations. Cation functionality is typically imparted to the compounds I after the second step of the synthesis, employing standard saponification methods widely employed in the industry and readily found in the literature. Examples of such embodiments include the following compounds:

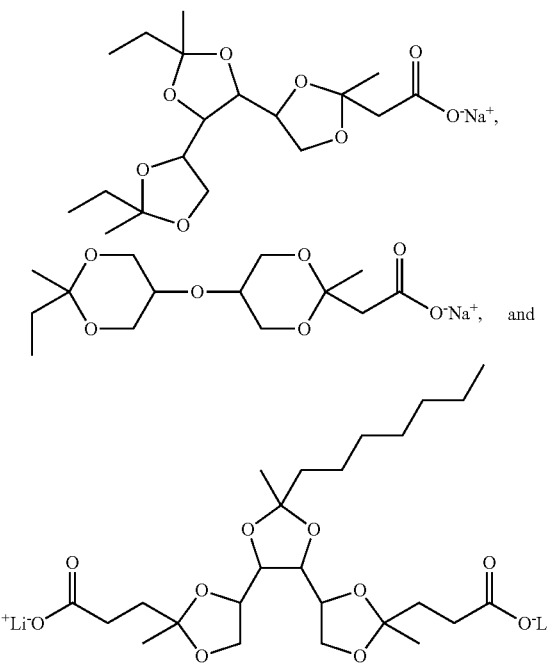

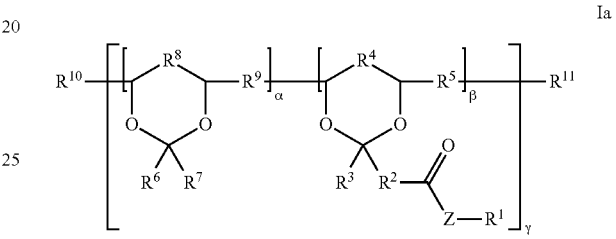

In some embodiments, divalent or polyvalent cations are employed. Divalent or polyvalent cations, for example calcium, barium, or magnesium cations, are also used, in some embodiments, to functionalize compounds I to give ionic dimer or oligomer species. In one or more embodiments, ionic dimers or oligomers are stabilizers for one or more polymeric compositions that are subjected to high temperatures, such as are encountered in thermal processing.

In some embodiments of compound I, the sum γ of all α and β is 3 or less and one or more $R^1$ is an alkyl group having less than six carbon atoms. In one or more such embodiments compounds I are solvents, for example coalescing solvents for polymeric dispersions, emulsions, or plastisols; or solvents for one or more organic compounds; or solvents for removal of compounds and coating formulations from surfaces, e.g. paint, varnish, and the like. In other embodiments of compound I, the sum γ of all α and β is 3 or less and one or more $R^1$ is an alkyl group having six or more carbon atoms. In one or more such embodiments compounds I are plasticizers, for example, in one or more polymer formulations or plastisols. In some such embodiments, $R^1$ functionality is imparted by carrying out transesterification of compounds I, employing any of the conventional techniques in the literature. Such reactions are useful, in embodiments, to transform an ester group having less than six carbons to an ester group having six or more carbons.

In other embodiments of compound I, the sum γ of all α and β is 3 or less and one or more $R^3$, $R^4$, $R^5$, or a combination thereof are alkyl groups having less than six carbons. In one or more such embodiments compounds I are solvents, for example coalescing solvents for polymeric dispersions, emulsions, or plastisols; or solvents for one or more organic compounds; or solvents for removal of compounds from surfaces e.g. paint, varnish, and the like. In other embodiments of compound I, the sum γ of all α and β is 3 or less and one or more $R^3$, $R^4$, $R^5$, or a combination thereof are alkyl groups having more than six carbons. In one or more such embodiments compounds I are plasticizers, for example, in one or more polymer formulations or plastisols.

In other embodiments of compound I, varying the nature of the oxocarboxylate employed leads to variations in resulting properties, where the sum γ of all α and β is 3 or less, thereby varying one or more equivalents of $R^2$ and $R^3$. Thus, by varying the oxocarboxylate of the hybrid ketal, solubility, boiling point, and hydrophobicity are, in embodiments, varied for one or more applications of compounds I as surfactants as described above.

Amides.

Compounds I are employed, in embodiments, in a subsequent reaction to form one or more amide functional compounds. Reaction of one or more ketal carboxylate moieties of compounds I with primary or secondary amines results in displacement of at least one ester moiety to form the corresponding ketal amide moiety. In such embodiments, compound I is transformed to compound Ia:

wherein $R^1$-$R^{11}$, α, β, and γ are as previously defined for compound I, and each Z is independently O or NR provided that at least one Z is NR, wherein R is hydrogen or an alkyl group having six or less carbons and can optionally contain one or more heteroatoms.

Any of the conventional techniques known in the art to form amides from esters or free acids may be employed in the synthesis of amides Ia from the corresponding esters or free acids of compounds I. Suitable amines that are useful in forming the amides Ia include, for example, ethylamine, linear and branched isomers, including primary and secondary amino adducts, of propylamine, butylamine, pentanamine, hexylamine, heptylamine, octylamine, nonylamine, decylamine, undecylamine, dodecylamine, or higher alkylamines; N-methylethanamine, 2-methoxyethanamine, 2-(ethylamino)ethanol, N-ethyl-2-(3H-inden-1-yl)ethanamine, 2,2,2-trifluoroethanamine, histamine, tryptamine, 2-cyclohexen-1-ylethanamine, N,N-diethylethane-1,2-diamine, 2-(2-adamantyl)ethanamine, 2-methylsulfanylethanamine, 2-thiophen-2-ylethanamine, 2-(4-methylpiperazin-1-yl)ethanamine, 2-(3,4-dimethoxyphenyl)ethanamine, 1-naphthalen-1-ylethanamine, N-ethyl-1-phenylcyclohexan-1-amine, 2-(4-chlorophenyl)ethanamine, 1-(4-methylphenyl)ethanamine, 2-trimethylsilyloxyethanamine, N-(phenylmethyl)ethanamine, 2-pyridin-2-ylethanamine, prop-2-en-1-amine, pent-4-yn-1-amine, N,N-dimethylbut-1-en-3-yn-1-amine, N-prop-2-ynylprop-2-yn-1-amine, and the like.

In embodiments where the sum of all β is 3 or less, amides Ia are useful as surfactants in one or more applications. In some such embodiments, the amine employed to form the amide is a primary amine having six or less carbons. In some such embodiments, the amine employed contains hydroxyl or other heteroatomic moiety. Suitable examples include ethanolamine and diethanolamine. In embodiments where the sum of all β is 1 and the amine employed is a diamine, the amide reaction forms dimers of compound Ia; in embodiments where the sum of all β is 1 and the amine employed is a triamine, the amide reaction forms trimers of compound Ia. Similar variations are easily envisioned.

In other embodiments of compound Ia, varying the nature of the oxocarboxylate employed leads to variations in resulting properties, where the sum γ of all α and β is 3 or less, thereby varying one or more equivalents of $R^2$ and $R^3$. Thus, by varying the oxocarboxylate of the hybrid ketal, solubility, boiling point, and hydrophobicity are, in embodiments, varied for one or more applications of compounds I as surfactants and the like as described above.

Esters.

In embodiments, compounds I are useful in ester form as, for example, plasticizers, solvents, and the like. The hydrophobic/lipophobic character of compounds I are easily tailored by choice of ketone, polyol, oxocarboxylate, and other reagents selected in conjunction with the above described variety of subsequent reactions, rendering the resulting compounds I, as well as Ia, compatible with a broad range of formulations either as a major component or a minor component or rendering them suitable for one or more other applications, for example use as a plasticizer or a solvent. Further, the combinatorial compositions chosen are achieved with ease employing simple, straightforward chemical transformations using standard laboratory equipment. The amount of free hydroxyl measured for the reaction products of the invention is, in some embodiments, lower than the amount of free hydroxyl functionality measured for the corresponding polyketal based on the direct reaction of two moles of oxocarboxylate with tetrols such as erythritol or three moles of oxocarboxylate with a hexitol such as sorbitol.

As such, compounds I are advantageously employed as plasticizers. Plasticizers are chemical compounds added to a base composition comprising one or more of the above polymers with the purpose of lowering the glass transition temperature of the polymer composition, thereby making the composition more flexible and amenable to processing, e.g., by melt extrusion or molding. Plasticizers can also confer other changes in physical and mechanical properties of the compounded polymer, as well as changes in barrier properties of the compounded polymer in respect to its permeability for various gases, water, water vapor, or organic compounds. Compounds I with substantially no free hydroxyl groups, are widely compatible with many commercially useful polymers and the formulations and articles employing them.

Thus, the compounds I are suitably employed as plasticizers with polymers such as, for example, poly(vinyl chloride) or PVC; polyesters such as polyethylene terephthalate (PET) and polybutylene terephthalate (PBT); aliphatic/aromatic copolyesters, as for example polybutylene terephthalate adipate (PBTA), polybutylene terephthalate succinate (PBTS), and polybutylene terephthalate glutarate (PBTG); biodegradable polyesters such as polylactic acid; poly-6-caprolactone; polyhydroxybutyrates such as poly-3-hydroxybutyrates, poly-4-hydroxybutyrates and polyhydroxybutyrate-valerate, polyhydroxybutyrate-propanoate, polyhydroxybutyrate-hexanoate, polyhydroxybutyrate-decanoate, polyhydroxybutyrate-dodecanoate, polyhydroxy-butyrate-hexadecanoate, polyhydroxybutyrate-octadecanoate, and polyalkylene succinates and their copolymers with adipic acid, lactic acid or lactide and caprolactone and their combinations, and the like; polystyrene and copolymers thereof; polyurethanes; polycarbonates; polyamides such as Nylon 6 and Nylon 6,6; polyolefins such as polyethylene, polypropylene, and copolymers thereof; and other industrially useful polymeric compounds. Such polymers also include polymer compositions which are blends of any of the above polymers, for example, composites with gelatinized, destructed and/or complexed starch, natural starch, flours, and other materials of natural, vegetable or inorganic origin. Polymer compositions include, in some embodiments, polymers of natural origin, such as starch, cellulose, chitosan, alginates, natural rubbers or natural fibers (such as for example jute, kenaf, hemp). The starches and celluloses are, in embodiments, modified, such as starch or cellulose esters with a degree of substitution of between 0.2 and 2.5, hydroxypropylated starches, or modified starches with fatty chains, among others.

Compounds I are employed as plasticizers at various effective concentrations, depending on the polymer used and desired properties of the compounded polymer formulations. In embodiments, compounds I are used at concentrations between about 1 and 80% by weight of the unplasticized polymer, or between about 10 and 50% by weight of the unplasticized polymer. In some embodiments, one or more of compounds I and Ia are incorporated into a polymer formulation by mixing at temperatures that are above the melting point of the polymer. In other embodiments, one or more compounds I are incorporated into a polymer formulation with a help of an optional volatile solvent. Many techniques for introducing plasticizer compounds to polymer compositions are known in the art, and the invention is not particularly limited as to the method of addition of compounds I into one or more polymer formulations. One or more of compounds I are employed, in embodiments, as a blend with additional compounds for the preparation of extrudable or moldable polymer compositions. Such additional compounds can include, for example, various inorganic and organic filler compounds, wood dust, reinforcing fibers, colorants, stabilizers, lubricants, anti-microbial additives, and the like.

In order to easily adjust the hydrophobic/lipophobic balance of compounds I for specific end uses, in embodiments where $R^1$ is a lower alkyl having six or less carbons, $R^1$ is conveniently transesterified with long chain alkyl groups. For example, where $R^1$ of compound I is initially methyl, ethyl, and the like, $R^1$ is easily transesterified with octyl, dodecyl, or hexadecyl alcohols or branched alcohols such as 2-ethylhexyl alcohol, by subjecting compound I to the desired replacement alcohol in the presence of a transesterification catalyst. Employing heat and/or vacuum in such a reaction causes the lower boiling alcohol to evaporate from the reaction vessel as it is displaced by the higher boiling alcohol, driving the reaction to completion.

In another useful embodiment of compounds I, the $R^1$ moiety contains a functional group. For example, $R^1$ contains, in embodiments, hydroxyl or amine functionality. The hydroxyl or amine functionality is, in some embodiments, capable of one or more subsequent reactions, for example esterification or amidation of a carboxylate group; reaction with an isocyanate group; or reaction with an acid chloride to yield the corresponding adduct of compound I. Many related variations are easily envisioned that serve to further functionalize the $R^1$ group. In some embodiments, adducts of compound I wherein the total sum of all β is 2 or more and wherein all $R^1$ moieties have functional groups are useful in polymerization and crosslinking schemes; these adducts are described in more detail below. In other embodiments, adducts of compound I are useful wherein the total sum of all β is 1, and the sole $R^1$ moiety contains a functional group.

In other embodiments of compound I, varying the nature of the oxocarboxylate employed leads to variations in resulting properties, where the sum γ of all α and β is 3 or less, thereby varying one or more equivalents of $R^2$ and $R^3$. Thus, by varying the oxocarboxylate of the hybrid ketal, solubility, boiling point, and hydrophobicity are, in embodiments, varied for one or more applications of compounds I as surfactants, solvents, plasticizers, and the like as described above.

One particularly useful embodiment of compound I wherein the sum of all β is 1 is where $R^1$ contains an acrylate functionality. As used herein, the term "acrylic" or "acrylate" is intended to collectively mean an acrylate, methacrylate, acrylamide, methacrylamide, or other similar moiety that is capable of subsequent polymerization or crosslinking reactions utilizing a free radical or redox mechanism. Acrylate adducts of compound I are represented as compound Ib:

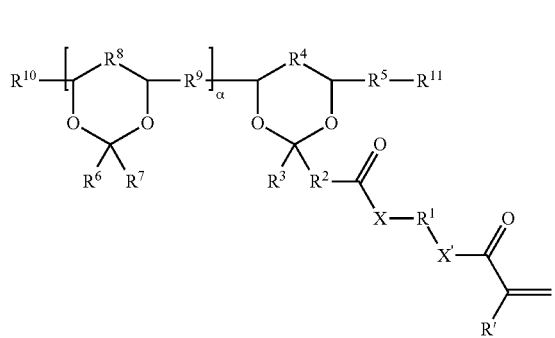

Ib wherein $R^1$-$R^{11}$ are as previously defined for compound I, α is an integer of 1 or greater, X and X' are independently O or NR wherein R is hydrogen or an alkyl group having six or less carbons, and R' is hydrogen or an alkyl group having six or less carbons.

In some embodiments, acrylic functionality is imparted by reaction of the corresponding alkyl ester moiety of compound I with a diol, aminoalcohol, or diamine, followed by reaction with acrylic acid, an ester thereof, or acrylyl chloride. Such reactions employ standard techniques commonly employed in the literature. Examples of compounds and conditions that are useful to react an ester of compound I with a diol, aminoalcohol, or diamine are generally described below for the reaction to form compound Ic. A subsequent reaction with an acrylate functional compound results in compound Ib. The subsequent reaction is carried out, in embodiments, by an esterification reaction of the hydroxyl or amine group of compound I with acrylic acid or methacrylic acid, or by reaction of the hydroxyl or amine with acrylyl chloride or methacrylyl chloride. In the latter embodiment, HCl that forms during the reaction is preferably scavenged by a base, for example ammonia, during the course of the reaction. Many techniques to react an hydroxyl or amine group with an acrylate functional compound are known in the literature.

The α, β-unsaturated portion of the acrylate functionality of compounds Ib are capable of radical, cationic, or anionic polymerization to result in a polymer network. Such reactions are widely used in the industry and one or more compounds Ib of the invention may be reacted using any of the known techniques of polymerization or crosslinking of acrylate functionalities. A plethora of references are available that discuss useful techniques for processing, polymerization, and crosslinking of acrylate functionalities. Radical polymerization or crosslinking reactions initiated by thermal, redox, electromagnetic radiation such as ultraviolet (UV), or electron beam (ebeam) are the most common of these known techniques. Some useful references discussing such means of polymerization of acrylate functional materials are Decker et al., *Macromol. Mater. Eng.* 286, 5-16 (2001); Burlant, W., U.S. Pat. No. 3,437,514; Endruweit, et al., Polymer Composites 2006, 119-128; Decker, C., *Pigment and Resin Technology* 30(5), 278-86 (2001); and Jönsson et al., *Progress in Organic Coatings* 27, 107-22 (1996). Other known and useful methods are those taught by U.S. Pat. Nos. 3,437,514; 3,528, 844; 3,542,586; 3,542,587; 3,641,210. Such polymerization reactions are particularly advantageous where one or more compounds Ib are polymerized, for example, in situ in a coated formulation, in a syrup preparation for coating, and the like.

Many useful extensions of the invention are readily envisioned wherein compounds Ib are employed. For example, in embodiments, compounds Ib are blended with one or more additional acrylate functional compounds and/or additional vinyl functional compounds. The additional acrylate or vinyl functional compounds have, in some embodiments, more than one acrylate or vinyl group per molecule, so that they are capable of crosslinking reactions. After processing, for example coating, the blends of compounds Ib and other acrylate or vinyl functional compounds are reacted to form a linear or crosslinked network. The resulting networks are thermoset or thermoplastic, depending on whether or not the network is crosslinked. It is readily understood that the properties of the networks will vary greatly depending on both the nature of the compounds used and crosslink density.

Additional acrylate functional compounds include compounds having one or more acrylate, alkylacrylate, acrylamide, or alkylacrylamide residues. Non-limiting examples of useful acrylate functional compounds include acrylic acid, methacrylic acid, acrylamide, methacrylamide, N-hydroxymethyl acrylamide, methacryloxyethyl phosphate, acrylonitrile, methacrylonitrile, 2-acrylamido-2-methylpropanesulfonic acid and salts thereof; maleic acid, its salt, its anhydride and esters thereof; monohydric and polyhydric alcohol esters of acrylic and alkylacrylic acid such as 1,6 hexane diol diacrylate, neopentyl glycol diacrylate, 1,3 butylene dimethacrylate, ethylene glycol diacrylate, trimethylolpropane triacrylate, pentaerythritol triacrylate, pentaerythritol tetracrylate, etc.; other oxygenated derivatives of acrylic acid and alkylacrylic acids, e.g., glycidyl methacrylate, hydroxyethyl methacrylate, hydroxypropyl methacrylate, etc.; halogenated derivatives of the same, e.g., chloroacrylic acid and esters thereof; and diacrylates and dimethacrylates, e.g., ethylene glycol diacrylate. In some embodiments, the additional acrylate functional compounds are present in blends with acrylate functional polyketals of up to about 50 mole percent, such as between about 1 and about 40 mole percent, of additional acrylate functional compounds.

Additional vinyl functional compounds include non-acrylate functional α, β-unsaturated compounds capable of copolymerizing with the acrylate functional compounds and/or compounds Ib. Non-limiting examples of additional vinyl compounds include aromatic polyvinyl compounds such as divinyl benzene, aromatic monovinyl compounds such as styrene, methyl substituted styrenes such as α-methyl styrene, vinyl toluene, t-butyl styrene, chlorostyrene, and the like; aliphatic monovinyl compounds such as α-olefins, e.g. propylene, 1-octene, and the like. Other additional vinyl functional compounds useful in blends with the acrylate functional polyketals are the divinyl and tetravinyl compounds disclosed in U.S. Pat. Nos. 3,586,526; 3,586,527; 3,586,528; 3,586,529; 3,598,530; 3,586,531; 3,591,626; and 3,595,687.

The utility of acrylate polymers is widely understood and is described throughout the literature. The above mentioned references describe some uses of acrylate polymers and networks; many others are described or envisioned by one of skill in the art. Pressure sensitive adhesives and protective coatings are common uses of acrylate polymers and networks. It will be appreciated that the combinatorial aspect of monomers Ib, due to nature of the $R^6$ and $R^7$ groups and the variability of the total sum of all α, imparts a wide range of properties to polymers formed from compounds Ib.

Cyclic Ketal Compounds

In some embodiments of compound I, the hybrid ketals of the invention are reacted to form cyclic diesters (diolides, or dilactones) or diamides (dilactams), collectively referred to herein as cyclic polyketals. Cyclic polyketals are useful as plasticizers, surfactants, phase transfer catalysts, additives, and as monomers for synthesis of various polymers, copolymers, and polymer blends. The cyclic polyketals have general formula Ic:

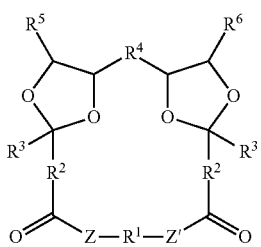

Ic wherein

Z and Z' are independently O or NR, wherein R is hydrogen or an alkyl group having six or less carbon atoms;

$R^1$ is a linear, branched, or cyclic alkyl group, or linear, cyclic, or branched alkenyl group, and optionally contains one or more heteroatoms;

$R^2$ is a covalent bond, a linear, branched, or cyclic alkyl group, or a linear, cyclic, or branched alkenyl group, and optionally contains one or more heteroatoms;

$R^3$, $R^5$ and $R^6$ are independently hydrogen or linear, branched, or cyclic alkyl groups, or linear, cyclic, or branched alkenyl groups, and optionally contain one or more heteroatoms; and $R^4$ is a covalent bond or a linear, branched, or cyclic alkyl group, or linear, cyclic, or branched alkenyl group, or a linear or branched alkynyl, aryl, aralkyl, or aralkenyl group and optionally contains one or more heteroatoms.

Heteroatoms that are contained in one or more R groups of compounds Ic include, in some embodiments, O, N, S, Cl, Br, I, or. F; in some such embodiments, O may be contained as an oxo moiety. In embodiments, the cyclic polyketals Ic are derived from compounds I wherein γ is 2 or 3 and β is 2. In some embodiments, the cyclic polyketals are based on erythritol ketals of oxocarboxylate diesters; in other embodiments, the cyclic polyketals have structures that are based on sorbitol ketals of oxocarboxylate diesters, such as

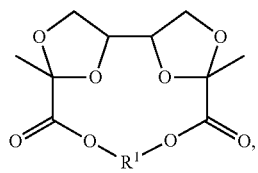

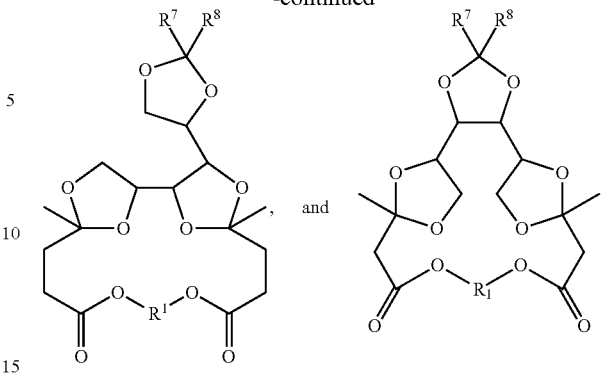

wherein $R^1$ is as defined for compound Ic, and $R^7$ and $R^8$ are the same as $R^6$ and $R^7$ in compound I, respectively; and additionally, in some embodiments, $R^6$ and $R^7$ are connected to each other as part of 5-12 membered ring. Where $R^6$ and $R^7$ are connected to each other as part of 5-12 membered ring, the structure is, in embodiments, the result of ketal formation from a cyclic ketone. In embodiments wherein Z and Z' are O, $R^1$ is a fragment of dihydric alcohol $R^1(OH)_2$. Preferably, both OH of $R^1(OH)_2$ are primary hydroxyl groups. In some embodiments, Z is O and Z' is NR and $R^1$ is the fragment of an aminoalcohol; in still other embodiments both Z and Z' are NR and $R^1$ is the fragment of a diamine.

Suitable dihydric alcohols (diols) used to form the cyclic polyketal carboxylates Ic include, for example, 1,2-ethanediol (ethylene glycol), 1,2-propanediol (propylene glycol), 1,3-propanediol, 2,2-dimethyl-1,3-propanediol (neopentyl glycol), 2-butyl-2-ethyl-1,3-propanediol, 3-mercaptopropane-1,2-diol (thioglycerol), dithiothreitol, 1,2-butanediol, 1,3-butanediol, 1,4-butanediol, 2,3-butanediol, 1,5-pentanediol, 3-methyl-1,5-pentanediol, 1,6-hexanediol, 2-ethyl-1,3-hexanediol, cyclohexane-1,2-diol, cyclohexane-1,4-diol, 1,4-bis-hydroxymethylcyclohexane, 1,4-dioxane-2, 3-diol, 3-butene-1,2-diol, 4-butenediol, 2,3-dibromobutene-1,4-diol, 1,8-octanediol, 1,10-decanediol, 1,12-dodecanediol, benzene-1,2-diol (catechol), 3-chlorocatechol, indane-1,2-diol, tartaric acid, and 2,3-dihydroxyisovaleric acid, diethylene glycol (DEG), triethylene glycol, tetraethylene glycol, dipropylene glycol, tripropylene glycol, tetrapropylene glycol, xylene glycol, 1,3-benzenediol (resorcinol), 1,4-benzenediol (hydroquinone), o, m, or p-benzene dimethanol, o, m, or p-glycol phthalates, o, m, or p-bis-1,2-ethylene glycol phthalates, o, m, or p-bis-1,2-propylene glycol phthalates, o, m, or p-bis-1,3-propylene glycol phthalates, diols prepared by hydrogenation of dimer fatty acids, hydrogenated bisphenol A, hydrogenated bisphenol F, propoxylated bisphenol A, isosorbide, 2-butyne-1,4-diol, 3-hexyne-3,5-diol (SURFYNOL® 82, available from Air Products of Allentown, Pa.) and other alkyne-based diol products marketed under the SURFYNOL® brand name by Air Products of Allentown, Pa., and the like. These diols are, in embodiments, selected from those that have a relatively low boiling point so that the resulting cyclic ketals Ic also have relatively low boiling points and can be easily purified by distillation under vacuum at temperatures below about 300°-350° C. to avoid undesired amounts of thermal decomposition. In other embodiments, higher diols may be useful.

Suitable aminoalcohols used to form the cyclic polyketal carboxylate amides Ic include, for example, 2-aminoethanol, 3-aminopropan-1-ol, isopropanolamine, 2-aminopropan-1-ol, 2-aminobutan-1-ol, 2-amino-3-methylbutan-1-ol, 2-amino-4-methylpentan-1-ol, 6-aminohexan-1-ol, 1-amino- 3-chloropropan-2-ol, 7-aminobicyclo[2.2.2]octan-8-ol, 2-aminopyridin-3-ol, 2-amino-4-phenylphenol, 5-aminonaphthalen-1-ol, 4-(4-aminophenyl)phenol, and the like. Suitable diamines used to form the cyclic polyketal amides Ic include, for example, methanediamine, ethane-1,2-diamine, 1,6-hexanediamine, but-2-ene-1,4-diamine, Metformin, butane-1,4-diamine, propane-1,2-diamine, benzene-1,3-diamine, 2-methylbenzene-1,3-diamine, 4-chlorobenzene-1,3-diamine, piperazine, and the like. Certain other polyfunctional amines, such as diethylenetriamine, contain three amino groups but only two primary amines; in such cases it is understood that the primary amine groups are more reactive than the secondary amine and will react preferentially in reactions such as those described herein; thus, in actual use, such polyamines are useful as diamine equivalents in one or more such embodiments.

Compounds Ic are not particularly limited as to the process to make them. One example of a useful synthetic scheme for generating one specie of compound Ic is shown below, wherein the starting compound I is the hybrid ketal of sorbitol or mannitol with one equivalent of acetone and two equivalents of ethyl levulinate, which is then reacted with ethylene glycol in the presence of a catalyst to form the corresponding compound Ic:

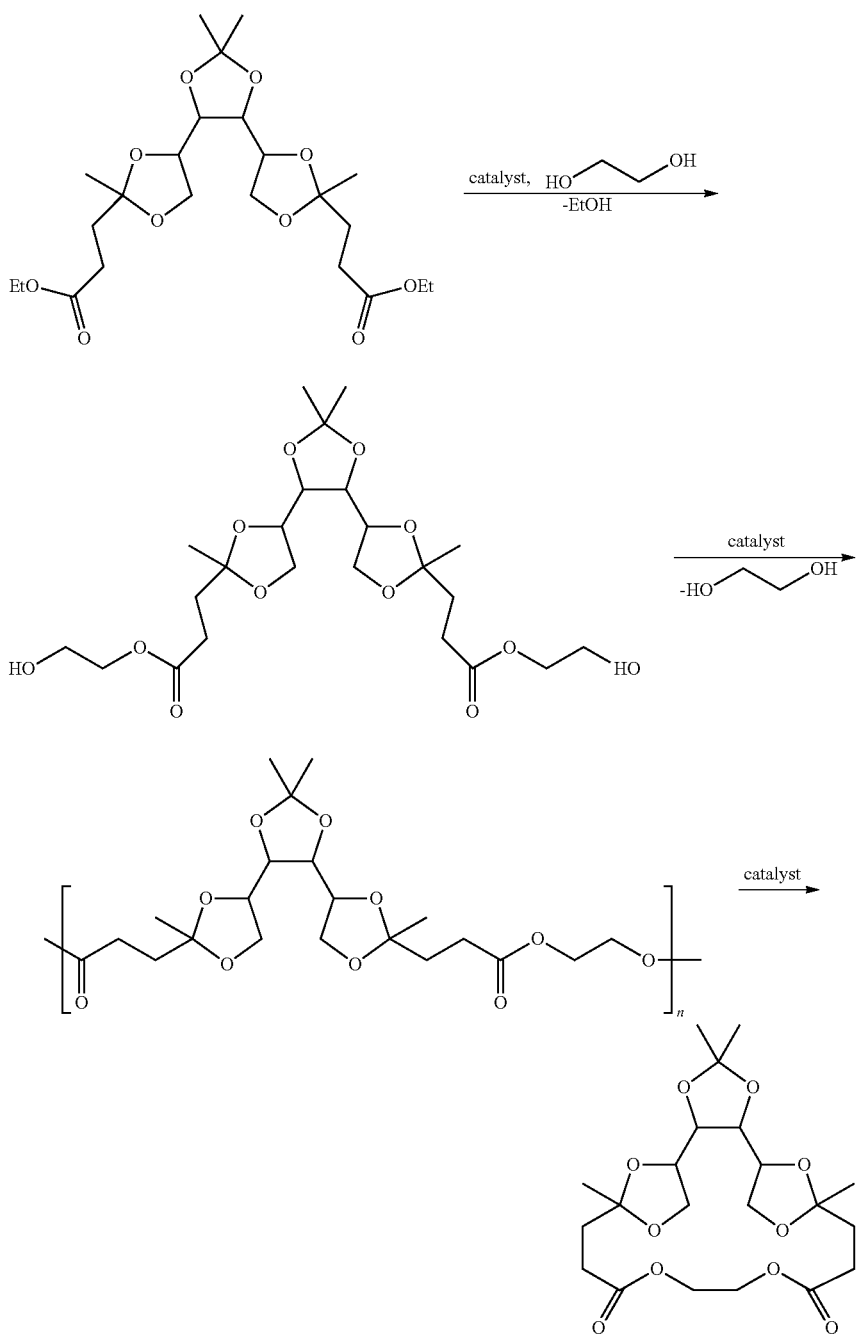

wherein n is degree of polymerization.

In some embodiments of compound Ic where Z and Z' are O, preparation of compounds Ic is carried out by reacting one or more ketal carboxylates of compound I, wherein β is at least 2 and $R^1$ is R', such that R' is the residue of a monohydric alcohol, R'OH, with a dihydric alcohol (a glycol) $R^1(OH)_2$. Typically the reaction is carried out by esterification or transesterification using conventional techniques employed in the literature. In embodiments, transesterification is carried out in the presence of a catalyst; preferably the catalyst is not a protic acid catalyst. In embodiments, useful transesterification catalysts include, without limitation, alkali, alkali-earth and transitional metal hydroxides, oxides, alkoxides and salts thereof with carboxylic, boric, polyboric, phosphoric acids, aluminates, silicates, basic alumina, silica, titania, zirconia, molecular sieves, or non-volatile tertiary and quaternary amines.

In some embodiments, the reaction is conducted under conditions sufficient to distill R'OH and any excess of glycol $R^1(OH)_2$; in some embodiments, these conditions include elevated temperature and reduced pressure. In some embodiments, $R^1(OH)_2$ is provided at least about 1 mol of $R^1(OH)_2$ per 1 mol of ketal diester; in other embodiments, a molar excess of $R^1(OH)_2$ is provided. In some embodiments, the reaction is conducted at elevated temperatures until substantially all R'OH and excess $R^1(OH)_2$ have been distilled from the reaction vessel. In some embodiments, additional hydroxylic or carboxylic compounds are present in the reaction mixture. In some embodiments, cyclization is subsequently affected directly via a second transesterification reaction. In embodiments, the second transesterification reaction employs a transesterification catalyst; the transesterification catalyst may be the same or different from the first transesterification catalyst. In some such embodiments, useful transesterification catalysts are those that do not form volatile compounds that can co-distil with compound Ic. Nonlimiting examples of such catalysts include alkali and alkali earth metal alkoxides, oxides, and salts thereof. Such catalysts allow, in embodiments, preparation of cyclic ketals Ic in a form substantially devoid of catalytic species capable of causing polymerization via ring opening. In other embodiments, a linear polyester is first formed from the glycol ester of compound I, followed by depolymerization with concomitant cyclization. This reaction process is generally applicable to form all structures Ic, wherein various compounds as starting materials and varying reaction conditions may are envisioned for employment. In some embodiments, reaction conditions to form Ic are employed so as to distill or otherwise remove one or more compounds I from the reaction mixture.

In various embodiments of the reaction methods discussed above, the transesterification catalysts are the same or different in both steps of the reaction. The catalysts may be a combination of more than one catalyst. In some embodiments, the second step further includes addition of an additional quantity of catalyst to the reaction vessel to accelerate depolymerization and/or cyclization of compounds Ic. The catalysts are, in various embodiments, homogeneous or heterogeneous in the reaction mixture; in some embodiments, the catalyst is covalently bonded to a solid support in a column or other reaction vessel through which the reaction substituents are passed. Insoluble catalysts may be resin-based or porous or non-porous carbon, silica, alumina, titania, or zirconia based.

In some embodiments, the reaction steps are carried out with use of mechanical stirring or gravity flow to allow mixing of all compounds present in the reaction mixture. In embodiments, batch distillation of compounds is carried out until majority or substantially all of the compounds have been distilled out as cyclic ketals Ic. In some embodiments, this distillation process is carried out in a continuous mode, and any of the residual compounds I or polymeric forms thereof are recycled. Distillation can optionally include separation of any of the stereoisomers of compounds I.

In embodiments where a polymeric material is formed prior to depolymerization and cyclization, the degree of polymerization, n, is about 1 to 20,000. In some embodiments, n is less than about 200, and in other embodiments n is less than about 50. In embodiments, n is chosen such that the polymeric compounds have melt viscosity sufficiently low at the reaction temperature to allow for a mechanical stirring or gravity flow.

In embodiments, useful examples of cyclic ketals derived from ketal diesters of sorbitol include, without limitation, the following structures.

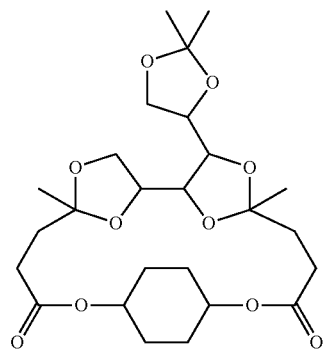

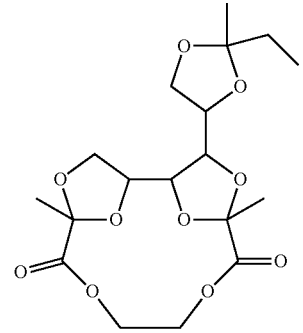

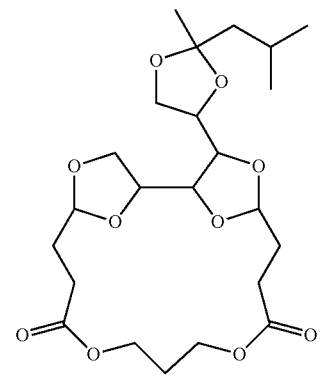

31
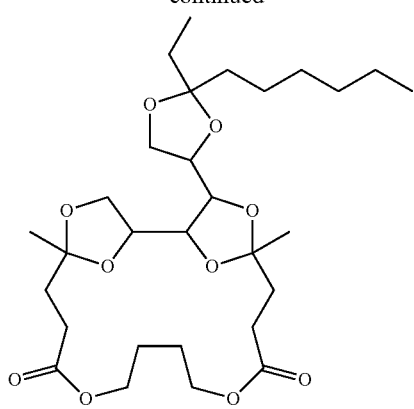
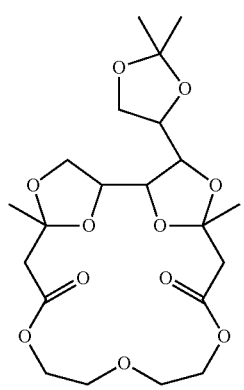
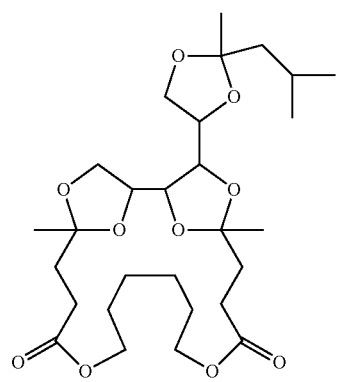
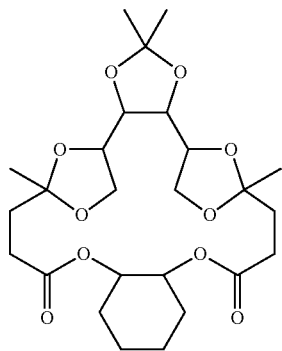
32
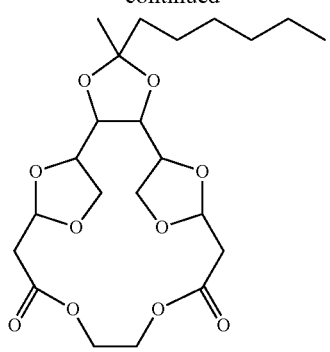
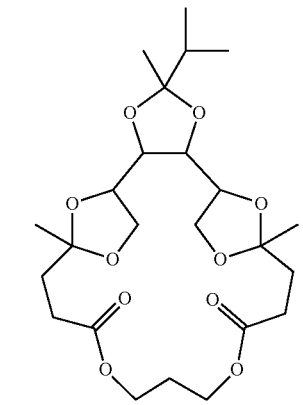
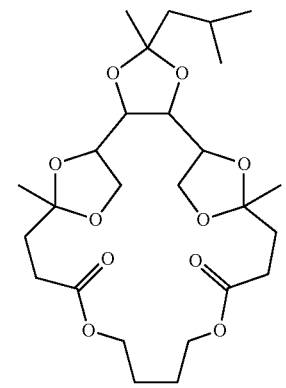
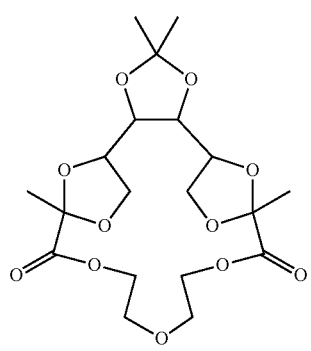

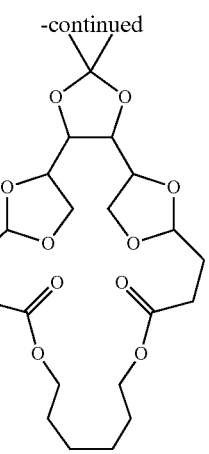

In embodiments, useful examples of cyclic ketals derived from ketal diesters of erythritol or threitol include, without limitation, the following structures.

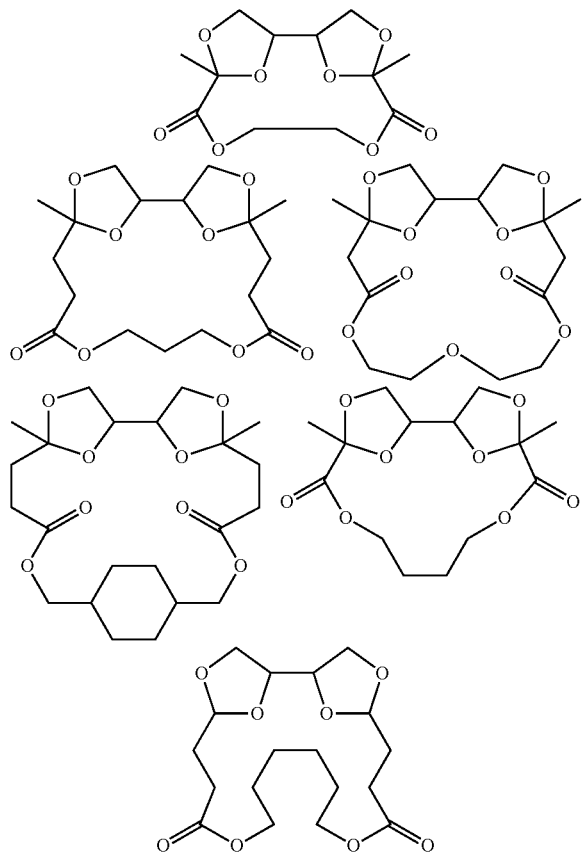

Cyclic ketals Ic may also be employed, in embodiments, as phase transfer catalysts. In embodiments, $R^1$-$R^8$ are chosen to tailor the hydrophobic-hydrophilic properties of compounds Ic. In other embodiments, phase transfer properties are manipulated by employing desired stereochemical features of cyclic ketals Ic to impart a ring morphology that enables the compound to act as a phase transfer catalyst. In still other embodiments, both chemical makeup of $R^1$-$R^8$ and stereochemistry are chosen and employed advantageously. Similarly, cyclic ketals Ic are, in various embodiments and by suitably adjusting the stereochemistry and/or structure of $R^1$-$R^8$ and resulting ring morphology, surfactants, plasticizers for polymer matrices, coalescing solvents, solvents, cosolvents, and coatings additives.

Where Z and/or Z' are NR (and R is hydrogen or an alkyl group having less than or equal to six carbons), the reaction to form Ic typically is carried out using similar means as those used to make the cyclic diesters where both Z and Z' are O, except that, in some embodiments, no catalyst need be employed. In general, any conventional techniques employed in the literature may similarly be employed to displace a monovalent alcohol with a diamine or aminoalcohol, thus enabling formation of the cyclic ketal amide or cyclic ketal carboxylateamide.

In embodiments, compounds Ic are useful as monomers for synthesis of many thermoplastic and thermoset polymers and co-polymers comprising at least one fragment of formulae Id:

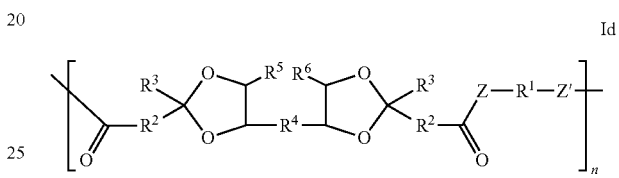

Id wherein $R^1$, $R^2$, $R^3$, $R^4$, $R^5$, $R^6$, and Z' are as described for compound Ic and n is an integer of between about 1 and 20,000. Cyclic ketals Ic are employed in ring opening polymerization reactions, either alone or with one or more additional co-monomers. Initiators for ring opening polymerization are, in embodiments, a hydroxyl compound, for example a monohydric alcohol, polyhydric alcohol, or an hydroxyl-functional ester of a carboxylic acid.

In various embodiments, copolymers comprising fragment of formula (Id) are random, alternating, or block. In embodiments, the copolymers comprising fragment of formula (Id) are linear, or branched or hyperbranched, star, or dendritic structures; such structures are, in embodiments, cross-linked. Block copolymers are, in embodiments, single blocks, diblocks or multiblocks (e.g. triblocks, tetrablocks, pentablocks). Non-limiting examples of co-monomers useful for the preparation of random and block co-polymers comprising fragments of formula Id include, in embodiments, esters of dicarboxylic acids, for example esters of aromatic dicarboxylic acids such as terephthalic acid, isophthalic acid, phthalic acid, or naphthalene dicarboxylic acid; esters of aliphatic linear, branched, or cyclic acids having from about 2 to 40 carbon atoms such as adipic acid, succinic acid, glutaric acid, pimelic acid, oxalic acid, maleic acid, fumaric acid, diglycolic acid, cyclohexane 1,4-dicarboxylic acid, 4-cyclohexene 1,2-dicarboxylic acid, nadic acid, itaconic acid, mesaconic acid, citraconic acid, muconic acid, dihydromuconic acid, or dimeric fatty acids; esters and free acids of tricarboxylic aromatic and aliphatic compounds, for example mellitic acid, benzene 1,3,5-tricarboxylic acid, citric acid, or sorbitol 1,2-3,4- or 5,6-levulinic tris-triketal; esters and lactones of hydroxycarboxylic acids, for example lactic acid, lactide, glycolide, 1,4-dioxan-2-one, alkyl-substituted 1,4-dioxan-2-ones, ε-caprolactone, isomers of alkyl-substituted caprolactones, isomers of hydroxybenzoic acids, isomers of hydroxynapthoic acids, isomers of hydroxymethylbenzoic acids; ketals of levulinic acid with trihydric alcohols such as glycerol, trimethylol propane, trimethylol ethane, or penthaerythritol; or cyclic glycerol levulinate ketal carboxylates; carbonic acid diesters (e.g. cyclic and acyclic carbonate di-esters of glycols and monohydric alcohols); polyhydric alcohols having two or more hydroxyl groups, in some embodiments having 2 or more primary hydroxyl groups, for example dihydric alcohols such as ethylene glycol, 1,2-propanediol or 1,3-propanediol, 1,4-butanediol, diethylene glycol, propylene 1,2-glycol, dipropylene glycol, neopentyl glycol, pentane-1,5-diol, hexane-1,6-diol, decane-1,10-diol, or polyethylene glycols, polypropylene glycols, or copolymers thereof with 2 hydroxyl groups; linear, branched, or cyclic polyhydric alcohols and glycols such as isosorbide, polyethylene glycols, polypropylene glycols, or copolymers thereof having more than 2 hydroxyl groups, poly-trimethyleneglycol, poly-tetramethylene glycol, glycerol, diglycerol, trimethylol propane, pentaerythritol, sorbitane isomers, sorbitol, xylitol, erythritol and other polyhydric alcohols derived by hydrogenation of carbonyl group of monosaccharides; and polyhydric alcohols derived by introduction of hydroxyl groups to unsaturated fatty acid chains of mono, di triglycerides; in yet further embodiments, examples include dihydric and polyhydric alcohols that are ethoxylated or propoxylated.

In embodiments, block co-polymers comprising fragment Id include copolymers having blocks comprising suitably functionalized polyolefins, for example polyethylene, polypropylene, polyisobutylene, polyisoprene; copolymers of acrylonitrile, butadiene, styrene, halogenated olefinic polymers such as poly(vinyl chloride), polystyrene, aromatic and aliphatic polyesters, polylactide polyesters, polyhydroxyalkanoate polyesters, polyethers such as polyethylene oxide, poly-1,2-propylene oxide, poly-1,3-propylene oxide, and poly-1,4-butylene oxide; blocks can also comprise lactide, glycolide, alkyl and aryl substituted 1,4-dioxan-2-one residues; caprolactone residues, polymerized glycerol levulinate ketal lactones, polyamides, polypeptides, and polysaccharides.

In embodiments, advantages of using compounds Ic over counterpart non-cyclic esters to form polymers Id include the ability to control polydispersity of resulting polymers, rapid synthesis of polymers via ring opening polymerization, ease of preparing complex block and graft co-polymers, and overall improved polymer properties as compared to polymers obtained by polycondensation of non-cyclic esters. In some embodiments, polymers comprising at least one fragment of formulae Id can be polyurethanes, polyureas, or polyurethane ureas. Ring-opening polymerization of compounds Ic can be carried in the presence of one or more catalysts known in the art to effect ring opening polymerization of other cyclic esters, in a neat form, and optionally, in the presence of a non-ester aprotic solvent. Non-limiting examples of known useful catalysts include transitional metal alkoxides and salts with carboxylic and sulfonic acids and Lewis acids. In embodiments, titanium, zinc, and tin-based alkoxides are useful catalysts. Catalysts known in the art to be useful for ring opening polymerization of either lactide, caprolactone, dioxanone are useful to polymerize or co-polymerize the cyclic ketals Ic.

In some embodiments, polymers comprising at least one fragment of formula Id contain one, two or more functional endgroups. In embodiments, the endgroups are selected from hydroxyls, isocyanates, amines, amides, substituted amides, acrylic esters, methacrylic esters, and allyl esters. In embodiments, hydroxyl-terminated compounds of formula Id having two or more hydroxyl-terminated groups are useful for preparing polyurethane polymers and radiation or UV-curable polymers and pre-polymers. In some embodiments, hydroxyl-terminated compounds comprising fragment Id are gravity flowable at temperatures in between about 0° C. and 150° C.

In embodiments, polymers comprising at least one fragment of formula Id are blended or alloyed with other polymers, with or without phase separation. Suitable polymers for blending include, in general, any of the polymeric structures known in the art. Non-limiting examples include polyolefins, polystyrene, polyesters (including renewable PLAs and PHAs, and non-renewable), polysaccharides, polyurethanes, polyethers, polyamides. In embodiments, polymers comprising at least one fragment of formulae Id and their blends or alloys can be optionally compounded with organic and inorganic fillers, colorants, processing aids, stabilizers, antifouling agents, adjuvants, biocides, and the like. Such compositions are useful for making, in various embodiments, a variety of molded, extruded, rolled, cast, solvent cast, or coated rigid and elastic parts, foams, coatings, surfactants, adhesives, sealants. The compositions are, in embodiments, posttreated, cut or shaped, crosslinked, painted, and the like. In some embodiments, the polymers, copolymers, or formulations employing them, are recycled by treatment with alcohols or glycols in the presence of a suitable transesterification catalyst, e.g. a base, to recover any monomers of formulae I or Ic.

Oligomers and Polymers of Structures I and III

The compounds having structures I and III are, in embodiments of the invention, polymerized via one or more synthetic schemes to arrive at a number of useful oligomeric or polymeric embodiments. In general, compounds I wherein the total sum of all β of 2, and compounds of structure III wherein both ketal moieties are ketal carboxylates, have diester or diacid functionalities. Such embodiments of compounds I and III are referred to, for the purposes of discussion below, as "bisketals", "bisketal carboxylates", or "bisketal esters". The bisketal carboxylates are suitable for one or more polymerization reactions. For example, polyols, polyesters, polyamides, polyisocyanates, polycarbonates, polyurethanes, poly (urethane urea)s, poly(urea)s, and copolymers thereof are all embodiments of oligomeric and polymeric structures achievable using the bisketal carboxylates. Additionally, in other embodiments, bisketal carboxylates are "capped" with reactive groups, for example, glycidyl, acrylate, or allyl groups; these groups are, in embodiments, subsequently polymerized to form one or more linear, branched, or crosslinked products.

Oligomers and polymers formed from bisketal carboxylates have at least one repeat unit represented by structure IV:

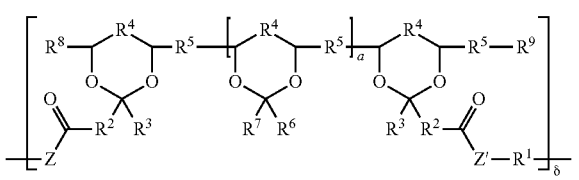

IV wherein
$R^1$ is a divalent linear, branched, or cyclic alkyl, a linear, branched, or cyclic alkenyl, alkynyl, aryl, or alkaryl moiety; and optionally contains one or more heteroatoms; and $R^1$ is the same or different for each occurrence;
$R^2$ is a covalent bond or a linear or branched alkyl group optionally containing one or more heteroatoms; and $R^2$ is the same or different for each occurrence;
$R^3$ is hydrogen, a linear, branched, or cyclic alkyl optionally containing one or more heteroatoms; and $R^3$ is the same or different for each occurrence;

$R^4$ is a covalent bond, methylene, or alkylmethylene, wherein a covalent bond indicates a 5-membered ring and a methylene or alkylmethylene indicates a 6-membered ring, and $R^4$ is the same or different for each occurrence;

$R^5$ is a covalent bond, methylene, ethylene, hydroxymethylene, oxygen, —$CH_2$—O—$CH_2$—, or a polymeric moiety, and $R^5$ is the same or different for each occurrence;

$R^6$ and $R^7$ are independently linear, branched, or cyclic alkyl groups;

$R^8$ and $R^9$ are independently hydrogen, a linear, branched, or cyclic alkyl, a linear, branched, or cyclic alkenyl, alkynyl, aryl, alkaryl, or a polymeric moiety and optionally contain one or more heteroatoms;

Z and Z' are independently O or NR where R is hydrogen or an alkyl group having 6 or less carbon atoms;

a is an integer of at least 1 and defines a ketal unit, wherein a ketal units are disposed contiguously to $R^5$, $R^8$, $R^9$, or a combination thereof; and δ is an integer of at least 1.

Heteroatoms that are contained in one or more R groups of compounds IV include, in some embodiments, O, N, S, Cl, Br, I, or. F; in some such embodiments, O may be contained as an oxo moiety. It will be understood that the placement of the α alkyl ketal moieties in relation to the two ketal carboxylate moieties is not limited by the representation of structure IV; in fact, the alkyl ketal moieties are, in embodiments, on one or both side of the ketal carboxylate moieties in structure IV. It will also be readily understood that the analogs of compound IV wherein the total sum of all β is more than 2 are, in embodiments, employed in one or more reactions that are analogous to compound IV wherein the corresponding branched, hyperbranched, dendritic, or crosslinked network polymers are formed. It will further be understood that a combination of bisketal carboxylates and analogs thereof, represented by compounds I wherein the sum of all β is more than 2, are in embodiments employed together in one or more reactions to provide varying degrees of branching or crosslinking, as is desirable for one or more end uses. Compounds V, described below, as well as compounds Ic, may also be employed in conjunction with one or more other compounds of the invention to arrive at useful polymeric structures, as will be described below in detail.

Oligomers and polymers formed from compounds III wherein both ketal moieties are ketal carboxylates have at least one repeat unit represented by structure Va, structure Vb, or a combination thereof:

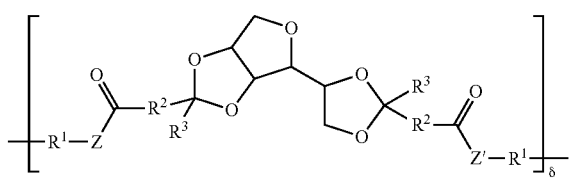

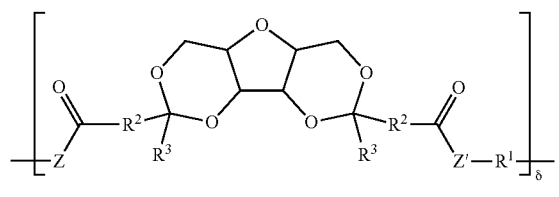

wherein R1, $R^2$, $R^3$, Z and Z', and δ are as defined for compound IV. For the purposes of the following discussion, compounds Va and Vb are referred to collectively as "compounds V."

In embodiments, oligomers and polymers V are the products of subsequent reactions of the corresponding bisketal carboxylates III wherein $R^3$ and $R^5$ are both

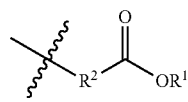

and $R^1$ is the residue of a monovalent alkanol. Such embodiments of compounds III are analogous to compounds I wherein the sum of all β is 2. Collectively, these compounds are, for the purposes of this discussion, referred to as "bisketals," "bisketal carboxylates," or "bisketal acids." The polymerization of bisketals I and III, in various embodiments, lead to compounds IV and V.

Polyester Oligomers, Polyols, and Polymers.

In some embodiments, the bisketal carboxylates of the invention are reacted with one or more diols to form linear polyester oligomers, polyester polyols, or polyester polymers. Whether a polyester is categorized as an oligomer, polyol, or polymer depends on endgroup identity and molecular weight. "Polyester oligomers" are defined as having a number average δ of 12 or less, wherein and not all endgroups are hydroxyl. "Polyester polyols" are defined as having a number average S of 12 or less, wherein an average of two endgroups per molecule contain an hydroxyl moiety. "Polyester polymers" are defined as having a number average δ of more than 12. Bisketals are reacted in an esterification or transesterification reaction with one or more diols to form linear oligomers and polymers of structures IV and Va. Suitable diols in such reactions include, in various embodiments, any of the diols mentioned above. The reactions and polymers are not particularly limited as to the nature of the diol used. The bisketal carboxylates are also reacted, in some embodiments, with triols or higher polyols, or a mixture of diols with some amount of triol or higher polyol, to form branched, hyperbranched, dendritic, or crosslinked network polyesters. And, in some embodiments, mixtures of bisketal carboxylates and a minor amount of trisketal carboxylate or a higher polyketal, e.g. structures I wherein the total sum of all β is greater than 2, are employed in one or more polyesterification reactions to give variable degrees of branching and/or crosslinking.

In some embodiments of compounds IV and Va, the value of δ is between about 1 and 11. In other embodiments the value of δ is between about 12 and 100; in other embodiments the value of δ is about 100 to 500; in still other embodiments the value of δ is as high as about 1000. In embodiments, the value of α in structure IV is 1; in other embodiments it is greater than 1.

The polyester oligomers, polyester polyols, and polyester polymers of structures IV and Va are, in embodiments, synthesized using conventional transesterification polymerization catalysts and conditions. In some embodiments, the catalysts and conditions employed are the same as those employed in the polyesterification reactions described in Selifonov, U.S. Patent Publication No. 2008/0242721, the entirety of which is incorporated herein by reference. In some embodiments, catalysts such as a toluenesulfonic acid, sulfuric acid, hydrochloric acid, sulfamic acid, or a sulfonic acid are employed in various embodiments. In other embodiments an organometallic catalyst is employed, for example a catalyst based on titanium or tin, such as titanium tetrabutoxide (Ti(OBu)$_4$), or tin (II) octanoate. In some embodiments, the organometallic catalysts are preferred. However, the choice of catalyst is not particularly limited within the scope of the invention. Reaction conditions are optimized to reach the desired end product composition and molecular weight. For example, in some embodiments where a polyester oligomer is desired, a stoichiometric excess of bisketal carboxylate is employed relative to diol. In some embodiments where a polyester polyol is desired, a stoichiometric excess of diol is employed relative to bisketal carboxylate. In some embodiments where a polyester polymer is desired, a 1:1 stoichiometric ratio of bisketal carboxylate to diol is employed. Other reaction conditions such as temperature and pressure are also varied, in embodiments, to reach the desired end product composition, molecular weight, crystalline content, and the like as required for one or more applications.

The polyester polymers of the invention have, in embodiments, excellent thermal stability and have superior tensile properties. In some embodiments, the polyester polymers of the invention are stable in air at temperatures of up to 250° C. In other embodiments, the polyester polymers of the invention are stable in air at temperatures up to about 300° C. In still other embodiments, the polyester polymers of the invention are stable in air at temperatures of over 300° C.

Polyester co-oligomers, polyester copolyols, and polyester copolymers generally corresponding to the polyester oligomers, polyester polyols, and polyester polymers are formed, in embodiments, by reacting a bisketal carboxylate or a polyester polyol with one or more additional diacids or diesters, diols, or a mixture thereof to give the corresponding polyester co-oligomer, polyester copolyol, or polyester copolymer. For example, a polyester polyol can be reacted with, for example, adipic acid or methyl isophthalate, to give the corresponding polyester co-oligomer, polyester copolyol, or polyester copolymer. Many other variations are easily envisioned. Non-limiting examples of suitable diols include any of those listed above. Non-limiting examples of suitable diacids (or esters of diacids) include aliphatic, cycloaliphatic or aromatic dicarboxylic acids, for example, succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, or hydrogenated dimerized fatty acids. The methyl, ethyl, propyl, butyl or phenyl esters of the acids listed above are suitable substitutes for the diacid component, as well as acid anhydrides (such as o-phthalic, maleic or succinic acid anhydride or a mixture thereof. In embodiments, the copolyester species of the invention are synthesized using conventional transesterification polymerization catalysts and conditions, such as any of those described above. Applications for polyester co-oligomers, polyester copolyols, and polyester copolyesters of the invention are similar, in embodiments, to those for homopolymers, except that a broader range of physical properties is available by the use of comonomers. For example, the incorporation of terephthalate as a diester in a copolymer provides, in some embodiments, increased crystalline content.

Crosslinked or branched analogs of various polyketal copolyesters of the invention are readily formed by employing a major proportion of bisketal carboxylates and diacids or esters thereof, with a minor proportion of a tricarboxylic acid or higher polyacid or ester thereof. It will be easily understood that trisketals and higher polyketals, as well as triols and higher polyols and triacids and higher polyacids, can be employed to form the corresponding crosslinked polymer or branched polymer. Importantly, mixtures of e.g. bisketal carboxylates and a minor amount of trisketal carboxylate or a higher polyketal carboxylate; or mixtures of diols and a minor amount of triols or higher polyols; or mixtures of diacids and a minor amount of a triacid or higher polyacid; or a combination of any of these can be advantageously employed to give variable degrees of branching and/or crosslinking. Some examples of suitable triacids include 1,3,5-trimethylcyclohexane-1,3,5-tricarboxylic acid, cis or trans aconitic acid, propane-1,2,3-tricarboxylic acid, hemmellitic acid, isocitric acid, and the like.

In other embodiments, polyester polyols are employed in the ring opening reaction of one or more lactones to form the corresponding copolyester. Ring opening polymerization of lactones is carried out using one or more catalysts and using reaction conditions suitable for ring opening polymerization. Catalysts and reaction conditions employed in such reactions are any of those used in the art for ring opening reactions of lactones. For example, some ring opening polymerization catalysts are based on transition metals such as zinc, tin, or titanium. Without limiting the species of catalysts or reaction conditions employed, any of the catalysts or reaction conditions described in Hori et al., U.S. Pat. No. 5,516,883 or Schechtman et al., U.S. Pat. No. 5,648,452 are useful. Activated carbon as employed by Endo et al., EP1857484 or organic catalysts employed as described in the article published at www.almaden.ibm.com/st/chemistry/ps/catalysts/RingOpening/may be used to affect the ring opening polymerization of lactones using a polyester polyol of the invention as the initiating specie. The above examples are not limiting as to the type of catalyst or set of reaction conditions that can be employed in a ring opening polymerization of lactones.

Suitable lactones for the ring opening polymerization initiated by one or more polyketal polyols of the invention include, without limitation, propiolactone, pivalolactone, diketene, dimethyldiketene, β-butyrolactone, 4-butyrolactone, 4-valerolactone, δ-caprolactone, ε-caprolactone, 5-ethenyl-5-methyloxolan-2-one, gluconolactone, glucuronolactone, D-galactonolactone, coumarin, hydrocoumarin, ascorbic acid lactone, α-angelicalactone, 2-acetylbutyrolactone, 6-propyloxan-2-one, 6-ethyloxan-2-one, ribonolactone, arabonolactone, λ-nonalactone, bicyclononalactone, 5-nonalactone, λ-decalactone, pantolactone, 2-dehydropantolactone, 5-butoxolan-2-one, isocrotonolactone, 6-hexyloxan-2-one 5-heptyloxolan-2-one, 5-propyloxolan-2-one, 6-[(E)-pent-2-enyl]oxan-2-one, cocolactone, isocitric lactone, 2-hydroxy-6-methylpyran-4-one, 1-oxacyclododecan-2-one, ε-dodecalactone, 1-oxacyclopentadecan-2-one, 1-oxacycloheptadecan-2-one, L-arabino-1,4-lactone, 4-hydroxy-4-methyloxan-2-one, homoserine lactone, 4-methyl-7-propan-2-yloxepan-2-one, and the like.

In one embodiment of a lactone ring opening polymerization, one or more polyketal polyols of the invention are employed in the ring opening polymerization of SEGETOLIDE™ (available from Segetis, Inc. of Golden Valley, Minn.) or its dimer to form the corresponding levulinate-glycerol ketal polyester. The structure of SEGETOLIDE™ and its dimer, as well as methods for the ring opening polymerization of both compounds, are found in U.S. Patent Publication No. 2008/0242721, the contents of which are incorporated by reference herein in their entirety. The methods disclosed therein are suitable, in embodiments, for initiating the ring opening polymerization using the polyester polyols of the invention as initiators.

The polyester oligomers and co-oligomers, polyester polyols and copolyols, and polyester polymers and copolymers are useful in a variety of industrial applications. For example, the polyester polyols and copolyols are useful in one or more subsequent reactions to form a variety of polymeric structures, as will be described in detail below. The polyester oligomers and co-oligomers are suitable, in embodiments, as coalescing solvents in one or more film forming formulations including dispersions, emulsions, or solutions. Suitable examples of film forming formulations include varnishes, protective coatings, latex paints, and the like. The polyester oligomers and co-oligomers are, in embodiments, also useful as plasticizers with various polymers. For example, where $\delta$ is less than about 5, the polyester oligomers and co-oligomers are useful as plasticizers in one or more polymer formulations. Suitable polymers for use with the polyester oligomers and co-oligomers of the invention include, for example, any of those listed above for use with compounds I and Ia. Thus, for example, poly(vinyl chloride) is blended with one or more polyester oligomers or co-oligomers to form a plasticized formulation. The polyester oligomers and co-oligomers of the invention are used at various effective concentrations, depending on the polymer used and desired properties of the compounded polymer formulations. In embodiments, the polyester oligomers and co-oligomers of the invention are used at concentrations between about 1 and 80% by weight of the unplasticized polymer, or between about 10 and 50% by weight of the unplasticized polymer. Many techniques for introducing plasticizer compounds to polymer compositions are known in the art, and the invention is not particularly limited as to the method of addition of the polyester oligomers and co-oligomers of the invention into one or more polymer formulations. One or more polyester oligomers or co-oligomers of the invention are employed, in embodiments, as a blend with additional compounds for the preparation of extrudable or moldable polymer compositions. Such additional compounds can include, for example, various inorganic and organic filler compounds, wood dust, reinforcing fibers, colorants, stabilizers, lubricants, anti-microbial additives, and the like.

The polyester polymers and copolymers of the invention are useful as resins in a number of commercially useful applications. By varying the structure of the repeat unit $\delta$ and molecular weight of the polyester polymer or copolymer, varying physical properties of the resulting polymeric product are suitable for making one or more articles, either alone or as a component of a blend with one or more additional materials. Some examples of useful articles include a film, a fiber, a sheet, or a monolithic article; such articles are incorporated into larger items such as adhesives, food packaging films, bottles, caps, blisters, and punnets; bottles, bags and other containers for holding medicaments; construction materials such as flooring tiles, carpeting, window fenestrations, and thermal insulating layers; and woven or nonwoven fabrics such as synthetic fleece.

The thermal and environmental stability of one or more polyester polymers and copolymers of the invention, insofar as they relate to the ketal moieties present in one or more embodiments, is excellent. The polyester polymers and copolyesters of the invention are, in some embodiments, stable in air up to 250° C. In other embodiments, the polyester polymers and copolyesters of the invention are stable in air up to 300° C. In yet other embodiments, the polyester polymers and copolyesters of the invention are stable in air at temperatures in excess of 300° C. The polyester polymers and copolyesters of the invention also have, in embodiments, excellent tensile properties that make them useful for a wide variety of commercial applications as described above.

Polyester Polyisocyanates.

The polyester polyols of the invention are useful, in embodiments, in the formation of polyester polyisocyanates. The polyester polyols that are the precursors to polyester polyisocyanates are any of the polyester polyols described above. The polyester polyols have, in embodiments, at least two hydroxyl moieties per molecule that are capable of reacting with a diisocyanate or higher polyisocyanate to form a polyester polyisocyanate by forming a urethane linkage. Suitable diisocyanates useful in forming one or more polyketal polyisocyanates of the invention include, without limitation, those represented by formula OCN—Z—NCO, in which Z represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms, or a divalent aromatic hydrocarbon group having 6 to 15 carbon atoms.

Non-limiting examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, α,α,α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, 1,5-diisocyanato naphthalene; and mixtures thereof.

Also suitable for making one or more polyester polyisocyanates of the invention are polyisocyanates containing 3 or more isocyanate groups. Nonlimiting examples of suitable polyisocyanates include 4-isocyanatomethyl-1,8-octamethylene diisocyanate, aromatic polyisocyanates such as 4,4',4"-triphenylmethane diisocyanate, and polyphenyl polymethylene polyisocyanates obtained by phosgenating aniline/formaldehyde condensates.

One or more polyester polyisocyanates of the invention are synthesized, in some embodiments, in the form of a polyester polyisocyanate adduct. Suitable polyester polyisocyanate adducts are those containing isocyanurate, uretdione, biuret, urethane, allophanate, carbodiimide and/or oxadiazinetrione groups.

In some embodiments, diisocyanates employed to make one or more polyester polyisocyanates of the invention include the various isomers of diphenylmethane diisocyanate and mixtures thereof, IPDI, 4,4'-dicyclohexyl-methane diisocyanate, and polymeric isocyanates based on diphenylmethane diisocyanate, such as Mondur™ MRS (available from Bayer MaterialScience LLC of Pittsburgh, Pa.).

Methods used to make one or more polyester polyisocyanates of the invention include conventional techniques known in the literature for the synthesis of polyisocyanates from polyols and diisocyanates. A representative technique for making one or more polyester polyisocyanates of the invention is that employed in U.S. Patent Publication No. 2008/0242721, which is incorporated herein by reference in its entirety. The technique of the incorporated Application employs an excess of diisocyanate, as determined by hydroxyl equivalents per mole of polyol, in the presence of dibutyltin dilaurate to give the corresponding polyisocyanate.

One or more polyester polyisocyanates of the invention are useful, in embodiments, for the subsequent synthesis of polyurethanes, polyureas, and poly(urethane ureas), and other related structures as described below.

Polyester Polyurethanes and Related Species.

The various polyester polyols and polyester polyisocyanate structures of the invention described in any of the embodiments above are employed, in embodiments, in the synthesis of polyester polyurethanes, polyester poly(urethane urea)s, and related structures. Polyester polyols as described above are reacted, in some embodiments, with polyisocyanates that are any one of, or a blend of, the polyisocyanates listed above. Whereas a stoichiometric excess of polyisocyanate relative to the polyol results in a polyisocyanate as described above a 1:1 stoichiometric ratio of polyester polyol and diisocyanate results in the formation of a linear polyester polyurethane. The polyisocyanate employed may be difunctional or have higher functionality. Blends of diisocyanates with polyisocyanates having three or more isocyanate moieties are employed in some embodiments to provide a tailored level of branching or crosslinking in the resulting polymeric matrix.

In some embodiments, polyester polyurethanes are formed by the reaction of one or more polyester polyols of the invention with one or more polyester polyisocyanates of the invention. In other embodiments, one or more polyester polyols are reacted with one or more polyisocyanates that are not polyester polyisocyanates. In still other embodiments, one or more polyester polyisocyanates are reacted with one or more polyols that are not polyester polyols; in each embodiment, a different polyurethane product is the result. Useful polyols for such embodiments include both polyketal polyols and any of the polyols listed above. Various other embodiments employing one or more polyester polyols, polyester polyisocyanates, polyols, and polyisocyanates are easily envisioned. Blends of polyisocyanate functional and polyhydroxylated materials are used, in embodiments, to form polyester polyurethanes having a varying range of ketal content and crosslink density and a wide range of available physical properties including glass transition temperature, tensile strength, ductility, and the like.

The reaction of an isocyanate group with an amine is known to form a urea linkage. Thus, in embodiments, one or more polyester polyisocyanates, which already have one urethane linkage per isocyanate group, are reacted with one or more polyamines to form a polyester poly(urethane urea). Suitable polyamines for forming one or more polyester poly(urethane urea)s of the invention include, for example, hydrazine, ethane-1,2-diamine, 1,6-hexanediamine, but-2-ene-1,4-diamine, Metformin, butane-1,4-diamine, propane-1,2-diamine, benzene-1,3-diamine, 2-methylbenzene-1,3-diamine, 4-chlorobenzene-1,3-diamine, methanediamine, 1,3,5-triazine-2,4,6-triamine, N-(2-aminoethyl)ethane-1,2-diamine, N-(6-aminohexyl)hexane-1,6-diamine, N,N'-bis(2-aminoethyl)ethane-1,2-diamine, N-[2-(3-aminopropylamino)ethyl]propane-1,3-diamine, 4-(3,4-diaminophenyl)benzene-1,2-diamine, spermine (N,N'-bis(3-aminopropyl)butane-1,4-diamine), a polyethyleneimine, a polyoxyalkyleneamine having two or more amine groups, such as those sold under the trade name JEFFAMINE®, (available from the Huntsman Corp. of Salt Lake City, Utah), or any diamine or higher amine compound such as those sold under the trade name ELASTAMINE® (available from the Huntsman Corporation).

It is known that an isocyanate can be reacted with water to form a primary amine group and carbon dioxide; the primary amine is then available to react with another isocyanate group to form a urea linkage. Thus, in embodiments, one or more polyester polyisocyanates of the invention are reacted with water to form one or more polyester poly(urethane urea)s via this known pathway. In some such embodiments, the evolution of carbon dioxide acts as a foaming agent as the reaction progresses, thus providing for a foamed polyester poly(urethane urea) matrix. Water reacts with isocyanate groups to create carbon dioxide gas, which fills and expands cells created during the mixing process, and causes the formation of urea groups in a polyurethane reaction. Polyurethane and poly(urethane urea) foams have wide utility in the industry for applications such as automobile cushions, mattress material, furniture cushions, and the like.

The various polyester polyurethanes and polyester poly(urethane urea)s of the invention have a variable range of ketal content and a wide range of physical properties including glass transition temperature, clarity, rigidity and elasticity.

In a particularly useful range of embodiments, polyester polyurethanes or polyester poly(urethane urea)s are present as blocks in a copolymer with other polyurethane or poly(urethane urea) blocks. Such block copolymers are easily achieved by controlling stoichiometry of the reactions to reach the desired residual endgroups, then employing those endgroups as initiation points for an additional polymerization reaction with a different monomer mixture. For example, a polyester diisocyanate of the invention may be reacted with ethylene glycol to form a polyurethane oligomer; the stoichiometry of the reaction is adjusted, using conventional techniques, to result in hydroxyl endgroups. The hydroxyl terminated block is then reacted with toluene diisocyanate to provide a diblock type polyurethane polymer.

Many other embodiments will be readily envisioned; it will be appreciated that the ketal content of the resulting polymer is variable over a range of the described embodiments, and a wide range of physical properties such as glass transition temperature, tensile strength, elasticity, and ductility are attainable in various embodiments of the invention.

The reactions and processes used to form various polyester polyurethanes and polyester poly(urethane urea)s of the invention employ conventional techniques of polyurethane or polyurea synthesis; such techniques typically involve blending the two reagents in a stoichiometry that will result in oligomeric or polymeric molecular weights. In some embodiments where polyurethane linkages are formed, the polymerization reaction is catalyzed. Catalysts useful in polyurethane formation include, in embodiments, tertiary amines. Nonlimiting examples of suitable tertiary amines include dimethylcyclohexylamine, 1,4-diazabicyclo[2.2.2]octane (also called DABCO or TEDA), and bis-(2-dimethylaminoethyl)ether. In other embodiments, organometallic compounds, such as dibutyltin dilaurate, potassium octanoate, or bismuth octanoate may be used to catalyze polyurethane formation. In some embodiments where polyurea linkages are formed, no additional catalyst is required to effect the reaction.

Processes that can be used to make these materials include, in embodiments, reaction injection molding, prepolymerization to a coatable syrup followed by coating and curing, and the like. The various polyester polyurethanes and polyester poly(urethane urea)s of the invention are not particularly limited as to the methods employed in making and processing.

Foamed formulations employing the various polyester polyurethanes and polyester poly(urethane urea)s of the invention are useful embodiments of the invention. Foams are formed during the polymerization reaction, typically by the addition of one or more blowing agents. One example is the use of carbon dioxide evolved in the reaction of isocyanate with water, as described above. In other embodiments, a blowing agent is added to the polymer during processing to facilitate foaming when the polymer is heated, for example in a thermoforming process. Suitable blowing agents include water, certain halocarbons such as HFC-245fa (1,1,1,3,3-pentafluoropropane) and HFC-134a (1,1,1,2-tetrafluoroethane), and hydrocarbons such as n-pentane. In some embodiments, blowing agents are incorporated into e.g. the polyester polyol prior to the polymerization; in other embodiments the blowing agent is added as an auxiliary stream. Halocarbons and hydrocarbons are chosen such that they have boiling points at or near room temperature; these blowing agents volatilize into a gas during the exothermic polymerization reaction. In addition, high density microcellular foams can be formed without the addition of blowing agents by mechanically frothing or nucleating the polyol component prior to use.

In some embodiments, surfactants are employed to modify the characteristics of the foam during the foaming process. In embodiments, they are used to emulsify the liquid components, regulate cell size, and stabilize the cell structure to prevent collapse and surface defects. Rigid foam surfactants produce, in embodiments, very fine cells and very high closed cell content. In other embodiments, flexible foam surfactants stabilize the reaction mass while maximizing open cell content to prevent the foam from shrinking. The need for, and choice of, surfactant is determined, in embodiments, by choice of polyisocyanate, polyol, component compatibility, system reactivity, process conditions and equipment, tooling, part shape, and shot weight.

Various embodiments of the polyester polyurethanes and polyester poly(urethane urea)s of the invention are useful in a broad range of applications. Polyurethane polymers, in general, are compounds of exceptional industrial utility; they find numerous applications because the final properties of the resulting polymer can be influenced greatly through selection of active hydrogen monomers (typically, polyhydroxyl compounds) and isocyanates used, and by selecting the conditions used to prepare the finished polymer products. Polyurethanes are lightweight, strong, durable and resistant to abrasion and corrosion. Depending on choice of monomers, a polyurethane is stiff or flexible. Typically, incorporation of urea type linkages results in a more rigid material. However, with the broad range of monomer chemistry as well as the range of linkages available from ester, urethane, and urea moieties in various embodiments provides extensive flexibility in choice of structure that leads to a broad range of properties and, in turn, applications.

Without providing any particular limitations, the various polyester polyurethanes and polyester poly(urethane urea)s of the invention are useful, in embodiments, as adhesives or sealants, particularly for exterior uses or building construction applications where extremely challenging conditions are encountered; as binders; as coating materials where durability and/or challenging environmental conditions exist; in reactive spray coatings of 100% solids; as elastomers for applications such as rollers and belts for carrying heavy and/or abrasive materials, roller blades, and other footwear parts such as shoe soles; as vibration damping materials; and in the fabrication of medical devices, for example for surface modification, as a protective coating, or within moving parts (e.g. for elastomeric materials). In foamed form, these materials also find utility as insulation materials; low density vibration damping materials; flexible foam for indoor furniture such a seat cushions and mattresses, and other similar applications such as automobile seat cushions.

Polyamides.

The bisketal carboxylates of the invention are useful, in embodiments, for the synthesis of one or more polyamides. Polyamides generally include polymer structures IV and Va wherein Z, Z', or both Z and Z' are NR for each repeat unit S. In some such embodiments, a bisketal carboxylate is reacted with one or more diamines to result in a polyamide of compound IV or Va wherein Z and Z' are NR. In other embodiments, a bisketal carboxylate is polymerized to form the corresponding polyester polymer by reaction with diol as described above; and then the polyester polymer is subsequently reacted with one or more diamines to displace some or all of the diol to result in a polyamide or a hybrid polyester polyamide copolymer. In hybrid polyester polyamide embodiments, some Z and Z' are 0 and some are NR. In still other embodiments, a bisketal carboxylate is reacted with a monofunctional amine to form a bisketal amide, followed by transamidation with a diamine or higher polyamine to result in a polyamide of compounds IV or Va.

Diols, monofunctional amines, aminoalcohols, diacids, diesters, and diamines useful in the synthesis of the polyamides of the invention, and copolymers thereof, include any of those described above.

One useful method for making the polyketal polyamides of the invention is to form a "nylon salt" of the free acid of a bisketal carboxylate with a diamine, followed by heating to form the corresponding polyamide. The method is carried out, in embodiments of the invention, by starting with a bisketal carboxylate having free acid groups. A stoichiometric balance of the bisketal free acid and diamine is achieved by forming the 1:1 ammonium salt in aqueous solution of about 10% to 80%, or about 50%, by weight of the combined compounds in water. Stoichiometry is achieved by controlling the pH of the solution by addition of the bisketal free acid or the diamine. Subsequent concentration of the salt to a slurry of about 60% by weight or greater is then achieved by removing some of the water at a temperature of about 100° C. or greater. Concentration is followed by polymerization by heating the concentrated slurry to about 200° C. or greater, or between about 200° C. and 250° C., or to about 210° C. During the polymerization, the temperature is, in some embodiments, raised to about 260° C. to 300° C., or to about 275° C. In some embodiments, a pressure of about 1.7 MPa or greater is employed during part of all of the polymerization reaction by allowing escape of water. No additional catalyst is required using this method. Notably, in such embodiments, all Z and Z' of compound IV or Va fragments will be NR—only endgroups of the compounds formed using this method will have Z or Z' as O.

In some embodiments, the polyamides of the invention are synthesized via amidolysis. In amidolysis, a bisketal carboxylate is reacted with a diamine to form a polyamide. As with the nylon salt method, in such embodiments, all Z and Z' of IV or Va will be NR—only endgroups of the compounds formed using this method will have Z or Z' as O. Aminolysis is carried out, in some embodiments, by employing one of the techniques known in the literature. For example, methods of reacting of diesters with diamines to form polyamides is described employed in Pryde et al., U.S. Pat. No. 3,223,683; Tashiro et al., U.S. Pat. No. 3,597,376; Brill, U.S. Pat. No. 3,763,234. In embodiments, a bisketal carboxylate and a diamine are contacted in a vessel in amounts that correspond to a 1:1 molar amount of ester to amine groups. The contacted compounds are simply heated to affect the reaction, by allowing for removal of the product alcohol that forms upon reaction of the amines with the ester groups. The compounds are heated to about 200° C., in embodiments between about 200° C. and 250° C., in other embodiments between 250° C. and 300° C., and in still other embodiments to about 300° C. A vacuum is applied, in some embodiments, in order to help drive the reaction to form the polyamide by facilitating removal of the alcohol byproduct of the aminolysis reaction. In some embodiments, an inert solvent is employed to facilitate the reaction; for example, benzene, toluene, xylene, hexane, octane, chlorinated aliphatic hydrocarbons such as 1,1,2-trichloroethane, and the like may be used in various embodiments of the reaction. In some embodiments, for example where the diamine is a liquid at room temperature, it is preferable to employ no solvent.

In some embodiments, a Lewis acid is employed as a catalyst in the aminolysis reaction to form the polyamides of the invention. Examples of suitable Lewis acids include, in embodiments, antimony trichloride, aluminum chloride, antimony trifluoride, ferric chloride, antimony pentachloride, niobium pentachloride, tantalum tetrachloride, titanium tetrachloride, boron trifluoride, antimony pentafluoride, stannic fluoride, aluminum bromide, thallium trichloride, uranyl nitrate, uranium tetrachloride, uranyl acetate, uranium oxides such as $UO_2$, and the like. In embodiments where a Lewis acid catalyst is employed, aminolysis proceeds at temperatures as low as about 250° C., or between about 100° C. and 250° C., or even as low as about 80° C. to 100° C.

In other embodiments, aminolysis is carried out using mild conditions when organic catalysts are employed. For example, Sabot et al., *Tetrahedron Letters* 48 (2007) 3863-6 disclose solvent-free aminolysis of monoesters with monoamines catalyzed by 1,5,7-triazabicyclo[4.4.0]dec-5-ene, or TBD, as low as room temperature. In the reactions of the invention, the addition of heat is required in order to reach appreciable molecular weight, because of the general tendency of polyamides to form high melting, very hard solids even with a low degree of polymerization such as 2-3; raising the temperature allows a higher degree of polymerization to be reached than the same reaction at ambient temperatures.

We have found that a polyamide of the invention is formed, in embodiments, by contacting a bisketal carboxylate with a diamine at molar ratios of about 2:1 to about 1:2, or in some embodiments about 3:2, in other embodiments about 1:1, and in still other embodiments about 1.1:1 to 1.2:1 [bisketal carboxylate]:[diamine]; and adding TBD in an amount of about 200-2000 ppm, or in some embodiments about 750-1000 ppm, based on the mass the combined reagents, to form a reaction mixture. In some embodiments, one or more inert solvents such as toluene, hexane, and the like are added to the reaction mixture; in embodiments, no solvent is added to the reaction mixture. In embodiments, no heat is added to the reaction mixture; in other embodiments, the reaction mixture is heated to a temperature of about 20° C. to 200° C.; in other embodiments, the reaction mixture is heated to a temperature of about 70° C. to 150° C.; in other embodiments, the reaction mixture is heated to a temperature of about 120° C. to 140° C. The reaction of the bisketal carboxylate with the diamine is carried out for about 1 minute to 50 hours, in some embodiments about 1 hour to 45 hours, in other embodiments about 10 to 40 hours, and in still other embodiments about 30 to 40 hours.

In a related embodiment, aminolysis of a polyester polymer is carried out to form the a polyamide of the invention. Polyester polymers useful in one or more aminolysis reactions include any of those structures described above. Aminolysis of polyester polymers is generally carried out according to any of the embodiments of the aminolysis methods described above, for example employing the same catalysts, solvents, and reaction conditions. In embodiments where no solvent is employed to affect the reaction, the polyester polymer is heated to its melt temperature in the presence of a diamine in order to initiate the aminolysis. In such embodiments, no catalyst is required for the reaction to proceed smoothly to high molecular weights. In some such embodiments, application of vacuum during the reaction is useful for removing diol molecules that are the byproduct of the aminolysis of one or more polyester polymers.

The aminolysis reaction between diamines and polyester polymers is, in some embodiments, only a partial aminolysis. In such embodiments, the diamine reacts with the polyester polymer to form a poly(ester amide), e.g. compounds IV or Va wherein Z and/or Z' a mixture of O and NR. How far the aminolysis reaction proceeds to complete the removal of diol and form a polyamide with very few or no fragments wherein Z or Z' is O depends, in embodiments, upon both reaction conditions and stoichiometry of amine to ester functionality. For example, where less than a 1:1 stoichiometric ratio of amine to ester groups are employed in an aminolysis reaction, the reaction proceeds to form a poly(ester amide). Thus, in some embodiments, about 99 mole % to 95 mole % of amine groups are added as compared to ester groups. In other embodiments, about 95 mole % to 80 mole % of amine groups are added as compared to ester groups. In still other embodiments, as low as 50% of amine groups are added compared to ester groups. In general, as the mole % of amine groups are lowered relative to ester groups, the glass transition temperature of the resulting poly(ester amide) is observed to become lower. Thus, glass transition temperatures of the poly(ester amide)s of the invention are targeted based on the desired end use.

In some embodiments, the polyamides of the invention are synthesized by transamidation. For example, in some embodiments, a polyamide of the invention is synthesized employing one of the above-described methods; the polyamide is then subjected to transamidation with a second diamine using techniques described, for example, in Stahl et al., U.S. Pat. No. 7,154,004 to arrive at a polyamide having one or more fragments attributable to the second diamine. In other embodiments, a bisketal carboxylate is reacted with a monofunctional amine, such as any of those listed above, to form a bisketal amide; the bisketal amide is then subjected to transamidation with a diamine to result in a polyamide of the invention. In embodiments, a metal catalyst based on Sc, Ti, or Al is employed to catalyze the transamidation reaction. In some embodiments, the catalyst employed is $Sc(OTf)_3$; in other embodiments, $Ti(NMe_2)_4$ or $Al_2(NMe_2)_6$ are used. The reactions are preferably carried out at temperatures of about 250° C. or less. An inert solvent, such as toluene, is employed in some embodiments; in other embodiments, no solvent is employed to affect the transamidation reaction.

It will be appreciated that copolymers of the polyamides of the invention are easily obtained using one or more variations of the methods described above. For example, in one embodiment, a mixture of bisketal carboxylates is reacted with a diamine to form a copolymer; in another embodiment, a bisketal carboxylate is mixed with a non-ketal based diester or diacid and copolymerized with a diamine. In yet another embodiment, a bisketal carboxylate is reacted with an aminoalcohol to form a hydroxyl functionalized amide, which is reacted with a diol to result in a poly (ester amide). Many other embodiments are easily envisioned. It will also be appreciated that certain methods of chain extension, such as reacting amino endgroups of a polyamide of the invention with a diisocyanate, are also available as an extension of any of the synthetic methodology and the unique polyamide and poly(ester amide) structures of the invention to increase molecular weight, or otherwise effect the physical properties of the poly(ester amide)s and polyamides of the invention. Additional functionality and increase in molecular weight of the poly(ester amide)s and polyamides are also realized, in embodiments, by providing acrylate, allyl, or oxirane functionalities that in turn can be polymerized to provide chain extension, crosslinking, or branching. It will further be appreciated that crosslinked or branched analogs of the polyamides of the invention are readily formed by employing a minor proportion of, for example, a trifunctional, or higher polyfunctional, ester, acid, or amide or a triamine or higher polyamine in any of the methods described above to form a polyamide of the invention. The trifunctional or higher ester is, in some such embodiments, a trisketal compound, such as one of the trisketal carboxylates of the invention.

The polyamides of the invention, synthesized using the various methods described above, have a degree of polymerization of about 2 to 500, or about 10 to 200, or about 10 to 100 depending on choice of reagents, stoichiometry, and methodology employed. In some embodiments, polyamides having a molecular weight of about 2000 to 10,000 g/mol have a polydispersity index (the ratio of weight average molecular weight to number average molecular weight) of about 1 to 3. In other embodiments, the polydispersity index is about 1.7 to 1.8.

The polyamides of the invention have unique and useful properties that enable their use in a wide range of applications. In various embodiments, the polamides of the invention have good transparency, high levels of stiffness, high levels of hardness, good creep resistance, good dimensional stability, little processing shrinkage, good heat distortion properties, high melt viscosity, high melt strength, ability to alloy with other polyamides that are amorphous or semicrystalline to achieve a wide additional range of properties, low water uptake, good surface properties, good barrier properties, resistance to nonpolar solvents, good impact strength, ductility at moderate temperatures, good weatherability, and stress-crack resistance to polar solvents.

Polyester Polycarbonates.

The polyester polyols of the invention are useful, in embodiments, for the synthesis of polyester polycarbonates. Polyester polycarbonates employ, in embodiments, one or more polyester polyols of the invention; they further incorporate one or more acyclic or cyclic dialkyl carbonate monomers or another source of carbonate bond such as potassium carbonate or phosgene.

Polyester polycarbonate synthesis is carried out, in embodiments, by employing any known and conventional technique for making polycarbonates. One such technique employs phosgene. For example, in one such embodiment, a polyester polyol is treated with sodium hydroxide, followed by an interfacial reaction between the sodium alkoxide of the bisketal diol and phosgene. Alternatively, one or more polyester polycarbonates of the invention are synthesized, in embodiments, by transesterification with a polyester polyol of a difunctional carbonate having the general structure

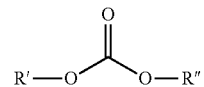

where R' and R" are the same or different and are, in embodiments, a linear, cyclic, or branched alkyl, alkenyl, or alkynyl group; an aralkyl group, or an aromatic group; or R' and R" together with the carbonate bond forms, in some embodiments, a cyclic carbonate. In embodiments where R' and R" together with the carbonate bond forms a cyclic carbonate, a polyester polycarbonate is formed by a ring opening reaction initiated by the polyester polyol.

The polyester polycarbonates of the invention have a range of available properties due to the broad range of polyester polyols of the invention that are available as starting materials. Polycarbonates are known to be tough, transparent, thermally stable materials suitable for a range of engineering plastics applications. Suitable applications for one or more polyester polycarbonates of the invention include, but are not limited to, fabrication of items requiring molding, laminating, thermoforming such as extruding or coextruding, or machining or other conventional means of working. Examples of useful items include compact discs, riot shields, baby bottles and other water/drink bottles and food containers, electrical components, automobile headlamps, as a component of a safety glass laminate, eyeglass lenses, safety helmets, and the like.

Various polyester polycarbonates of the invention do not employ Bisphenol A (4,4'-dihydroxy-2,2-diphenylpropane), the most commonly employed polycarbonate polyol starting material. Bisphenol A has been the subject of toxicity concerns since the 1930s, particularly in food or drink contact applications (e.g., baby bottles, water/drink bottles, food containers). One or more polyester polycarbonates of the invention are, in one or more embodiments, are useful for food or drink applications where it is desirable to eliminate Bisphenol A.

Additionally, polyester polycarbonates of the invention are, in some embodiments, biodegradable. Biodegradable polycarbonates are useful for one or more applications, for example, in food or drink contact applications, to enable disposable embodiments of various containers. Other applications where biodegradability is advantageous include disposable medical supplies such as eye shields and the like. In one or more embodiments, the polyester polycarbonates of the invention advantageously supply the desirable properties of polycarbonates and additionally supply biodegradability thereof.

In some embodiments, polyester polycarbonates of the invention, when terminated by hydroxyl endgroups, are suitable as diols for use in polyurethane synthesis. Polyester polycarbonate diols are synthesized, in some embodiments, by employing polyester polyols in the synthesis of a polyester polycarbonate and controlling stoichiometry of the polymerization in order to provide hydroxyl functionality at the ends of the polyester polycarbonate. In other embodiments, a polyester polycarbonate is transesterified at each end with a diol to provide hydroxyl endgroup. Polyester polycarbonates having hydroxyl endgroups are reacted, in embodiments, with one or more diisocyanates to form a polyester poly(carbonate urethane). Polyester poly(carbonate urethane)s are synthesized using, in some embodiments, the techniques described above to make polyester polyurethanes. In other embodiments, techniques used to form the polyester poly(carbonate urethane)s of the invention are those outlined in Moore et al., *Novel Co-Polymer Polycarbonate Diols for Polyurethane Elastomer Applications*, Proceedings of the Polyurethanes Expo 2003, Oct. 1-3, 2003 (© 2003, American Chemistry Council).

Polyester Diacrylates.

Polyester polyols of the invention are useful, in embodiments, for the synthesis of diacrylate adducts thereof. As used herein, the term "acrylic functionality" or "acrylate" is intended to collectively mean an acrylate, methacrylate, or other similar moiety that is capable of subsequent polymerization or crosslinking reactions utilizing a free radical or redox mechanism. The acrylate adducts of the polyester polyols of the invention are termed "polyester diacrylates." Acrylic functionality is imparted, in embodiments, to one or more of the polyester polyols of the invention by employing conventional techniques for the reaction of alkanols to form acrylates and methacrylates. Any of the materials and synthetic methods employed for compounds Tb are usefully employed for the polyester polyols of the invention to form one or more polyester diacrylates. In one or more embodiments, the polyester diacrylates are useful as crosslinkers in one or more formulations, usually in conjunction with one or more monoacrylate or vinyl species as described above.

Allyl Adducts.

Bisketal carboxylates and polyester polyisocyanates are useful, in embodiments, for the synthesis of diallyl adducts thereof. As used herein, the term "allyl" or "allyl functionality" means a —$CH_2$—CH=$CH_2$ moiety that is capable of subsequent polymerization or crosslinking reaction utilizing a free radical or redox mechanism.

Allyl alcohol is employed, in embodiments, to synthesize allyl esters of bisketal carboxylates by esterification or transesterification reaction using any of the known techniques commonly employed in the literature. For example, in embodiments where $R^1$ is hydrogen, the free bisketal carboxylic acid is esterified with allyl alcohol in the presence of an organic sulfonic acid esterification catalyst and a polymerization inhibitor, as described in U.S. Pat. No. 2,249,768. In other embodiments, allyl alcohol is employed in a transesterification reaction of the ester moieties of the bisketal carboxylates. Suitable methods of transesterification to form allyl esters of any of the bisketal carboxylates of the invention are disclosed in Remme et al., *Synlett* 2007, 3, 491-3 and U.S. Pat. No. 5,710,316; other suitable methods are disclosed in Singh et al., *J. Org. Chem.* 2004, 69, 209-12 and Chavan et al., *Synthesis* 2003, 17, 2695-8. Allyl monohalides are also employed, in embodiments, to synthesize one or more allyl esters of the bisketal carboxylates by employing a bisketal carboxylate and a catalyst that is palladium halide or platinum halide, a technique employed in, for example, U.S. Pat. No. 3,699,155. These and other methods are used, in embodiments, to synthesize allylic esters of the bisketal carboxylates of the invention.

In other embodiments, allyl alcohol is reacted with one or more polyester polyisocyanates of the invention to give the corresponding allyl polyester urethane adducts, using techniques commonly employed to react an alcohol with an isocyanate group.

One or more allyl functional bisketal carboxylates or allyl polyester urethanes are, in embodiments, polymerized using any of the techniques known in the literature. For example, heating allyl functional compounds in the presence of thermal free-radical initiators gives polymeric products. Typically, allyl polymers are made by charging the allyl functional monomer and a free-radical initiator to a reactor, and heating the mixture at a temperature effective to polymerize the monomer (see, e.g. "*Kirk-Othmer Encyclopedia of Chemical Technology*," 4$^{th}$ ed., Volume 2, pp. 161-179). Improved methods of polymerizing allyl compounds are also usefully employed with one or more allylic bisketal carboxylates or allyl polyester urethanes of the invention. For example, U.S. Pat. No. 5,420,216 discloses that gradual addition of initiator is key to high conversion in allyl polymerization.

In some embodiments of the invention, one allyl group per molecule provides sufficient reactivity to result in high conversion or high molecular weight of the radically polymerized product. In other embodiments, two allyl groups per molecule yields solid, high molecular weight polymers by initiation with a suitable free-radical catalyst. Such embodiments are useful to provide, for example, heat-resistant cast sheets and thermoset moldings. In some such embodiments, the reactivity of compounds having more than one allyl group permits polymerization in two stages: a solid prepolymer containing reactive double bonds is molded by heating; then completion of polymerization gives cross-linked articles of superior heat resistance. In embodiments, the relatively slow rate of polymerizations is controlled more readily than in the polymerization of polyfunctional vinyl compounds to give soluble prepolymers containing reactive double bonds.

One useful embodiment of one or more allylic bisketal carboxylates or allyl polyester urethanes of the invention employs minor proportions of one or more allylic bisketal carboxylates or allyl polyester urethanes for cross-linking or curing preformed vinyl-type polymers. Among the preformed polymers cured by minor additions of allyl ester monomers and catalysts followed by heat or irradiation are polyethylene, PVC, and acrylonitrile-butadiene-styrene (ABS) copolymers. These reactions are examples of graft copolymerization in which specific added peroxides or high energy radiation achieves optimum cross-linking. In other embodiments, small proportions of allylic bisketal carboxylates or allyl polyester urethanes are added as regulators or modifiers of vinyl polymerization for controlling molecular weight and polymer properties. In yet other embodiments, allylic bisketal carboxylates or allyl polyester urethanes of high boiling point and compatibility are employed as stabilizers against oxidative degradation and heat discoloration of polymers.

In embodiments where the allylic bisketal carboxylates or allyl polyester urethanes are employed to form thermoset materials, one useful application is for moldings and coatings for electronic devices requiring high reliability under long-term adverse environmental conditions. These devices include electrical connectors and insulators in communication, computer, and aerospace systems. Other embodiments are readily envisioned.

Epoxy Adducts.

Bisketal carboxylates and polyester polyisocyanates, and polyester polyols are useful, in embodiments, for the synthesis of epoxy or glycidyl adducts thereof. As used herein, the term "epoxy" means an oxirane moiety, and "glycidyl" means a methyl oxirane moiety. Both epoxy and glycidyl moieties are capable, in embodiments, of subsequent polymerization or crosslinking reactions utilizing a ring opening reaction. Glycidyl adducts are glycidyl esters of bisketal carboxylates or glycidyl functionalized adducts of bisketal carboxylates having one or more glycidyl functionalities.

Glycidyl alcohol is employed, in some embodiments, to synthesize glycidyl esters of bisketal carboxylates by esterification or transesterification reaction using any of the known techniques commonly employed in the literature. For example, Chanda, M. and Roy, S., eds., *Plastics Technology Handbook*, 4th ed., © 2007 Taylor & Francis Group, LLC, pp. 4-114 to 4-116; and U.S. Pat. No. 5,536,855 describe some of the methods that are useful, in embodiments, to react one or more bisketal carboxylates with glycidyl alcohol. In other embodiments, glycidyl alcohol is reacted with one or more polyester polyisocyanates of the invention to give the corresponding glycidyl adducts, using techniques commonly employed to react an alcohol with an isocyanate group.

In other embodiments, an epihalohydrin such as epichlorohydrin is used to impart glycidyl ether functionality one or more polyester polyols of the invention. The reaction between an alcohol and epichlorohydrin to form a glycidyl ether is known in the literature. For example, the reaction of the alcohol Bisphenol A with epichlorohydrin is a well known reaction by which epoxy resins are formed. A similar process is used in some embodiments of the invention to form one or more glycidyl adducts from one or more polyester polyols. For example, U.S. Pat. No. 5,420,312 describes techniques of forming glycidyl ethers of alcohols. This and other conventional techniques employed to react epichlorohydrin with an alcohol are, in embodiments, employed using the polyester polyols of the invention to form glycidyl ethers of the polyester polyols. Epichlorohydrin is also, in embodiments, reacted directly with carboxylic acids to form the corresponding glycidyl ester; the reaction involves ring opening of the glycidyl moiety, followed by dehydrochlorination to re-form the oxirane ring. In embodiments, glycidyl esters of one or more bisketal carboxylates of the invention are formed by reacting a bisketal carboxylate having one or more free carboxylic acid groups with one or more equivalents of epichlorohydrin. Such a reaction is carried out, in one or more embodiments, by employing the techniques of Bukowska, et al., *J. Chem. Tech. and Biotech.*, 74: 1145-1148 (1999); Otera et al., Synthesis (12), 1019-1020 (1986); U.S. Pat. Nos. 3,576, 827; British Patent No. GB 884,033; and German Patent Appl. No. DE 15945/70; or by other techniques found in the literature. In still other embodiments, the ionic salts of the bisketal carboxylates are reacted with an epihalohydrin, such as epichlorohydrin, to form the corresponding glycidyl esters. In such embodiments, the techniques employed by, for example, Maerker et al., J. Org. Chem. 26, 2681-2688 (1961) are useful, among other techniques.

Another technique employed, in some embodiments, to provide glycidyl or epoxy functionality to one or more bisketal carboxylates is to react an unsaturated bisketal ester with a peroxide. For example, U.S. Pat. No. 5,036,154 discloses a method whereby an ethylenically unsaturated ester group, such as an allyl ester, is reacted with hydrogen peroxide in the presence of an alkali metal or alkaline earth metal salt of tungstic acid, phosphoric acid, and a phase transfer catalyst to give the epoxidized product of the unsaturated moiety. Such a technique is used, in embodiments, to form a glycidyl adduct of a bisketal carboxylate of the invention from the corresponding allyl adduct, the allyl adducts of bisketal carboxylates having been described above. Other techniques employed in the literature are similarly useful to obtain one or more epoxidized products of allyl esters of the invention. For example, esterification of a bisketal carboxylate with an unsaturated fatty acid ester is followed, in embodiments, by reacting the unsaturated site with hydrogen peroxide, as is described by Du et al., *J. Am. Org. Chem. Soc.* 81(4) 477-480 (2004).

One or more glycidyl or epoxy adducts of the invention are, in embodiments, subsequently polymerized using standard techniques from the literature. The polymerization of epoxy groups, for example with amines, amides, or anhydrides, is widely known. A useful summary of compounds and mechanisms of curing epoxy groups is found in Chanda, M. and Roy, S., eds., *Plastics Technology Handbook*, 4th ed., © 2007 Taylor & Francis Group, LLC, pp. 4-116 to 4-122. Any of the techniques employed or referenced therein are used, in various embodiments, to polymerize the epoxy groups present on one or more polyketal glycidyl esters of the invention to form the corresponding linear or crosslinked polymer.

Applications of epoxy polymers are numerous and broad in scope. Due to their high strength, variable crosslink density, and variable chemical starting materials, epoxies have found broad applicability for numerous applications. Many of the most common applications are set forth in Chanda, M. and Roy, S., eds., *Plastics Technology Handbook*, 4th ed., © 2007 Taylor & Francis Group, LLC, pp. 2-80 to 2-81, 7-26, and 4-124 to 4-125. The epoxy resins formed by curing the epoxy functional polyketal carboxylates of the invention are, in various embodiments, useful in one or more of these applications.

Embodiments Of Compounds II and III

Compounds II.

The following embodiments employ the bisketal functionality of compounds II as, or to make, one or more surfactants, solvents, stabilizers, or plasticizers. One embodiment of a reaction scheme is shown below:

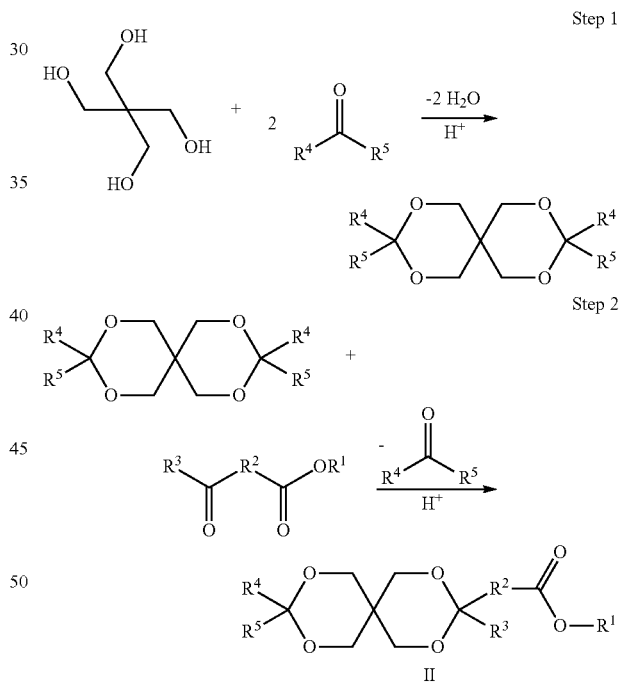

wherein $R^1$, $R^2$, $R^3$, $R^4$, and $R^5$ are as defined above. In some alternative embodiments of the reaction to form compounds II, an acyclic ketal of the ketone $R^6R^7C=O$ may be used in the first step of the reaction. For example, where the ketone to be employed in the first step is acetone, 2,2-dimethoxypropane may be used in its place. In such embodiments, methanol is displaced instead of water. In some such embodiments, the ease of removing of methanol is advantageous; this is particularly true where large scale reaction processes are employed, as the use of an acyclic ketal as a starting material instead of a ketone ameliorates the problem of removing water and issues with residual water in the system. In other embodiments, it is advantageous to use the ketone and displace water, as water need not be stored or disposed of, and is not flammable or combustible.

Where $R^1$ is a cation, for example a sodium, lithium, ammonium, or alkylammonium cation, compound II is, in one or more embodiments, a surfactant or an additive for one or more aqueous formulations. Cation functionality is typically imparted to the compounds II after the second step of the synthesis, employing standard saponification methods widely employed in the industry and readily found in the literature. Divalent or polyvalent cations, for example calcium, barium, or magnesium cations, are also used, in some embodiments, to functionalize compounds II to form ionic dimer species. In one or more ionic dimer embodiments, compounds II are stabilizers for one or more polymeric compositions that are subjected to high temperatures, such as are encountered in thermal processing.

In some embodiments $R^1$ is an alkyl group having less than six carbon atoms. In one or more such embodiments compounds I are solvents, for example coalescing solvents for polymeric dispersions, emulsions, or plastisols; or solvents for one or more organic compounds; or solvents for removal of compounds and coating formulations from surfaces, e.g. paint, varnish, and the like. In other embodiments $R^1$ is an alkyl group having six or more carbon atoms. In one or more such embodiments compounds II are plasticizers, for example, in one or more polymer formulations or plastisols. In other embodiments, $R^3$, $R^4$, $R^5$, or a combination thereof are alkyl groups having less than six carbons. In one or more such embodiments compounds II are solvents, for example coalescing solvents for polymeric dispersions, emulsions, or plastisols; or solvents for one or more organic compounds; or solvents for removal of compounds from surfaces e.g. paint, varnish, and the like. In other embodiments, $R^3$, $R^4$, $R^5$, or a combination thereof are alkyl groups having more than six carbons. In one or more such embodiments compounds II are plasticizers, for example, in one or more polymer formulations or plastisols.

The compounds II are employed, in embodiments, in a subsequent reaction to form one or more amide functional compounds. Reaction of the ketal carboxylate moieties of compounds II with primary or secondary amines results in displacement of the ester moiety to form the corresponding ketal amide moiety. Any of the standard techniques known in the art to form amides from esters may be employed in the synthesis of amides of compound II. Amides of compound II are useful as surfactants in one or more applications. In some such embodiments, the amine employed to form the amide is a primary amine having six or less carbons. In some such embodiments, the amine employed has an hydroxyl or other heteroatomic moiety, such as, for example, ethanolamine or diethanolamine.

Other variations on the compounds II are obtained by varying the nature of the oxocarboxylate employed, thereby varying $R^2$ and $R^3$.

Compositionally, the examples cited above serve to highlight the advantageous nature of hybrid ketals of compound II compared to conventional pentaerythritol compounds, namely, the combinatorial nature of the various compositions that are achieved. The hydrophobic/lipophobic character of compounds II is easily tailored by choice of ketone and oxocarboxylate, rendering the resulting compounds II compatible with a broad range of formulations either as a major component or a minor component or rendering them suitable for one or more other applications, for example use as a solvent to remove paints, varnishes, or other coatings from one or more surfaces. Further, the combinatorial compositions chosen are achieved with ease employing simple, straightforward chemical transformations using standard laboratory equipment.

In embodiments, compounds II are advantageously employed as plasticizers. Many commercially useful polymers, such as poly(vinyl chloride) (PVC) are usefully blended with plasticizers to lower the glass transition temperature for various applications; however, compounds with free hydroxyl groups are generally not compatible. The compounds II, with substantially no free hydroxyl groups, are thus compatible with such polymers and the formulations and articles that employ them.

The hybrid ketals of the invention encompass a combinatorial chemical group of compounds. In some embodiments of the invention, compounds II are useful to make one or more surfactants, solvents, stabilizers, or plasticizers by virtue of the combinatorial feature of the structures available. Some examples include the following:

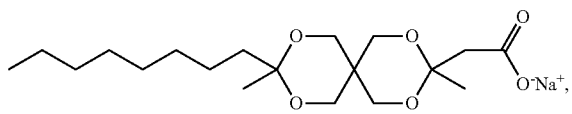

formed, in embodiments, by the reaction of pentaerythritol with two equivalents of an alkyl acetoacetate, followed by displacement of one equivalent of alkyl acetoacetate with one equivalent of decan-2-one and subsequent treatment of the hybrid ketal with a base, such as sodium hydroxide;

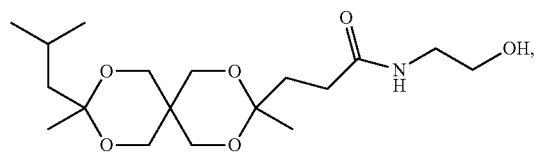 [SMILES: CC(C)CC1(C)OCC2(COC(C)(CCC(=O)NCCO)OC2)CO1]

formed by the reaction of pentaerythritol with two equivalents of MIBK, followed by displacement of one equivalent of MIBK with one equivalent of alkyl levulinate, and subsequent reaction of the methyl ester with ethanolamine; and

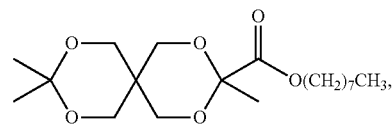

formed by the reaction of pentaerythritol with two equivalents of acetone, followed by displacement of one equivalent of acetone with one equivalent of octyl pyruvate, or another alkyl pyruvate with subsequent transesterification of the ester with 1-octanol.

Compounds III.

In various embodiments, the compounds III are hybrid ketals are analogous to compounds II. Thus, for example,

III

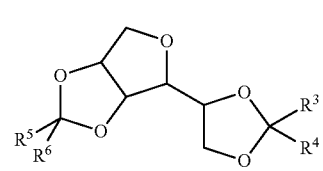

wherein one of $R^3$ and $R^5$ is isobutyl and the other is

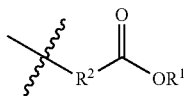

compounds III is, in various embodiments, a hybrid ketal. Thus, the salts, lower alkyl esters, amides, and other reactive and combinatorial features attributed to compounds II, as well as applications of the various analogs of compounds II, apply with equal force to compounds III.

Oxo-Polycarboxylate Ketals of Compounds I, II, and III

One embodiment of the invention is the class of ketal carboxylates formed from transketalization of any pentaerythritol dialkyl ketal, compound IIIa, compound IIb, or any of compounds

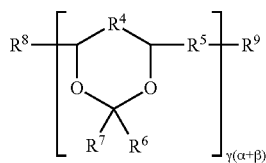

with an oxo-polycarboxylate, such as an oxo-dicarboxylate or an oxo-tricarboxylate, to give the corresponding mono-polycarboxylate ketal. For example, transketalization of the trisacetonide of sorbitol with one equivalent of diethyl-4-oxopimelate results in the bisalkyl ketal of sorbitol having two ester moieties on one ketal ring:

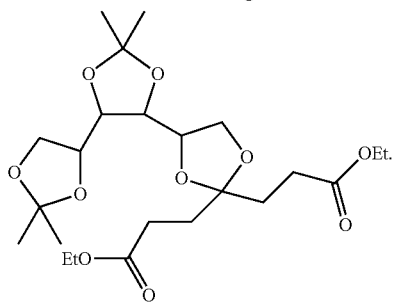

The various embodiments of the invention employing oxo-polycarboxylate ketals encompass a combinatorial scheme of compounds and uses thereof. Some of these embodiments are represented by the following structures.

One embodiment of the invention is a class of compounds having structure VIa:

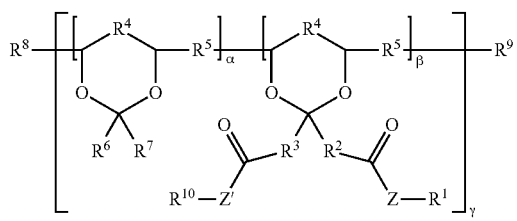

wherein
$R^1$ and $R^{10}$ are independently hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ and $R^{10}$ are the same or different for each occurrence;

$R^2$ and $R^3$ are independently covalent bonds or linear or branched alkyl groups optionally containing one or more heteroatoms;

$R^4$ is a covalent bond, methylene, or alkylmethylene, wherein a covalent bond indicates a 5-membered ring and a methylene or alkylmethylene indicates a 6-membered ring, and $R^4$ is the same or different for each occurrence;

$R^5$ is a covalent bond, methylene, ethylene, hydroxymethylene, oxygen, —$CH_2$—O—$CH_2$—, or a polymeric moiety, and $R^5$ is the same or different for each occurrence;

$R^6$ and $R^7$ are independently linear, branched, or cyclic alkyl groups;

$R^8$ and $R^9$ are independently hydrogen, a linear, branched, or cyclic alkyl, a linear, branched, or cyclic alkenyl, alkynyl, aryl, alkaryl, or a polymeric moiety and optionally contain one or more heteroatoms;

Z and Z' are independently O or NR wherein R is hydrogen or an alkyl group having six or less carbons and can optionally contain one or more heteroatoms;

$\gamma$ is an integer of at least 1; and $\alpha$ and $\beta$ are independently 0 or 1 for each $\gamma$.

Another embodiment of the invention is the class of compounds having structure VIb:

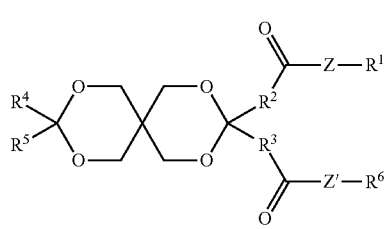

wherein
$R^1$ and $R^6$ are independently hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms;

$R^2$ and $R^3$ are independently covalent bonds or linear or branched alkyl groups optionally containing one or more heteroatoms;

$R^4$ and $R^5$ are independently linear, branched, or cyclic alkyl groups; and

Z and Z' are independently O or NR wherein R is hydrogen or an alkyl group having one to six carbon atoms and can optionally contain one or more heteroatoms.

Another embodiment of the invention is the class of compounds having structures VIc or VId

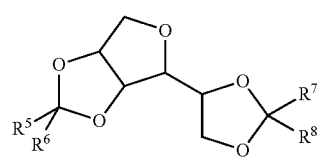

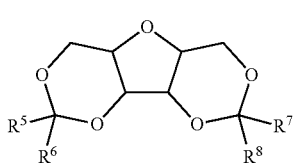

wherein, for both VIc and VId,
one of $R^5$ and $R^7$ is isobutyl or

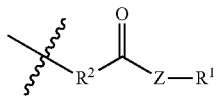

wherein $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety and optionally contains one or more heteroatoms, $R^2$ is a covalent bond or a linear or branched alkyl group and optionally contains one or more heteroatoms, and Z is O or NR wherein R is hydrogen or an alkyl group having one to six carbon atoms and can optionally contain one or more heteroatoms;

and one of $R^6$ and $R^8$ is methyl or

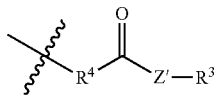

wherein $R^3$ is hydrogen, a metal cation, an organic cation, a linear, branched, or cyclic alkyl, a linear, branched, or cyclic alkenyl, alkynyl, aryl, alkaryl, or an oligomeric or polymeric moiety and optionally contains one or more heteroatoms, $R^4$ is a covalent bond or a linear or branched alkyl group and optionally contains one or more heteroatoms, and Z' is O or NR wherein R is hydrogen or an alkyl group having one to six carbon atoms and can optionally contain one or more heteroatoms;

provided that if $R^5$ is isobutyl then $R^6$ is methyl, and if $R^7$ is isobutyl then $R^8$ is methyl.

Another embodiment of the invention is the class of compounds having one or more repeat units with structure VIe

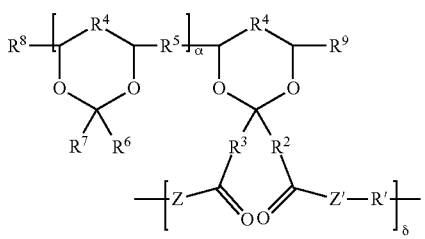

wherein
$R^1$ is a divalent linear, branched, or cyclic alkyl, a linear, branched, or cyclic alkenyl, alkynyl, aryl, or alkaryl moiety; and optionally contains one or more heteroatoms;

$R^2$ and $R^3$ are independently covalent bonds or linear or branched alkyl groups optionally containing one or more heteroatoms;

$R^4$ is a covalent bond, methylene, or alkylmethylene, wherein a covalent bond indicates a 5-membered ring and a methylene or alkylmethylene indicates a 6-membered ring, and $R^4$ is the same or different for each occurrence;

$R^5$ is a covalent bond, methylene, ethylene, hydroxymethylene, oxygen, —$CH_2$—O—$CH_2$—, or a polymeric moiety, and $R^5$ is the same or different for each occurrence;

$R^6$ and $R^7$ are independently linear, branched, or cyclic alkyl groups;

$R^8$ and $R^9$ are independently hydrogen, a linear, branched, or cyclic alkyl, a linear, branched, or cyclic alkenyl, alkynyl, aryl, alkaryl, or a polymeric moiety and optionally contain one or more heteroatoms;

Z and Z' are independently O or NR wherein R is hydrogen or an alkyl group having six or less carbons and can optionally contain one or more heteroatoms;

α is an integer of at least 1 and defines a ketal unit, wherein α ketal units are disposed contiguously to $R^5$, $R^8$, or $R^9$, or a combination thereof; and δ is an integer of at least 1.

Another embodiment of the invention is the class of compounds having one or more repeat units with structure VIf

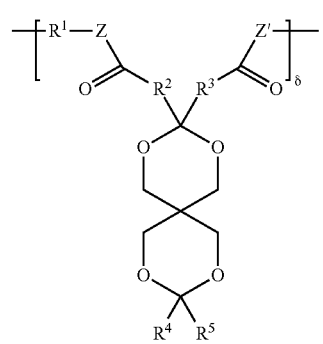

wherein
$R^1$ is a divalent linear, branched, or cyclic alkyl, a linear, branched, or cyclic alkenyl, alkynyl, aryl, or alkaryl moiety; and optionally contains one or more heteroatoms;

$R^2$ and $R^3$ are independently covalent bonds or linear or branched alkyl groups optionally containing one or more heteroatoms;

$R^4$ and $R^5$ are independently linear, branched, or cyclic alkyl groups;

Z and Z' are independently O or NR wherein R is hydrogen or an alkyl group having one to six carbon atoms and can optionally contain one or more heteroatoms; and.

δ is an integer of at least 1.

Another embodiment of the invention is the class of compounds having one or more repeat units with structure VIg, VIh, or VIi, or a combination thereof.

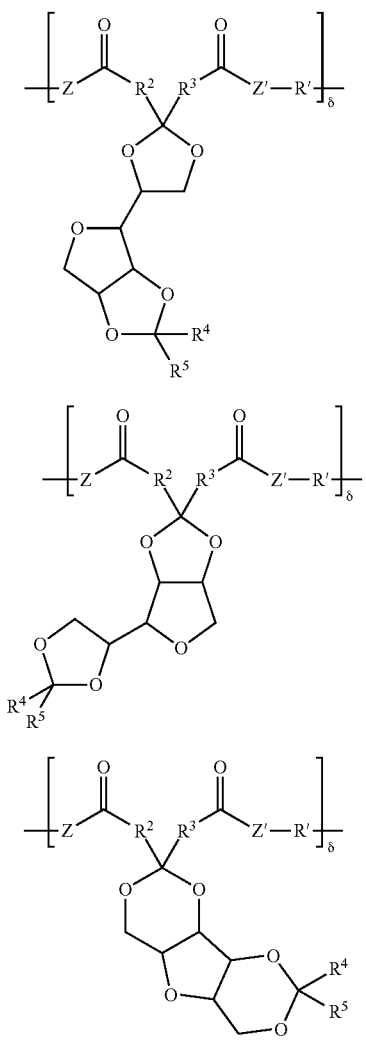

wherein, for all VIg, VIII, and VIi,
R¹ is a divalent linear, branched, or cyclic alkyl, a linear, branched, or cyclic alkenyl, alkynyl, aryl, or alkaryl moiety; and optionally contains one or more heteroatoms;
R² and R³ are independently covalent bonds or linear or branched alkyl groups optionally containing one or more heteroatoms;
R⁴ and R⁵ are independently linear, branched, or cyclic alkyl groups;
Z and Z' are independently O or NR wherein R is hydrogen or an alkyl group having one to six carbon atoms and can optionally contain one or more heteroatoms; and.
δ is an integer of at least 1.

In all of the above embodiments of compounds VI, heteroatoms that are contained in one or more R groups include, in some embodiments, O, N, S, Cl, Br, I, or. F; in some such embodiments, O may be contained as an oxo moiety. Compound VIa is analogous to previously described compounds I or Ia and the various embodiments described for compounds I and Ia apply to compounds VIa. Compound VIb is analogous to previously described compounds II and the various embodiments described for compounds II apply to compounds VIb. Compounds VIc are analogous to previously described compounds IIIa and the various embodiments described for compounds IIIa apply to compounds VIc. Compounds VId are analogous to previously described compounds IIIb and the various embodiments described for compounds IIIb apply to compounds VId. Compounds VIe are analogous to previously described compounds IV and the various embodiments described for compounds IV apply to compounds VIe. Compounds VIf are polymers synthesized from compound VIb and, as such, are analogous to compounds IV in terms of various embodiments of polymer composition and uses thereof; thus, the various embodiments described for compounds N apply to compounds VIf. Compounds VIg and VIh are analogous to previously described compounds Va and the various embodiments described for compounds Va apply to compounds VIg and VIh. Compounds VII are analogous to previously described compounds Vb and the various embodiments described for compounds Vb apply to compounds VIi.

Suitable examples of oxodicarboxylates that are employed to make the compounds VIa to VII include, for example, 2-oxopropanedioic acid, 2-oxobutanedioic acid, 2-oxopentanedioic acid, 2-oxohexanedioic acid, 4-oxoheptanedioic acid (4-oxopimelic acid), 4-oxodecandioic acid, 4-oxopyran-2,6-dicarboxylic acid, 2-hydroxy-4-oxohepta-2,5-dienedioate, and the like, and esters thereof. Suitable oxotricarboxylates include N-succinyl-2-amino-6-ketopimelic acid or an ester thereof. The methods used to make such monoketal dicarboxylates are, in embodiments, the same as those described above to make compounds I, II, and III. Compounds VIa-VIg, as well as their corresponding salts, transesterified products, and amides, are analogous to the above described structures I-V and are employed in similar formulations, applications, and articles. Thus, in embodiments that are analogous to the polymers W and V above, the polymers of monoketal dicarboxylates are polyesters, copolyesters, polyamides, poly(ester amide)s, copolyamides, polyisocyanates, polyurethanes, polyureas, poly(ester urethanes); or acrylates, allylic esters, or epoxy capped materials or their polymerized analogs.

Additionally, analogs wherein oxo-tricarboxylates are employed, and polymers wherein more than one oxo-polycarboxylate ketal is present per monomer entity, are also envisioned as embodiments of the invention.

The following Examples further elucidate and describe the compounds of the invention and applications thereof without limiting the scope thereof.

EXPERIMENTAL SECTION

General Procedures

Gas Chromatography (GC) and GC-Mass Spectrometry (GC-MS) Analyses

GC (GC-FID) and GC-MS analyses are carried out according to standard laboratory techniques. Standard GC analysis is carried out by flame ionization detector (FID). The integration peak areas of all peaks in the chromatogram are automatically calculated by an Agilent Technologies ChemStation (Agilent Technologies of Santa Clara, Calif.). The calculated peak areas are reported as a weighted percent (expressed as abundance) relative to the area of all of the detected peaks in the chromatogram (total area). These calculations are used elsewhere herein to report all percent yield, percent yield "based on theoretical", percent yield "as determined by GC-MS", and any other percent reaction statements resulting from GC or GC-MS analyses.

Gel Permeation Chromatography (GPC)

Molecular weight determination is carried out by GPC using a Waters Isocratic HPLC System (from Waters Corp. of Milford, Mass.) that includes a Waters 2414 Differential Refractometer, Waters 1515 Isocratic Pump, Waters 717 Autosampler, and Waters Column Heater and Empower GPC Software for molecular weight analysis. For samples with an expected molecular weight of 20,000-400,000 Daltons a PLgel Mixed D 5 μm column, 300×7.5 mm, is used; for samples with an expected molecular weight of less than 20,000 a PLgel Mixed E 5 μm column, 300×7.5 mm, is used; and for samples with an expected molecular weight between 20,000 and 2,000,000 a PLgel Mixed C 5 μm column, 300× 7.5 mm is used. All columns were obtained from Polymer Labs, a division of Varian Inc. of Palo Alto, Calif.

All samples were analyzed using either tetrahydrofuran (THF) or dimethyl formamide (DMF) mobile phase. The THF mobile phase is employed at 1 ml/min and weight average molecular weight ($M_w$) is calculated against polystyrene narrow molecular weight standards. The DMF mobile phase with 0.05M lithium bromide is employed at 1 ml/min and weight average molecular weight ($M_w$) is calculated against polymethylmethacrylate narrow molecular weight standards.

Differential Scanning Calorimetry (DSC)

Glass transition temperature is determined by DSC following ASTM D-3418 and employing a TA Q200 instrument with refrigerated cooling and TA Thermal Advantage software (from TA Instruments of New Castle, Del.). Homogeneous samples of between about 5 and 15 mg are prepared, weighed, placed in a Tzero pan and crimped with a Tzero lid, (pan and lid both available from TA Instruments). The mass of the sample is entered into the Thermal Advantage software. The thermal analysis is carried out according to one of the three sets of parameters below:

Parameter Set 1
Cycle 0: Equilibrate at −80° C.
Isotherm for 2.00 minutes
End of Cycle 0
Cycle 1: Ramp 10° C./min to 150° C.
Isotherm for 2.00 minutes
End of Cycle 1
Cycle 2: Ramp 10° C./min to −80° C.
Isotherm for 2.00 minutes
End of Cycle 2
Cycle 3: Ramp 10° C./min to 150° C.
Isotherm for 2.00 minutes
End of Cycle 3
Repeat at Cycle 0
Parameter Set 2
Cycle 0: Equilibrate at −150° C.
Isotherm for 5.00 minutes
End of Cycle 0
Cycle 1: Ramp 10° C./min to 150° C.
Isotherm for 5.00 minutes
End of Cycle 1
Cycle 2: Ramp 10° C./min to −150° C.
Isotherm for 5.00 minutes
End of Cycle 2
Cycle 3: Ramp 10° C./min to 150° C.
Isotherm for 5.00 minutes
End of Cycle 3
Repeat at Cycle 0
Parameter Set 3
Cycle 0: Equilibrate at −40° C.
Isotherm for 2.00 minutes
End of Cycle 0
Cycle 1: Ramp 10° C./min to 240° C.
Isotherm for 2.00 minutes
End of Cycle 1
Cycle 2: Ramp 10° C./min to −40° C.
Isotherm for 2.00 minutes
End of Cycle 2
Cycle 3: Ramp 10° C./min to 240° C.
Isotherm for 2.00 minutes
End of Cycle 3
Repeat at Cycle 0

Examples 1-3

Ketalization of Sorbitol Using 2,2-Dimethoxypropane and Para-Toluene Sulfonic Acid

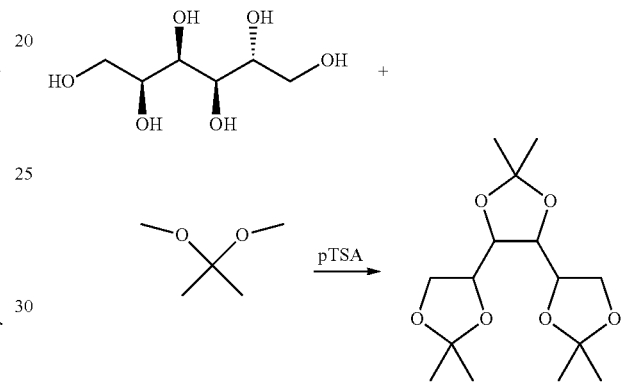

To a 2 L round bottom flask was added D-sorbitol (199.49 g, 1.1 mol, obtained from Acros Organics of Geel, Belgium), 2,2-dimethoxypropane (DMP) (628.48 g, 6.0 mol, obtained from the Sigma-Aldrich Company of St. Louis, Mo.), and para-toluene sulfonic acid (pTSA) (0.413 g, approximately 500 ppm based on total weight of reactants, obtained from the Sigma-Aldrich Company of St. Louis, Mo.). The flask was placed on a rotary evaporator, and the oil bath set to 70° C. The flask immersed in the oil bath and rotated at this temperature for approximately 5 hours and 20 minutes and then removed from the oil bath and cooled to room temperature. A magnetic stir bar was added to the flask along with 150 mesh activated basic $Al_2O_3$ (about 75 g, or about 10% wt. based on mass of reagents, obtained from the Sigma-Aldrich Company of St. Louis, Mo.). The mixture was stirred for approximately 1 hour, and then the $Al_2O_3$ removed by vacuum filtration on a sintered glass funnel. The crude mixture was then placed on the rotary evaporator and immersed in the oil bath set to 80° C. and the DMP was stripped by applying a vacuum of approximately 20 Torr during heating and rotation. The reaction product was then distilled into a bump flask on the rotary evaporator by setting the temperature of the oil bath to 153° C., and employing pressure of about 4-6 Torr. The recovered product was observed to form a while, crystalline appearing product as it cooled.

This same reaction was repeated using $H_2SO_4$ (98%, obtained from Fisher Scientific of Waltham, Mass.), and Amberlyst® 15 sulfonated resin (obtained from the Sigma-Aldrich Company of St. Louis, Mo.) alternative acid catalysts. The $H_2SO_4$ was neutralized in an identical manner to the pTSA, while the Amberlyst 15 was neutralized simply by filtering off the solid catalyst. The reaction conditions are shown in Table 1.

TABLE 1

Reaction variables for synthesis of the trisacetonide of sorbitol.

| Example No. | Sorbitol (mols) | DMP (mols) | pTSA (ppm) | Amberlyst 15 Resin (ppm) | $H_2SO_4$ (ppm) | Reaction Time (hrs.) |
|---|---|---|---|---|---|---|
| 1 | 199.49 g (1.1 mol) | 628.48 g (6.0 mol) | about 500 ppm | — | — | about 5.33 |
| 2 | 252.26 g (1.38 mol) | 793.23 g (7.62 mol) | — | about 1400 ppm | — | about 3 |
| 3 | 250.23 g (1.37 mol) | 751.24 g (7.21 mol) | — | — | about 675 ppm | about 2 |

Example 4

Ketalization of Sorbitol with 2-Butanone (Methyl Ethyl Ketone, MEK)

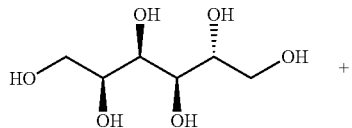

+

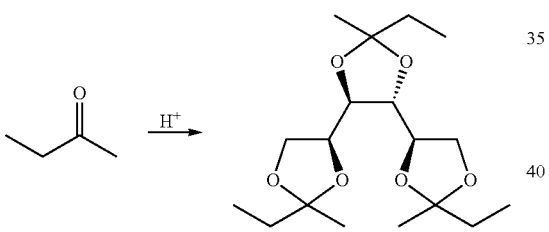

To a 500 mL 3-neck flask equipped with a magnetic stir bar and a Soxhlet extractor topped with a condenser and a nitrogen inlet/outlet were added D-sorbitol (55.40 g, 0.30 mol, obtained from the Sigma-Aldrich Company of St. Louis, Mo.), 2-butanone (MEK) (136.45 g, 1.89 mol, obtained from the Sigma-Aldrich Company of St. Louis, Mo.), and 98% $H_2SO_4$ (7.8 µL, about 75 ppm based on total weight of the reagents, obtained from Fisher Scientific of Waltham, Mass.). The Soxhlet extractor was filled with activated 3 Å molecular sieves and then partially filled with MEK. The flask was heated to reflux under nitrogen. After approximately 9.5 hours at reflux, the flask was cooled to room temperature. In order to neutralize the contents of the flask, approximately 150 mesh activated, basic $Al_2O_3$ (about 19 g, or 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The MEK was stripped on a rotary evaporator.

Figure 2:
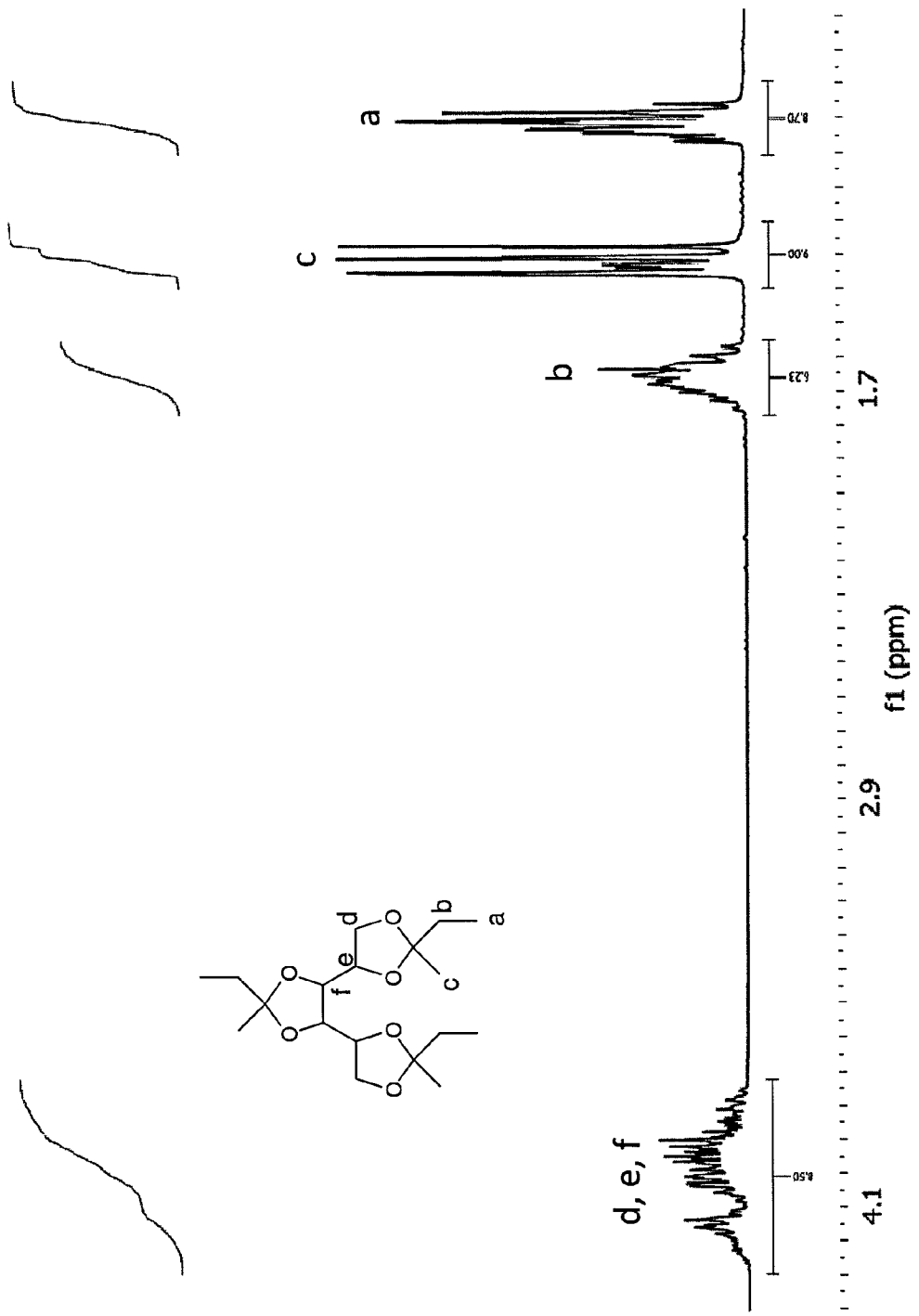
FIG. 2 shows a $^1$H NMR plot of a compound of the invention.

The final product was found to be >97.5% pure by GC-FID, and was recovered at about 85% yield by weight. An NMR (300 MHz, $CDCl_3$ solvent, TMS reference) of this mixture was obtained; the NMR plot is shown in FIG. 2.

Example 5

Ketalization of Sorbitol with 2-Butanone (Methylethyl Ketone, MEK) Using Hexane

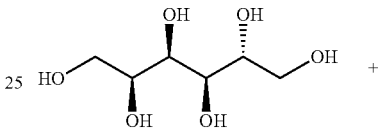

+

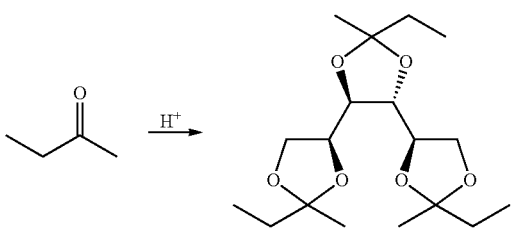

To a 1 L 3-neck round bottom flask equipped with a magnetic stir bar and a Dean Stark trap topped with a condenser and a nitrogen inlet, was added D-sorbitol (109.54 g, 0.60 mol, obtained from the Sigma-Aldrich Company of St. Louis, Mo.), methyl ethyl ketone (MEK, 260.92 g, 3.62 mol, obtained from the Sigma-Aldrich Company of St. Louis, Mo.), 98% $H_2SO_4$ (15.1 µL, 75 ppm based on total weight of reagents, obtained from the Sigma-Aldrich Company of St. Louis, Mo.), and hexane (16 mL, 0.12 mol, obtained from the Sigma-Aldrich Company of St. Louis, Mo.). The Dean Stark was filled with additional MEK and the system placed in an oil bath, and placed under a nitrogen blanket. The oil bath was heated to allow the reaction mixture to reflux. As the reaction progressed, water was observed collecting in the bottom of the Dean Stark trap suggesting that the hexane was forming an azeotrope with the water and hexane, and then causing the water and MEK to separate. After about 16 hours of refluxing, water was no longer collecting in the Dean Stark. The reaction was cooled to room temperature. Approximately 150 mesh activated, basic $Al_2O_3$ (about 37 g, or 10 wt. %) was added to the flask and stirred for approximately 1 hour. The $Al_2O_3$ was removed by vacuum filtration over a sintered glass funnel. The MEK was stripped on a rotary evaporator. The final product was found to be about 98.8% pure by GC-FID and was recovered at about a 91% yield by weight.

Example 6

Ketalization of Sorbitol with 4-Methyl-2-Pentanone (Methyl Isobutyl Ketone, MIBK)

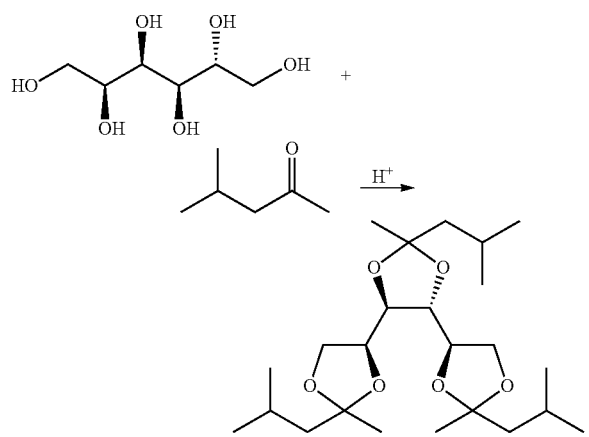

To a 2 L 4-neck round bottom flask equipped with a Dean Stark trap and a magnetic stirrer, was added D-sorbitol (151.58 g, 0.83 mol, obtained from the Sigma-Aldrich Company of St. Louis, Mo.), methyl isobutyl ketone (MIBK, 542.47 g, 5.42 mol, obtained from the Sigma-Aldrich Company of St. Louis, Mo.), and 98% $H_2SO_4$ (28.3 µL, 75 ppm based on total weight of reagents, obtained from Fisher Scientific of Waltham, Mass.). The Dean Stark trap was filled with additional MIBK, and the system placed in a heating mantle, and placed under nitrogen blanket. The heating mantle was heated to allow the reaction mixture to reflux. Reaction progress was monitored by the amount of water collected in the Dean Stark trap based on the principle that water and MIBK form a self-separating azeotrope at 88° C. After approximately 23 hours of refluxing, only 88% of the theoretical amount of water had been collected, but since the water level had remained constant for over 2 hours, the heat was shut off and the flask cooled to room temperature.

Approximately 150 mesh activated, basic $Al_2O_3$ (about 50 g, or 10 wt. %) was added to the flask and stirred for approximately 1 hour. The $Al_2O_3$ was removed by vacuum filtration over a sintered glass funnel. The crude reaction mixture was analyzed by GC-MS to determine the percentage and structure of the reaction products; amounts are reported in percent by GC. The mixture was found to contain the desired tris-ketal product (34%), as well as unreacted MIBK (54.7%), and two side products corresponding to cyclic ethers containing the two ketals (7.3% and 2.2% respectively) shown below:

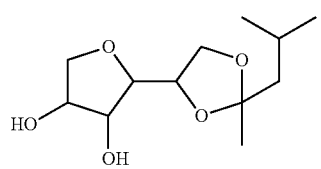

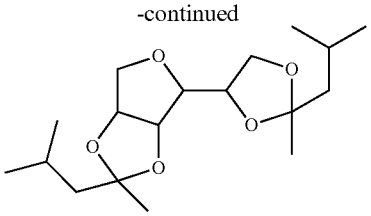

The excess MIBK was removed by rotary evaporation. The evaporated mixture was blended with 300 mL of hexane, to which approximately 200 mL of distilled water was added, and the two layers mixed thoroughly. The hexane layer was saved, and the hexane removed by rotary evaporation to result in a final mixture. The final mixture was analyzed by GC-MS and found to contain <1% MIBK and about 90% of the desired tris-ketal. This mixture was recovered at 61.4 mole % yield based on starting sorbitol. An NMR (300 MHz, $CDCl_3$ solvent, TMS reference) of this mixture was obtained.

Example 7

Ketalization of Mannitol with Methylisobutyl Ketone (MIBK) Using $H_2SO_4$

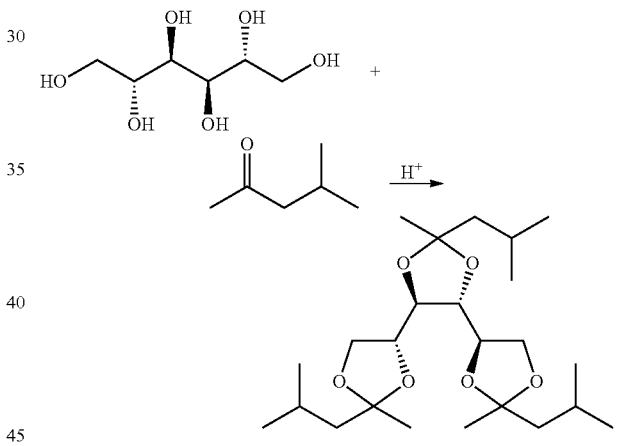

To a 500 mL 3-neck round bottom flask equipped with a magnetic stir bar and a Dean Stark trap topped with a condenser and a nitrogen inlet/outlet were added D-mannitol (25.48 g, 0.14 mol, obtained from the Sigma-Aldrich Company of St. Louis, Mo.), MIBK (104.91 g, 1.05 mol, obtained from the Sigma-Aldrich Company of St. Louis, Mo.), and 98% $H_2SO_4$ (5.3 µL, about 75 ppm based on total weight of reagents, obtained from Fisher Scientific of Waltham, Mass.). The Dean Stark trap was filled with excess MIBK and the system placed under nitrogen. The flask was placed in a heating mantle, and the mantle set to allow the mixture to reflux. The reaction was monitored by the amount of water present in the Dean Stark trap resulting from the separation of a water/MIBK azeotrope that is formed as the reaction progresses. The reaction was refluxed for approximately 15 hours, at which point the theoretical amount of water was present, so the heat was shut off.

In order to neutralize the acidity, approximately 150 mesh activated, basic $Al_2O_3$ (about 13 g, or 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The unreacted MIBK was removed using a rotary evaporator. A sample of the crude mixture was analyzed by GC-MS and showed that the only detectable product was the desired trisketal. No side products were observed. A GC-FID of this clear liquid showed that it was greater than 96% pure, so no further purification was required. The product was recovered with a 87% yield by weight based on mannitol.

Example 8

Ketalization of Erythritol with 2,2-Dimethoxypropane (DMP) and p-Toluene Sulfonic Acid

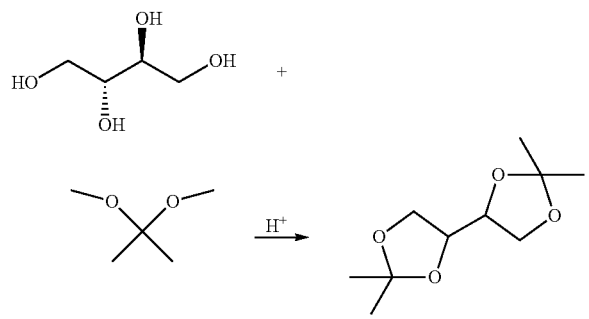

To a 500 mL 3-neck round bottom flask equipped with a nitrogen inlet/outlet leading to a mineral oil bubbler were added erythritol (69.38 g, 0.57 mol, obtained from Cargill Inc. of Minnetonka, Minn.), 2,2-dimethoxypropane (DMP, 239.65 g, 2.3 mol, obtained from the Sigma-Aldrich Company of St. Louis, Mo.), and para-toluene sulfonic acid (0.540 g, 2.8 mmol, obtained from the Sigma-Aldrich Company of St. Louis, Mo.). The system was placed under a slow stream of nitrogen, and the flask placed in an oil bath. The oil bath was heated to 70° C., and maintained for approximately 2.5 hours. After removing the flask from the oil bath, approximately 150 mesh activated, basic Al$_2$O$_3$ (about 31 g, or 10 wt. %, obtained from the Sigma-Aldrich Company of St. Louis, Mo.) was added to the flask and stirred for approximately 1 hour. The Al$_2$O$_3$ was removed by vacuum filtration over a sintered glass funnel. The unreacted DMP was stripped using a rotary evaporator with an oil bath temperature of 70° C., and a pressure of about 70 Torr. The product was then distilled using a rotary evaporator with a bath temperature of 106° C., and a pressure of approximately 10 Torr. The resulting product was observed to form a white solid upon cooling. This product was analyzed by GC-FID and found to be approximately 98.1% pure.

Example 9

Ketalization of Erythritol with Methylisobutyl Ketone Using H$_2$SO$_4$

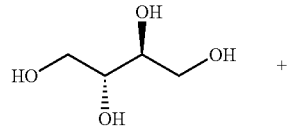

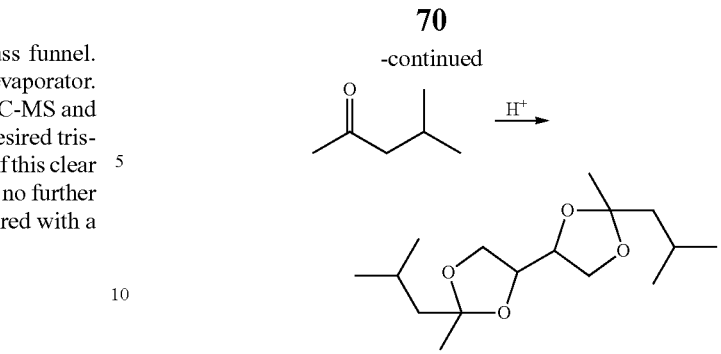

To a 500 mL 3-neck round bottom flask equipped with a magnetic stir bar and a Dean Stark trap topped with a condenser and a nitrogen inlet/outlet were added Erythritol (50.66 g, 0.42 mol, obtained from Cargill Inc. of Minnetonka, Minn.), methyl isobutyl ketone (MIBK, 186.22 g, 1.86 mol, obtained from the Sigma-Aldrich Company of St. Louis, Mo.), and 98% H$_2$SO$_4$ (12.9 μL, about 100 ppm by weight, obtained from Fisher Scientific of Waltham, Mass.). The Dean Stark trap was filled with excess MIBK, and the system placed under a nitrogen blanket. The flask was placed in an oil bath, and the oil bath temperature set to 165° C. The reaction was monitored by the amount of water collected in the Dean Stark trap given that water and MIBK form an azeotrope at 88° C. that subsequently separated into the two distinct layers. The reaction was cooled to ambient temperature after approximately 16 hours of refluxing when the theoretical amount of water had been collected. In order to neutralize the acidity, 150 mesh activated, basic Al$_2$O$_3$ (about 23 g, or 10 wt. %, obtained from the Sigma-Aldrich Company of St. Louis, Mo.) was added to the flask and stirred for approximately 1 hour. The Al$_2$O$_3$ was removed by vacuum filtration over a sintered glass funnel. The unreacted MIBK was stripped on the rotary evaporator using a pressure of approximately 7 Torr, and sufficient heat to remove the excess MIBK. The resulting product was a clear liquid which was found to be greater than 97% pure by GC-FID, and gave a yield of about 91% based on theoretical mole percent yield. An NMR was obtained of the liquid (300 MHz, CDCl$_3$ solvent, TMS reference) and confirmed the identity of product.

Example 10

Ketalization of Diglycerol with Methyl Isobutyl Ketone Using H$_2$SO$_4$

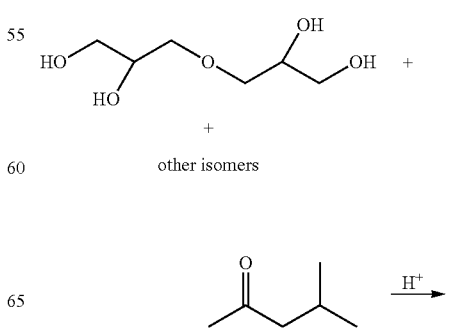

-continued

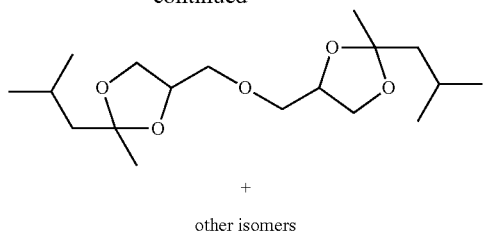

+ other isomers

To a 250 mL 3-neck round bottom flask equipped with a magnetic stir bar and a Dean Stark trap topped with a condenser and a nitrogen inlet/outlet were added diglycerol (27.07 g, 0.163 mol, obtained from TCI America of Portland, Oreg.), methyl isobutyl ketone (MIBK, 57.15 g, 0.571 mol, obtained from Sigma-Aldrich Company of St. Louis, Mo.), and 98% $H_2SO_4$ (3.4 µL, about 75 ppm based on total weight of reagents, obtained from Fisher Scientific of Waltham, Mass.). The diglycerol was analyzed by NMR to try to determine the purity of sample given the multiple possible isomers. The sample was found to contain about 90% of one isomer, and about 10% of the minor isomers. The major isomer is identified below as well as two possible structures of the minor isomers.

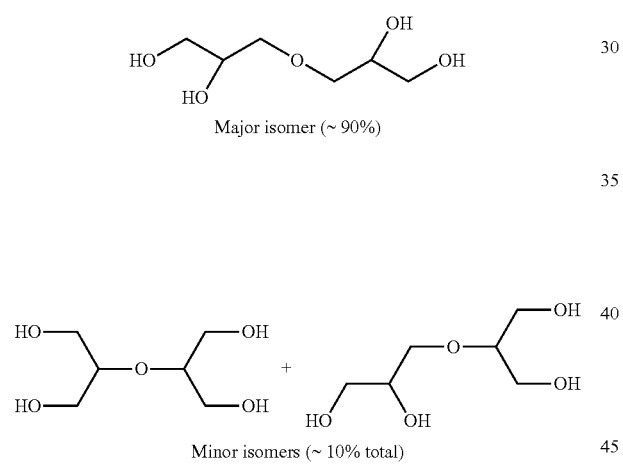

The Dean Stark trap was filled with MIBK, and the system placed under nitrogen. The flask was placed in a heating mantle and heated to reflux. The reaction was monitored by the amount of water collected in the Dean Stark trap given that water and MIBK form an azeotrope at 88° C. that subsequently separated into the two distinct layers. The reaction was stopped after about 5.5 hours of refluxing when the theoretical amount of water had been collected. Then 150 mesh activated, basic $Al_2O_3$ (about 8 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The unreacted MIBK was stripped on the rotary evaporator using a pressure of approximately 7 Torr, and sufficient heat to remove the excess MIBK. The oil bath was then set to 180° C. to remove any impurities (i.e. mono-ketal). After a small amount of liquid had collected in the bump flask the rotary evaporator was shut off. The undistilled liquid was analyzed and found to contain >96% of the desired products (91% 5-membered ketal ring, 9% minor isomer ketal rings) by GC-FID, and was recovered with about a 76% yield.

Example 11

Transketalization of Sorbitol Tris-Acetonide with Ethyl Levulinate Using pTSA

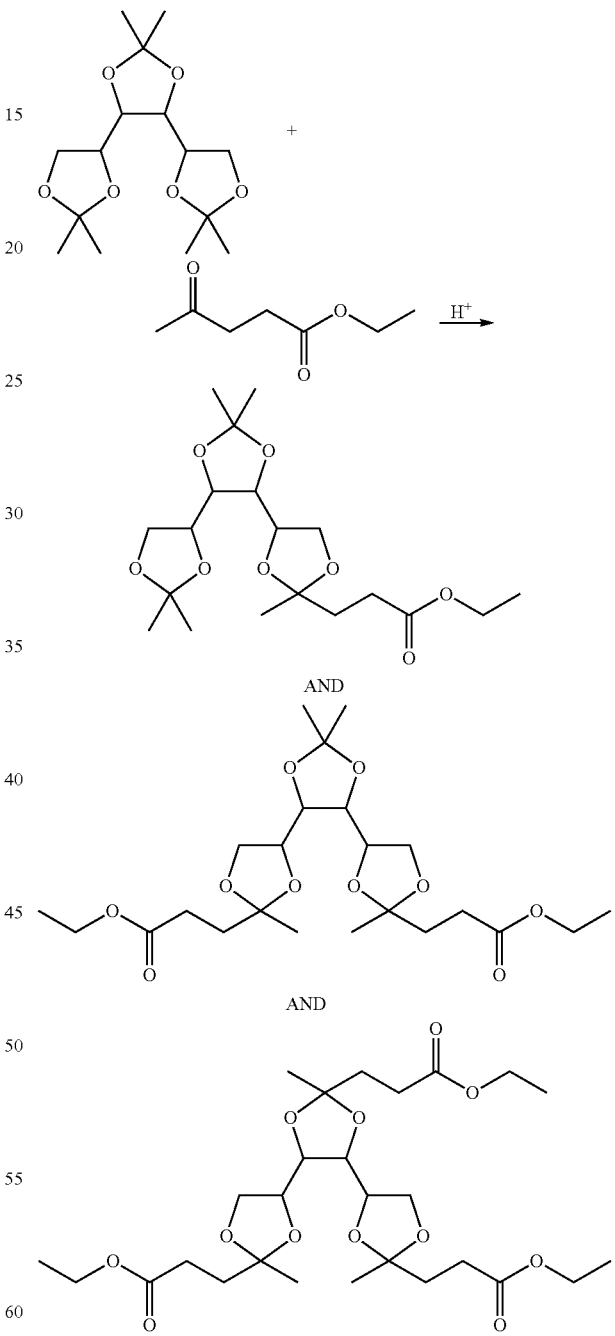

To a 250 mL 3-neck round bottom flask equipped with a magnetic stir bar, a Dean Stark trap topped with a condenser, and a nitrogen inlet/outlet were added sorbitol tris-acetonide synthesized according to the procedure of Example 1 ("STA", 20.14 g, 66.7 mmol), ethyl levulinate (19.51 g, 135 mmol, obtained from the Langfang Triple Well Chemicals Company, Ltd. of Langfang City, HeBei, China), and para-toluene sulfonic acid (pTSA) (0.0633 g, about 1600 ppm based on weight of reagents, obtained from the Sigma-Aldrich Company of St. Louis, Mo.). The flask was degassed/backfilled with nitrogen 3 times down to a pressure of about 15 Torr. The flask was placed in an oil bath and the system placed under nitrogen blanket. The oil bath was heated to 50° C. and maintained for 3.5 hours. An additional amount of pTSA (0.0624 g, about 1600 ppm based on weight of reagents, obtained from the Sigma-Aldrich Company of St. Louis, Mo.) was added to the flask. After another 18 hours, the pressure in the flask was reduced to 100 Torr, and maintained for about 1.75 hours. The pressure was then further reduced to about 50 Torr and maintained for about 4 hours. The flask was then backfilled with nitrogen and cooled to room temperature.

Then 150 mesh activated, basic $Al_2O_3$ (about 3.8 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The composition of the reaction was determined at various points using GC-MS to track the extent of transketalization between the acetonide ketals and the ethyl levulinate. The results of the tracking are shown in Table 2.

conditions were maintained for approximately 6 hours, and then the flask backfilled with nitrogen and cooled to room temperature.

The reaction mixture was analyzed by GC-FID and found to contain: about 24.5% ethyl levulinate, about 11.7% tris-acetonide ketal of sorbitol (0 exchanges), about 29.8% bis-acetonide, mono-levulinate ketal of sorbitol (1 exchange), about 26.9% mono-acetonide, bis-levulinate ketal of sorbitol (2 exchanges), about 5.8% tris-levulinate ketal of sorbitol (3 exchanges).

Example 13

Separation of Products of the Crude Reaction Mixture of Example 11

The crude reaction mixture of Example 11 was analyzed by GC-FID and found to contain about 21% ethyl levulinate,

TABLE 2

Progress of transketalization reaction of Example 11.

| Time (hrs.) | Temp (° C.) | Pressure (torr) | % STA (no exchange) | % mono-Lev. (1 exchange) | % bis-Lev. (2 exchanges) | % tris-Lev. (3 exchanges) | % Et-Lev. |
|---|---|---|---|---|---|---|---|
| 0.75 | 50 | atm. | 45.3 | 22.4 | 1.7 | 0 | 27.1 |
| 1.33 | 50 | atm. | 41.8 | 29.9 | 3.5 | 0 | 21.9 |
| 2 | 50 | atm. | 34.8 | 35.5 | 6.0 | 0 | 20.5 |
| 3.5 | 50 | atm. | 26.5 | 42.1 | 11.8 | 0 | 16.5 |
| 4.5 | 50 | atm. | 20.2 | 43.8 | 18.0 | 0 | 14.3 |
| 5.33 | 50 | atm. | 18.6 | 44.7 | 20.4 | 0 | 13.4 |
| 19 | 50 | atm. | 15.0 | 43.8 | 26.2 | 0 | 11.7 |
| 21.33 | 50 | atm. | 15.1 | 44.7 | 25.6 | 0 | 12.0 |
| 21.83 | 50 | 100 | 13.9 | 44.9 | 27.5 | 0.4 | 10.6 |
| 24.66 | 50 | 50 | 7.7 | 40.7 | 40.3 | 0.8 | 7.9 |
| 25.5 | 50 | 50 | 6.7 | 36.7 | 44.1 | 1.3 | 7.9 |
| 27.16 | 50 | 50 | 4.4 | 33.1 | 51.0 | 1.7 | 6.3 |

Example 12

Transketalization of Sorbitol Tris-Acetonide with Ethyl Levulinate Using Amberlyst 15 Sulfonated Resin To a 1 L 3-neck round bottom flask equipped with a magnetic stir bar and a Dean Stark trap topped with a condenser and a nitrogen inlet/outlet were added sorbitol tris-acetonide obtained using the method from Example 3 (151.05 g, 0.499 mol), ethyl levulinate (151.23 g, 1.05 mol, obtained from the Langfang Triple Well Chemicals Company, Ltd. Of Langfang City, HeBei, China), and activated AMBERLYST® 15 sulfonated resin (0.75 g, about 2500 ppm based on weight of reagents, obtained from the Sigma-Aldrich Company of St. Louis, Mo.). The system was degassed/backfilled with nitrogen a total of 5 times down to a pressure of about 25 Torr. The system was left under nitrogen, and the flask placed in an oil bath. The oil bath was heated to 50° C., and after 30 minutes the pressure in the flask was reduced to about 50 Torr. These about 6.1% sorbitol tris-acetonide, about 32.9% mono-ethyl levulinate, bis-acetonide ketal of sorbitol (Et-MLSK), about 37.6% bis-ethyl levulinate, mono-acetonide ketal of sorbitol (Et-BLSK), and about 0.9% tris-ethyl levulinate ketal of sorbitol (Et-TLSK). The crude reaction mixture was placed in a 500 mL roundbottom flask which was then mounted on a rotary evaporator with a bump flask. Oil bath temperature and vacuum were controlled in order to distill off various fractions, which were analyzed by GC-FID. Ethyl levulinate was removed using a pressure of approximately 2-8 Torr and an oil bath temperature of approximately 110-120° C. Sorbitol tris-acetonide and Et-MLSK were removed in two fractions using pressure of ranging between 300-1000 mTorr, and an oil bath temperature ranging between about 180-210° C. Then Et-BLSK was distilled using a pressure of approximately 250-300 mTorr, and an oil bath temperature of approximately 205°-215° C. The distilled Et-BLSK was found to be about 97.5% pure by GC, with the largest identifiable impurity being Et-TLSK which was present at about 0.5%.

Example 14

Polymerization of Mono-Acetonide, Bis-Levulinate Ketal of Sorbitol with 1,6-Hexamethylene-Diamine

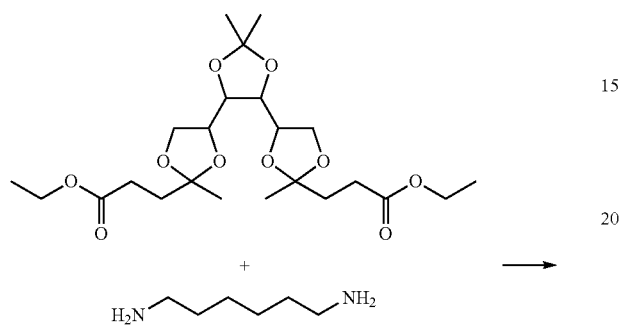

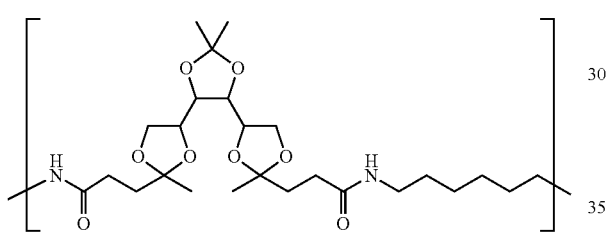

To a 250 mL 3-neck round bottom flask equipped with a mechanical stirrer and a Dean Stark trap topped with a condenser and a nitrogen inlet were added bis-ethyl levulinate, mono-acetonide ketal of sorbitol (Et-BLSK), synthesized according to the procedure of Example 12 and purified according to the procedure of Example 13 (19.42 g, 40.9 mmol), and 1,6-diaminohexane (4.80 g, 41.3 mmol, obtained from Acros Organics of Geel, Belgium). The system was degassed/backfilled with nitrogen 5 times down to a pressure of approximately 20 Torr. The flask was placed in an oil bath and heated to 180° C. After 17.5 hours, the temperature was increased to 210° C. and maintained for 1 hour. The pressure in the flask was reduced to approximately 9 Torr and maintained for 30 minutes. The pressure in the flask was then further reduced to approximately 150 mTorr. After 6.5 hours at these conditions, the flask was backfilled with nitrogen and cooled to room temperature.

Figure 3:
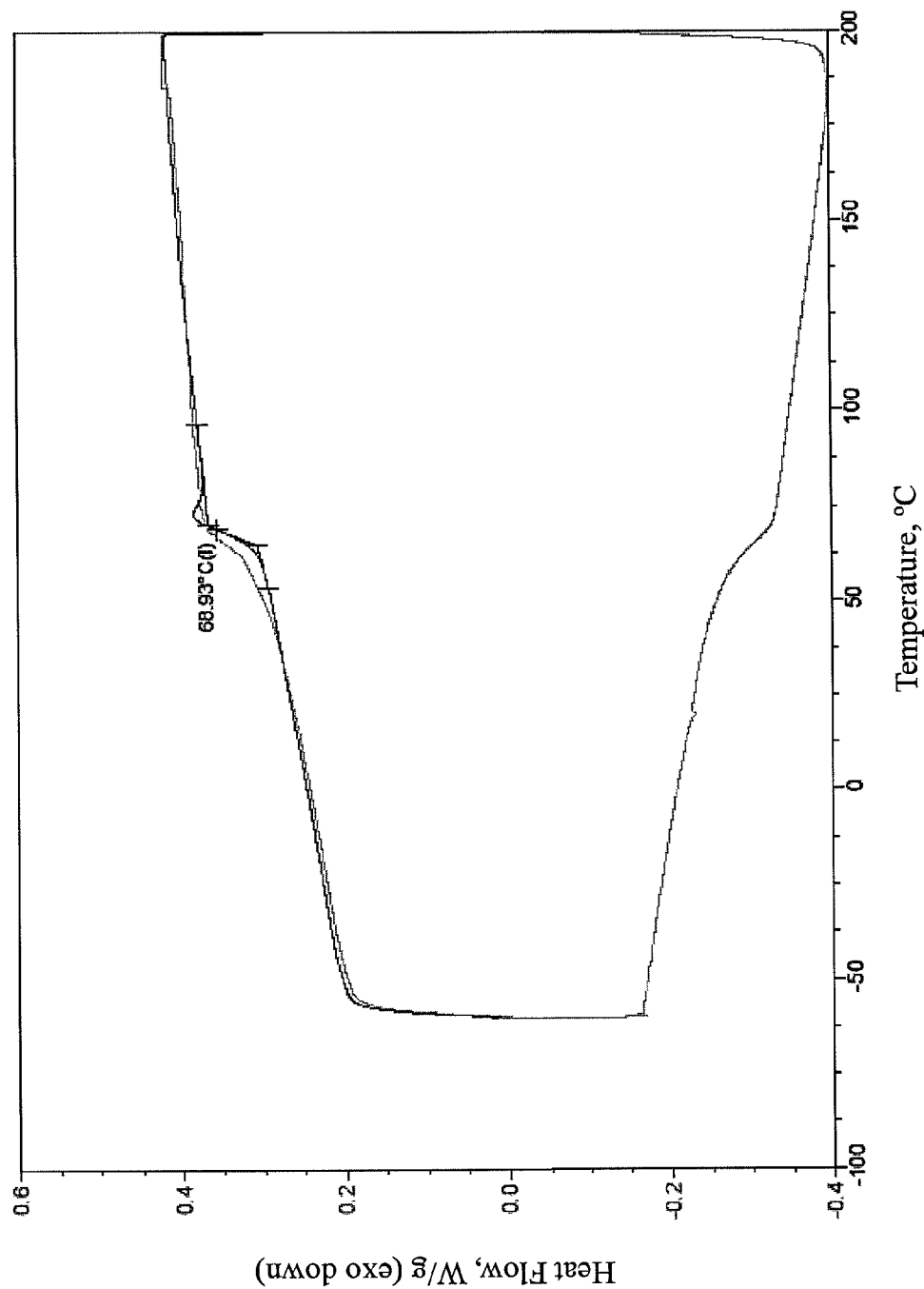
FIG. 3 shows a DSC plot of a compound of the invention.

The resulting polymer had a $T_g$ of 69° C. as measured by DSC. The polymer was analyzed by GPC using DMF as the solvent and PMMA standards. This polymer was found to have $M_n$=12,604, $M_w$=20,291, and a PDI of 1.61. The GPC trace is shown in FIG. 3.

Example 15

Synthesis of Sorbitol Monomer with an Average Ester Functionality of 2.0 Per Molecule, and Subsequent Polymerization to Form a Branched Polymer

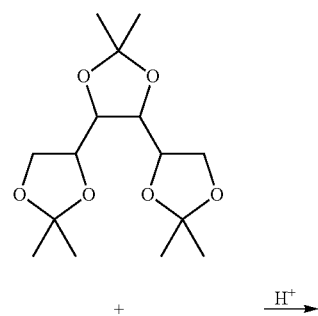

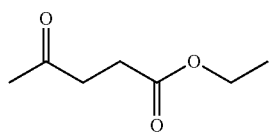

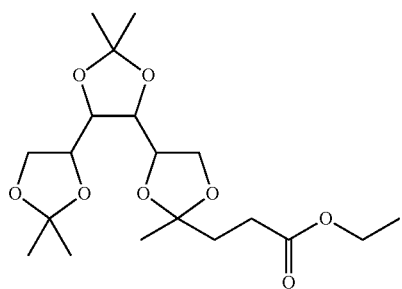

and

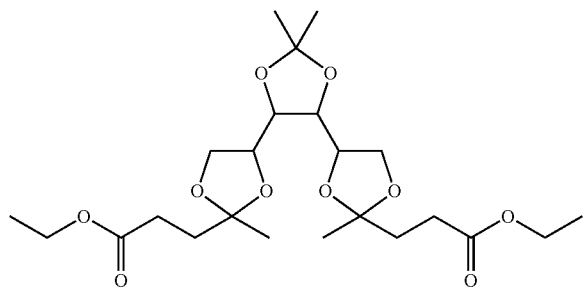

and

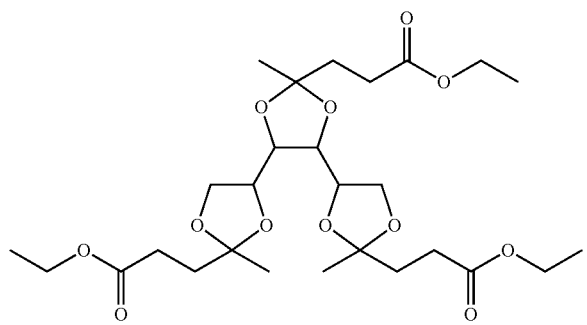

} mixture of these 3 products (plus other isomers)

To a 100 mL 3-neck round bottom flask equipped with a magnetic stir bar, and nitrogen inlet and a Dean Stark trap topped with a condenser attached to a mineral oil bubbler was added sorbitol tris-acetonide synthesized according to the method of Example 1 (10.12 g, 33 mmol), ethyl levulinate (24.14 g, 167 mmol, obtained from the Langfang Triple Well Chemicals Company, Ltd. of Langfang City, HeBei, China), and 98% $H_2SO_4$ (1 μL, about 50 ppm based on total weight of reagents, obtained from Fisher Scientific of Waltham, Mass.). The system was placed under a slow stream of nitrogen and placed in an oil bath. The oil bath temperature was set to 60° C. This temperature was maintained for approximately 29 hours, and then the system cooled to room temperature. In order to neutralize the acid, 15 mesh activated, basic $Al_2O_3$ (about 3.5 g, about 10 wt. %) was added to the flask and stirred for approximately 1 hour. The $Al_2O_3$ was removed by vacuum filtration over a sintered glass funnel. The unreacted ethyl-levulinate was removed by distillation on a rotary evaporator using an oil bath temperature of about 160° C., and a pressure of about 4 Torr.

The resulting mixture was analyzed by GC-FID and found to contain about 5.2% mono-levulinate, about 84% bis-levulinate, and about 8.6% tris-levulinate. The ester functionality of this mixture was determined using the equation:

Average functionality $(f_{av}) = \Sigma(N_i f_i)/\Sigma(N_i)$ wherein:

$f_{av}$ is the average ester functionality of the mixture, $N_i$ is the number of moles of each functional molecule in the mixture, and $f_i$ is the functionality of each molecule in the mixture.

Using the equation, a functionality $f_{av}$ of 2.01 was found for this mixture.

A 200 mL 3-neck round bottom flask equipped with a mechanical stirrer, and Dean Stark trap topped with a condenser and a nitrogen inlet/outlet was charged with the above mixture having an average functionality of 2.01 (10.92 g), 1,6-hexamethylenediamine (2.54 g, 22 mmol, obtained from Acros Organics of Geel, Belgium), and ethylene glycol (0.71 g, 11 mmol, obtained from Fisher Scientific of Waltham, Mass.). The system was degassed/backfilled with nitrogen 5 times down to a pressure of about 1 Torr. Ti(OBu)$_4$ (2.86 μL, about 200 ppm based on total weight of reagents, obtained from Acros Organics of Geel, Belgium) was added to the flask, and the system degassed/backfilled with nitrogen an additional 5 times. The system was placed in an oil bath and heated to 190° C. After approximately 19 hours, the oil bath temperature was increased to 210° C. and maintained for 90 minutes. The pressure in the flask was then decreased to approximately 24 Torr and maintained for 20 minutes. The pressure was decreased to about 1 Torr and maintained for 2.5 hours. The temperature was then increased to 215° C. and maintained for 2.5 hours. The system was backfilled with nitrogen and cooled so the product could be removed from the flask. The resulting polymer was analyzed by DSC and found to have a $T_g$ of about 53° C.

Comparative Example 16C

A 500 ml 3-neck round bottom flask was charged with 36.64 g (0.3 mol) erythritol (obtained from the Cargill Company of Wayzata, Minn.) and 346.01 g (2.4 mol) ethyl levulinate (obtained from the Sigma Aldrich Company of St. Louis, Mo.). The flask was equipped with a Dean Stark trap, mechanical stirrer, and thermocouple. The contents of the flask were heated to 80° C., at which point 15.99 µl of concentrated sulfuric acid (obtained from the Sigma Aldrich Company) was added to the reaction flask via a metered microliter pipette. A vacuum was applied to the reaction flask, slowly bringing the pressure down to 40 torr. This pressure was maintained with stirring while liquid was observed to collect in the Dean Stark trap. About 1 hour, 45 minutes after addition of sulfuric acid, the vacuum was released and a small sample was removed from the reaction flask. The vacuum was then reestablished. After an additional 1 hour, 15 minutes reaction time, liquid had stopped collecting in the Dean Stark trap. The vacuum was released, and the contents of the flask were allowed to cool to ambient temperature. A second sample was removed from the reaction flask.

Both samples removed were analyzed by GC-MS. The percentages of products were calculated by disregarding the presence of ethyl levulinate, because of the excess molar equivalents of ethyl levulinate used in the reaction. Thus, the percentages of erythritol, the monoketal of erythritol with one molar equivalent of ethyl levulinate, and the bisketal of erythritol with two molar equivalents of ethyl levulinate were calculated by determination of their relative GC peak areas. The sample removed at 1 hour, 45 minutes was found to contain 93.03% of the bisketal, 6.97% of the monoketal, and 0% erythritol by GC peak area. The sample removed after the additional 1 hour, 15 minutes reaction time was found to contain greater than 100% of the bisketal (ethyl levulinate aside).

The contents of the reaction flask were combined with other batches of materials made using the procedure above. The combined crude reaction mixture was added to the addition flask of a short path wiped film evaporator equipped with carbon blades. A vacuum was applied to the apparatus until the pressure in the apparatus reached 100 millitorr. While under vacuum the entire apparatus was heated to 150° C. The wiped film column blades were rotated at 70% at the maximum rate available on the apparatus. The cold finger of the wiped film apparatus was adjusted to 0° C. using a refrigerated chiller. Upon reaching the target temperature the contents of the reaction flask were dripped into the wiped film column at a rate of 160 drops/minute. After 3 hours, 15 minutes the contents of the addition flask had been emptied into the column. The non-distilled residue that was captured was analyzed by GC-MS, and $^1$H NMR. The GC-MS analysis showed 99.70%, $^1$H NMR analysis showed 98.70% ethyl levulinate bisketal of erythritol (Et-BLEK).

Figure 4:
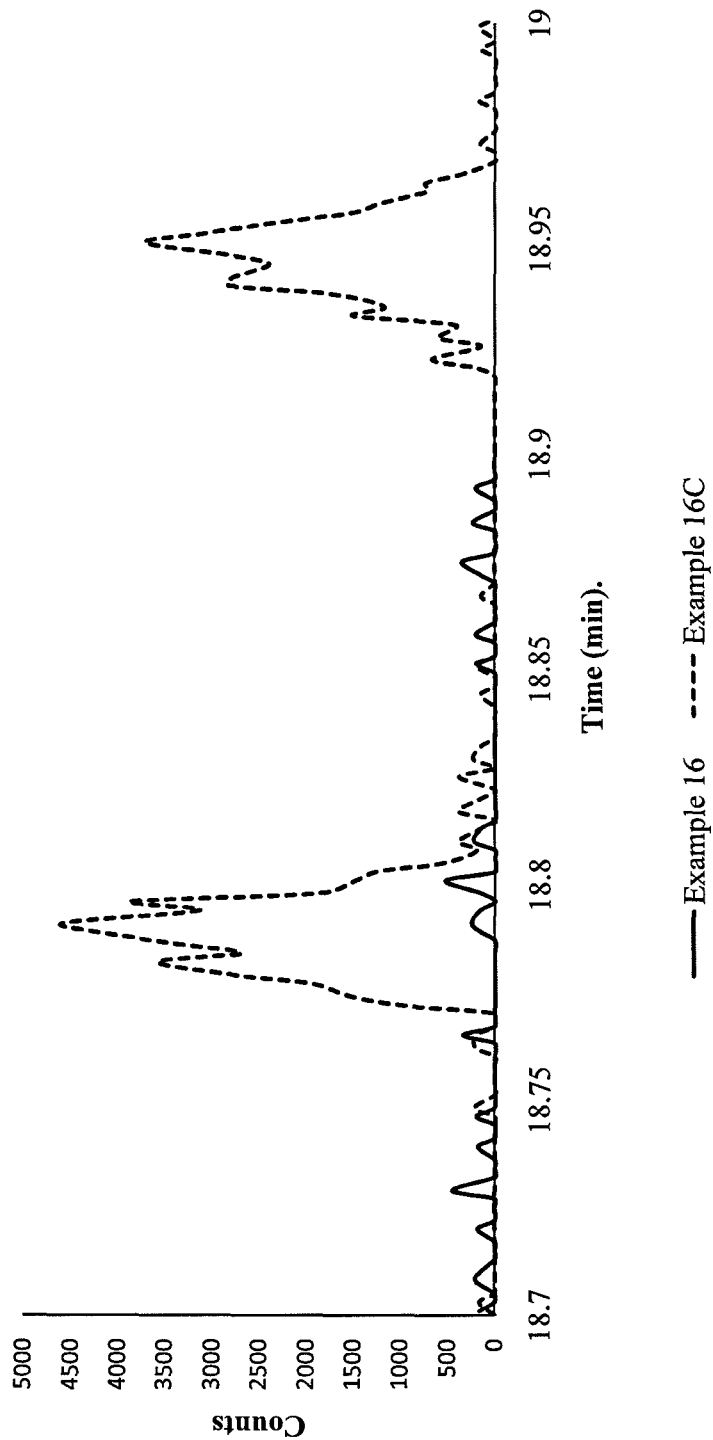
FIG. 4 shows a GC-MS plot for a compound of the invention.

The Et-BLEK made and purified using this method was analyzed by GC-MS, and the portion of the GC-MS trace attributable to hydroxylated (e.g. unreacted) side products is shown in FIG. 4.

Example 16

Transketalization of Erythritol Bis-Acetonide with Ethyl Levulinate

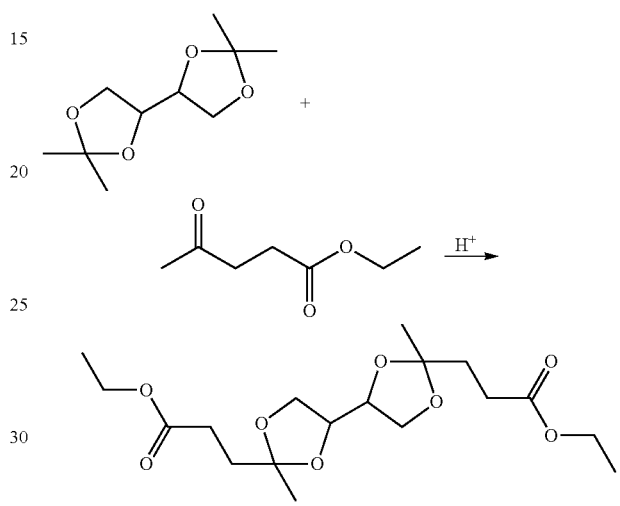

To a 1 L 3-neck round bottom flask equipped with a magnetic stir bar, a nitrogen inlet, and a nitrogen outlet connected to a mineral oil bubbler were added erythritol bis-acetonide (EBA) obtained from Example 8 (91.88 g, 0.454 mol), ethyl levulinate (295.91 g, 2.05 mol, obtained from the Langfang Triple Well Chemicals Company, Ltd. of Langfang City, HeBei, Chinca), and para-toluene sulfonic acid(98%) (0.445 g, about 1150 ppm based on total weight of reagents, obtained from the Sigma-Aldrich Company of St. Louis, Mo.). The flask was left in an oil bath under a stream of nitrogen. The oil bath temperature was set to 50° C. and maintained for approximately 16 hours. The temperature was then increased to 60° C. for 2.75 hours. The flask was then cooled to room temperature.

Then 150 mesh activated, basic $Al_2O_3$ (about 40 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The unreacted ethyl levulinate as well as impurity consisting of the ketal of one levulinate ketal and one acetonide was removed from the reaction mixture by rotating on a rotary evaporator with an oil bath temperature of 180° C. and pressure of approximately 2 Torr. Once an initial liquid stopped condensing in the condensation flask of the rotary evaporator, the pressure was reduced to about 300-1000 mTorr and the rotary evaporator allowed to run until the remaining impurity was observed to evaporate.

The undistilled liquid was then analyzed by GC-FID and GC-MS. GC-FID showed that the crude product was about 98.6% of the bisketal of erythritol and ethyl levulinate ("Et-BLEK"), about 0.2% of the hybrid ketal of monoacetonide and ethyl levulinate, and about 0.04% of the mono-levulinate ketal of erythritol. The portion of the GC-MS trace attributable to hydroxylated (e.g. unreacted) side products is shown in FIG. 4.

Example 17

Transketalization of Erythritol Bis-Methyl Isobutyl Ketone Ketal with Ethyl Levulinate

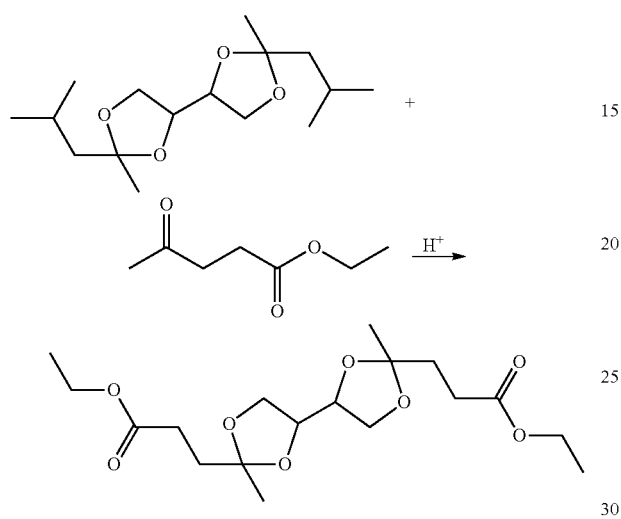

To a 250 mL 3-neck round bottom flask equipped with a magnetic stir bar, a nitrogen inlet, and a nitrogen outlet connected to a mineral oil bubbler were added erythritol bis-MIBK obtained using the method of Example 9 above (31.33 g, 0.190 mol), ethyl levulinate (63.14 g, 0.438 mol, obtained from the Langfang Triple Well Chemicals, Ltd. of Langfang City, HeBei, China), and 98% $H_2SO_4$ (2.6 µL, about 50 ppm based on total weight of reagents, obtained from Fisher Scientific of Waltham, Mass.). The flask was placed under a stream of nitrogen, and placed in an oil bath. The bath temperature was set to 70° C. and maintained for 21 hours. The temperature was then increased to 90° C. and maintained for 3 hours. The flask was cooled to room temperature.

Then 150 mesh activated, basic $Al_2O_3$ (about 10 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The Ethyl levulinate and MIBK were stripped on a rotary evaporator by applying a vacuum of about 7 Torr and slowly increasing the oil bath temperature from 40° C. up to 180° C. while rotating. The pressure in the flask was reduced to about 140 mTorr, and the temperature lowered to 160° C. Once liquid appeared in the bump flask the temperature was increased to 175° C. and maintained for 3 minutes. The flask was then cooled to room temperature and the vacuum released. The undistilled liquid was analyzed by GC-FID and found to contain about 98.3% of the desired bis-levulinate ketal product and about 0.7% of a mono-levulinate impurity. This desired product was recovered with a 42% yield.

Example 18

Polyesterification of Bis-Ethyl Levulinate Mono-Acetonide Ketal of Sorbitol

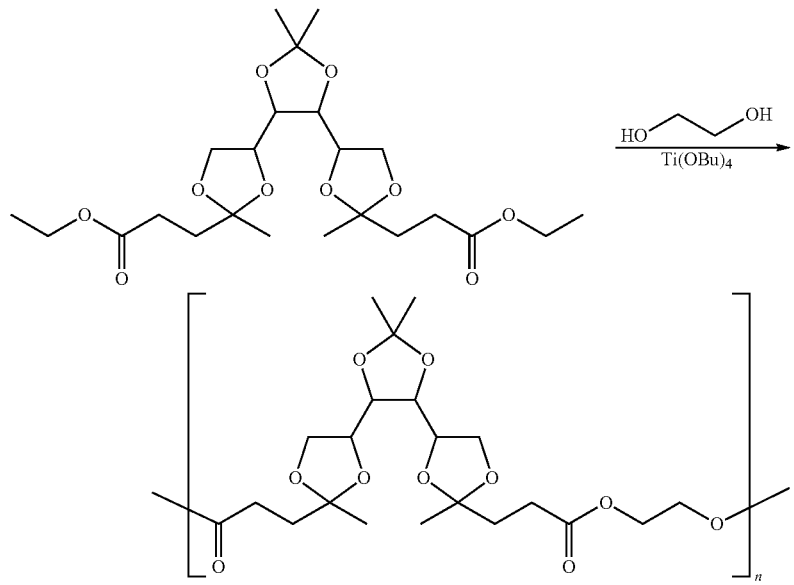

To a 250 mL 3-neck round bottom flask equipped with a mechanical stirrer and a Dean Stark trap topped with a condenser and a nitrogen inlet/outlet were added the bis-levulinate, mono-acetonide ketal obtained using the method of Example 13 (30.29 g, 63.8 mmol) and ethylene glycol (7.96 g, 128 mmol, obtained from Fisher Scientific of Waltham, Mass.). The flask was degassed/backfilled with nitrogen a total of 5 times down to a pressure of approximately 1 Torr, then backfilled with nitrogen and maintained under a nitrogen blanket. $Ti(OBu)_4$ catalyst (7.7 µL, about 200 ppm based on total weight of reagents, obtained from Acros Organics of Geel, Belgium) was added to the flask and the system degassed/backfilled an additional 3 times. The flask was placed in an oil bath and the temperature set to 190° C. After approximately 17.5 hours, the temperature of the oil bath was increased to 210° C. and maintained for 5 hours. The pressure in the flask was then decreased to approximately 10 Torr, and continued to slowly decrease to approximately 5 Torr over the next 3 hours. The reaction was left at these conditions for approximately 15 hours, at which the point the pressure in the flask was further reduced down to about 300-400 mTorr. After 5.5 hours at these conditions the flask was backfilled with nitrogen and cooled to room temperature.

The resulting polymer was analyzed by GPC (THF solvent and polystyrene standards) and found to have $M_n$=2768, $K_w$=7954, and PDI=2.87. DSC analysis revealed that the polymer had a $T_g$ of approximately 17° C.

Example 19

Polymerization of et-BLSK(A) Using 1,6-Hexamethylenediamine and Ethylene Glycol

To a 250 mL 3-neck round bottom flask equipped with a mechanical stirrer and a Dean Stark trap topped with a condenser and a nitrogen inlet/outlet was added Et-BLSK(A) obtained using the method of Example 13 (31.46 g, 66 mmol) and ethylene glycol (8.35 g, 135 mmol, obtained from Fisher Scientific of Waltham, Mass.). The system was left under a gentle stream of nitrogen for approximately 2 hours. The system was then degassed/backfilled with nitrogen a total of 5 times down to a pressure of approximately 1 Torr. Ti(OBu)$_4$ catalyst (8.0 µL, approximately 200 ppm based on the total weight of reagents, obtained from Acros Organics of Geel, Belgium) was added to the flask and the system degassed/backfilled with nitrogen an additional 5 times. The flask was placed in an oil bath and the bath heated to 190° C. After approximately 20 hours, the pressure in the flask was reduced to approximately 5 Torr over the course of 2 hours. The temperature was then increased to 210° C. and maintained for 2.5 hours. The flask was backfilled with nitrogen and cooled to room temperature, at which point 1,6-hexamethylenediamine (7.31 g, 63 mmol, obtained from Acros Organics of Geel, Belgium) and ethylene glycol (0.36 mL) were added to the flask, and the oil bath heated back up to 190° C. After approximately 3.25 hours the temperature was increased to 200° C. After another 1 hour the temperature was increased again to 210° C. After 3.5 hours, the pressure in the flask was reduced to approximately 300-1000 mTorr and maintained for approximately 10.75 hours. The flask was then backfilled with nitrogen and cooled to room temperature.

The resulting polymer was analyzed by DSC and found to have a $T_g$ of 74° C.

Example 20

Ketalization of Erythritol Using 2-Octanone

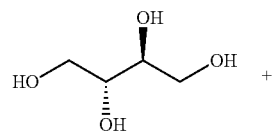

-continued

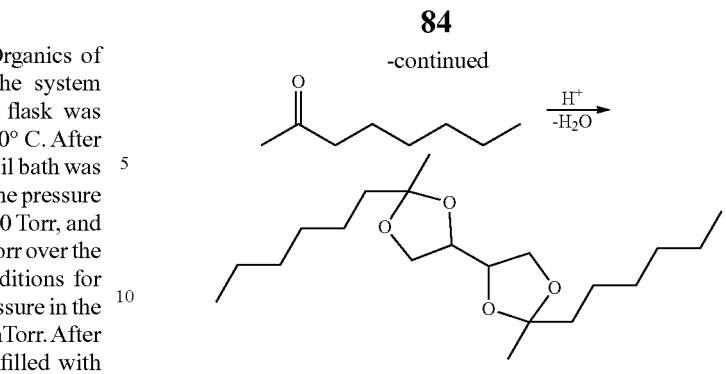

To a 250 mL 3-neck round bottom flask equipped with a magnetic stir bar and a Dean Stark trap topped with a condenser and a nitrogen inlet/outlet were added erythritol (30.33 g, 0.248 mol, obtained from Cargill Inc. of Minnetonka, Minn.), 2-octanone (132.48 g, 1.03 mol, obtained from the Sigma-Aldrich Company of St. Louis, Mo.), and 98% $H_2SO_4$ (6.6 µL, about 75 ppm based on total weight of reagents, obtained from the Sigma-Aldrich Company of St. Louis, Mo.). The flask was placed in an oil bath and the bath heated to 120° C. The pressure inside the flask was reduced to about 400-500 Torr. Liquid began collecting in the Dean Stark trap and separated into two distinct layers. The flask was backfilled with nitrogen, the Dean Stark trap filled with 2-octanone and the oil bath heated until the reaction began refluxing. After about 7 hours of refluxing, the reaction was cooled to room temperature.

Then about 150 mesh activated, basic $Al_2O_3$ (about 16 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The crude mixture was analyzed by GC-MS and found to contain about 45.9% 2-octanone, about 8.4% dehydrated mono-ketal, about 5.5% mono-ketal, and about 39.1% bis-ketal, the corresponding structures of which are shown below.

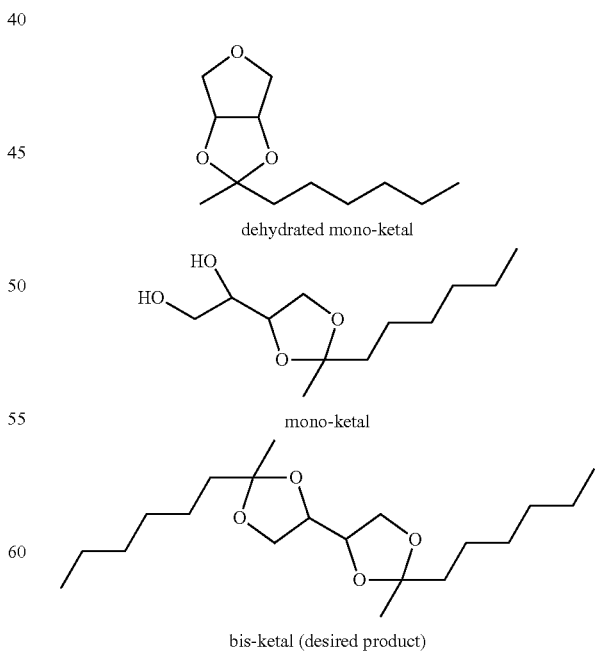

dehydrated mono-ketal mono-ketal bis-ketal (desired product)

The mixture of products was purified by distillation using a short-path distillation column. The desired bis-ketal distilled over when the head temperature was about 137°-150° C. and the pressure in the system was about 2.5 Torr. The receiving flask contained 38.27 g (about 45% yield) of the desired bis-ketal which was found to be about 97.8% pure by GC-MS.

Example 21

Transketalization of Erythritol Bis-Octanone Ketal with Ethyl Levulinate

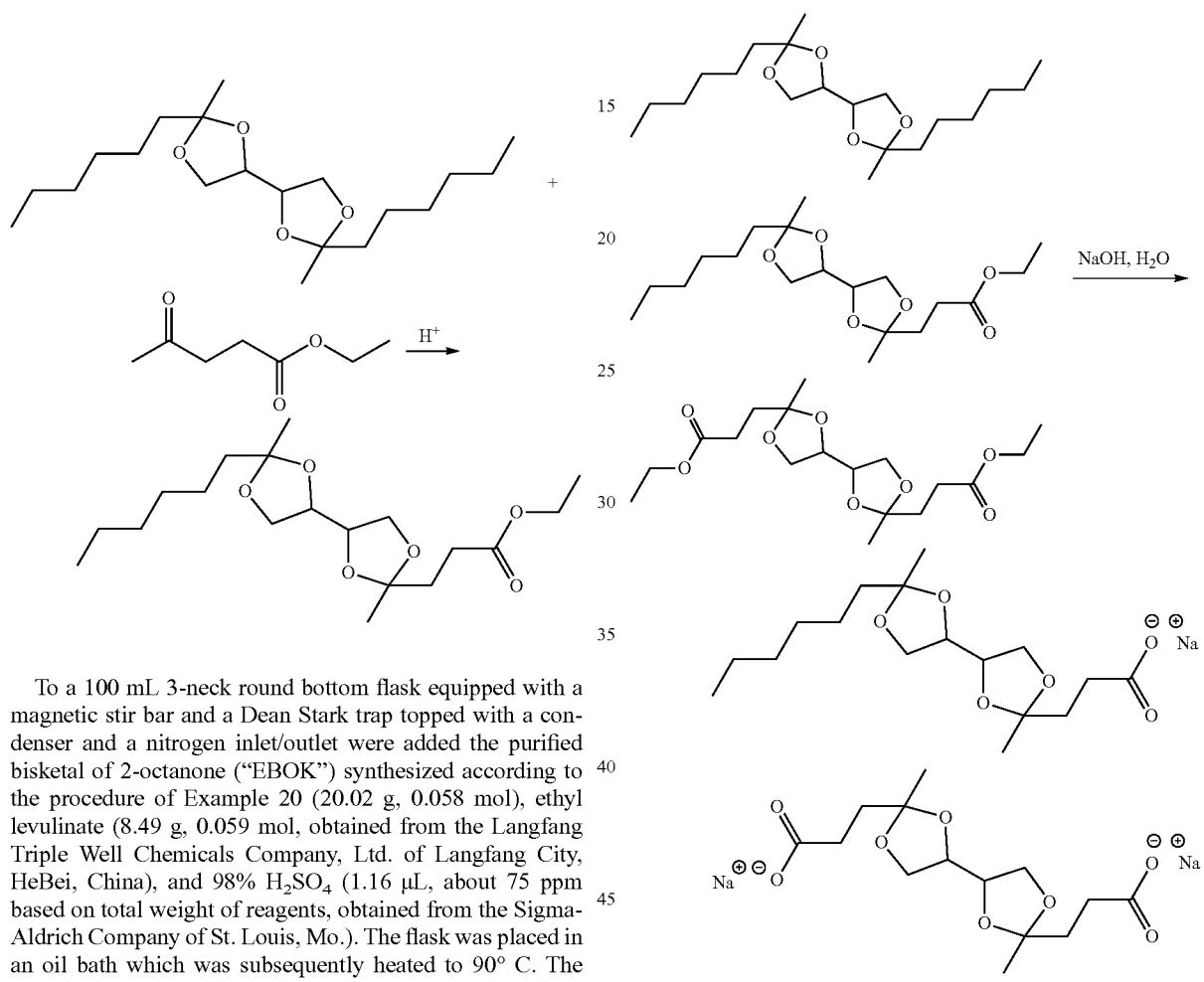

To a 100 mL 3-neck round bottom flask equipped with a magnetic stir bar and a Dean Stark trap topped with a condenser and a nitrogen inlet/outlet were added the purified bisketal of 2-octanone ("EBOK") synthesized according to the procedure of Example 20 (20.02 g, 0.058 mol), ethyl levulinate (8.49 g, 0.059 mol, obtained from the Langfang Triple Well Chemicals Company, Ltd. of Langfang City, HeBei, China), and 98% $H_2SO_4$ (1.16 μL, about 75 ppm based on total weight of reagents, obtained from the Sigma-Aldrich Company of St. Louis, Mo.). The flask was placed in an oil bath which was subsequently heated to 90° C. The pressure in the flask was reduced to about 27.5 Torr. The progress of the reaction was monitored by GC-MS. After about 3.5 hours, the GC-MS showed that almost of the ethyl levulinate had been consumed but there was still a large amount of unreacted EBOK present. An additional 4.22 g (0.029 mol) of ethyl levulinate was added to the system. After an additional 1.66 hours, the flask was backfilled with nitrogen and cooled to room temperature.

Then 150 mesh activated, basic $Al_2O_3$ (about 3 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. The crude mixture was analyzed by GC-FID and found to contain about 7.8% 2-octanone, about 7.9% Et-Lev., about 23.6% EBOK, about 41.8% mono-octanone, mono-levulinate ketal of erythritol, and about 18.0% bis-levulinate ketal of erythritol. The 2-octanone and EtLev were removed by distillation, and the mixture analyzed again by GC-FID. This mixture was found to contain about 27.6% EBOK, about 49.5% of the mono-octanone, mono-levulinate ketal of erythritol, and about 21.8% bis-levulinate ketal of erythritol.

Example 22

Saponification of the Crude Reaction Mixture of Example 21

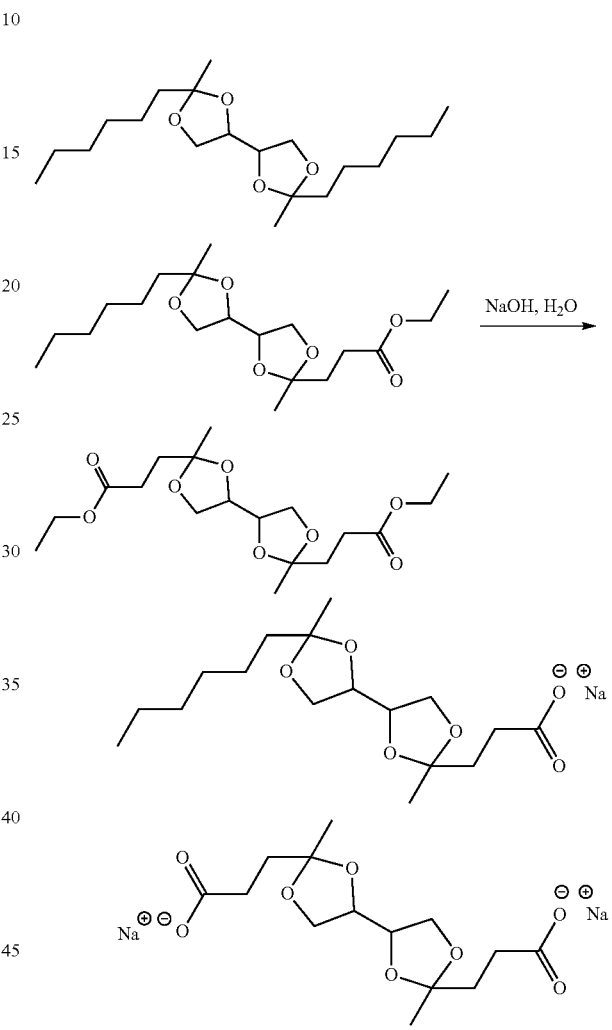

To a 300 mL round bottom flask was added 14.67 g of the crude reaction mixture from Example 21. In a small beaker, sodium hydroxide (1.54 g, 0.039 mol, obtained from Fisher Scientific of Waltham, Mass.) was dissolved in DI water (35.73 g, 1.99 mol). The entire sodium hydroxide solution was added in one aliquot to the flask containing the crude reaction mixture. The flask was placed on a rotary evaporator with an oil bath temperature set to 55° C. and was rotated for about 30 minutes. Vacuum of about 4 Torr was then applied to the system to remove the water and ethanol. After the liquid had been removed the flask contained a mixture of some whitish crystals and some brown/orange oil. An aliquot of hexane was added to the flask, the contents were swirled together for about one minute, then the liquid was filtered using a sintered glass funnel. The solid was dried overnight in a drying oven to remove any remaining liquid, and the hexane wash layer was analyzed by GC-FID. The hexane layer was found to contain about 47.7% EBOK, about 42.5% of the mono-octanone, mono-levulinate ketal of erythritol, and about 7.6% bis-EtLev ketal. The hexane insoluble solid had a waxy feel and dissolved readily in water. A small amount of the saponified product was dissolved in water, and then an equivalent amount of hexane added. The mixture was allowed to sit overnight. The resulting mixture contained a transparent aqueous layer (bottom layer) topped with a cloudy layer which spanned a visible water/hexane divide, and then finally a transparent hexane layer on top.

Example 23

Transketalization Between Bis-Ethyl Levulinate Ketal and 2-Undecanone

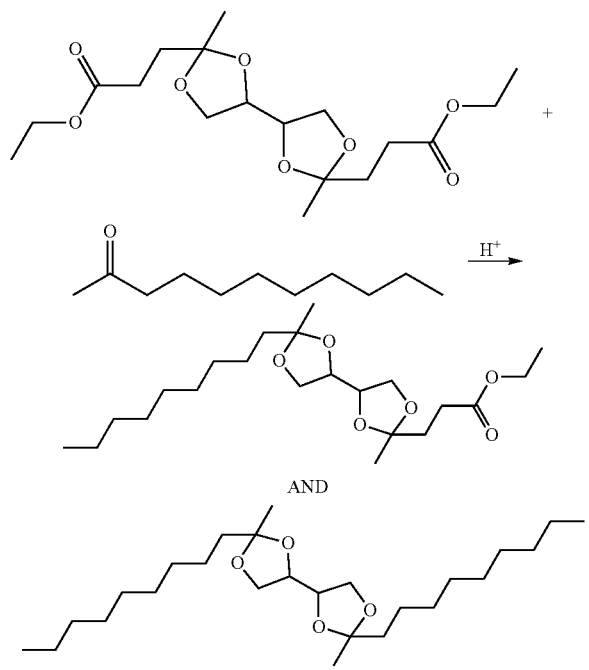

To a 250 mL 3-neck round bottom flask equipped with a magnetic stir bar and a Dean Stark trap topped with a condenser and a nitrogen inlet/outlet were added bis-ethyl levulinate ketal of erythritol (Et-BLEK) synthesized according to the procedure of Comparative Example 16C (30.15 g, 0.081 mol), 2-undecanone (27.55 g, 0.162 mol, obtained from the Sigma-Aldrich Company of St. Louis, Mo.), and 98% $H_2SO_4$ (2.4 µL, about 75 ppm based on total weight of reagents, obtained from the Sigma-Aldrich Company of St. Louis, Mo.). The reaction was monitored by GC-MS in order to track how the composition changed over time. The flask was placed in an oil bath which was subsequently heated to 90° C. The pressure inside the flask was reduced to about 10 Torr and these conditions maintained throughout the experiment. Samples were also taken periodically during the experiment for GC-MS analysis. After approximately 6 hours, the flask was backfilled with nitrogen and cooled to room temperature. Table 1 shows the relative concentrations of the ketalized compounds present in the reaction mixture over the course of the reaction. The GC-MS monitoring results are shown in Table 3; "0 exchanges" means bis-levulinate ketal of erythritol; "1 exchange" means the hybrid ketal with one EtLev and one 2-undecanone ketal; and "2 exchanges" means bis 2-undecanone ketal.

TABLE 3

GC-MS analysis of aliquots of the reaction mixture of Example 21 at various times during the reaction.

| Time (hr.) | 0 exchanges (% of ketal containing species) | 1 exchange (% of ketal containing species) | 2 exchanges (% of ketal containing species) |
| --- | --- | --- | --- |
| 0 | 100 | 0 | 0 |
| 1 | 80.53 | 18.55 | 0.93 |
| 1.80 | 66.46 | 30.70 | 2.83 |
| 2.82 | 54.46 | 40.27 | 5.26 |
| 5.82 | 38.01 | 49.99 | 12.00 |

Example 24

Transketalization of Trisacetonide of Sorbitol with Diethyl 4-Oxopimelate

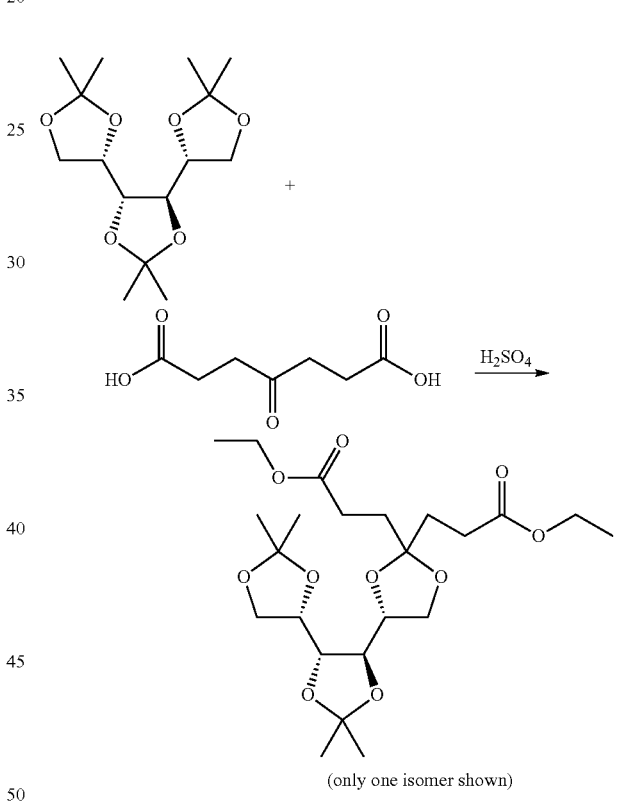

(only one isomer shown)

A 500 mL 3-neck flask was equipped with a magnetic stir bar and vacuum adapter. The flask was charged with 131.34 g (0.434 mol) D-sorbitol trisacetonide (synthesized according to the method of Example 1), 50.01 g (0.217 mol) diethyl 4-oxo-pimelate (obtained from the Sigma-Aldrich Company of St. Louis, Mo.), and 10 µL diethylene glycol (obtained from Fisher Scientific of Waltham, Mass.). A vacuum of 40-50 Torr was applied to the flask and the flask was immersed in a 70° C. oil bath with stirring. The reaction was monitored by periodically removing samples for GC-FID. After 64 hours the solution was cooled to room temperature and then diluted with 200 mL 2,2-dimethoxylpropane (obtained from the Sigma-Aldrich Company of St. Louis, Mo.). The diluted reaction product was neutralized by adding 10 g basic alumina (obtained from the Sigma-Aldrich Company of St. Louis, Mo.), stirring the resulting slurry, and filtering off the solids using a fritted glass filter (medium frit). The filtrate was concentrated on a rotary evaporator under a vacuum of about 100 Torr while immersed in an oil bath set at 80° C. The concentrated viscous liquid was distilled using a Kugelrohr apparatus (230° C., 0.8-0.9 Torr) to yield 49.44 g of a pale green viscous liquid (48.0% yield based on moles of diethyl 4-oxo-pimelate) that was the purified monopimelic ketal product, as determined by GC-FID.

Examples 25-28

Transketalization of Sorbitol Trisacetonide with Diethyl-4-Oxopimelate Using Various Catalysts A 100 mL round bottom flask equipped with a magnetic stir bar was charged with D-sorbitol trisacetonide synthesized using the procedure of Example 1 (5.00 g, 16.5 m mol), diethyl 4-oxo-pimelate (1.91 g, 8.3 mmol) (obtained from the Sigma-Aldrich Company of St. Louis, Mo.), ethylene glycol (5 µL) (obtained from Fisher Scientific of Waltham, Mass.), and sulfuric acid (0.90 µL, 0.2 mol % relative to diethyl 4-oxo-pimelate) (98%, obtained from Fisher Scientific). The flask was placed under vacuum using a Teflon pump and stirred in an oil bath having a temperature set to 70° C. Stirring was maintained for approximately 15 hours and then the flask was removed from the oil bath and cooled to room temperature. Then the contents of the flask were subjected to GC-MS.

This same reaction was repeated using p-toluenesulfonic acid (obtained from Sigma-Aldrich Company of St. Louis, Mo.), sulfamic acid (obtained from Fisher Scientific of Waltham, Mass.) and pyridinium p-toluenesulfonate (obtained from the Acros Organics of Geel, Belgium) under the same concentration (the catalyst amount was 0.2 mol % relative to diethyl 4-oxo-pimelate). The results are listed in the Table 4.

TABLE 4

Comparison on the transketalization of D-sorbitol trisacetonide and diethyl 4-oxo-pimelate by using different catalysts (monitored by GC-MS)

| | | Compound, % by GC | | | |
|---|---|---|---|---|---|
| Example No. | Catalyst | D-sorbitol trisacetonide | Diethyl 4-oxo-pimelate | Bis-acetonide mono-pimelate ketal of D-sorbitol[1] | Mono-acetonide bis-pimelate ketal of D-sorbitol |
| 25 | Sulfuric acid | 53.425% | 6.031% | 37.027% | 2.034% |
| 26 | p-Toluene-sulfonic acid | 81.047% | 15.558% | 1.365% | 0 |
| 27 | Sulfamic acid | 78.492% | 16.713% | 2.617% | 0 |
| 28 | Pyridinium p-toluene sulfonate | 79.978% | 17.740% | 0 | 0 |

[1]Combination of all isomers

Example 29

Polyamide Synthesized Directly from Monopimelic Ketal of Sorbitol and 1,6-Hexanediamine

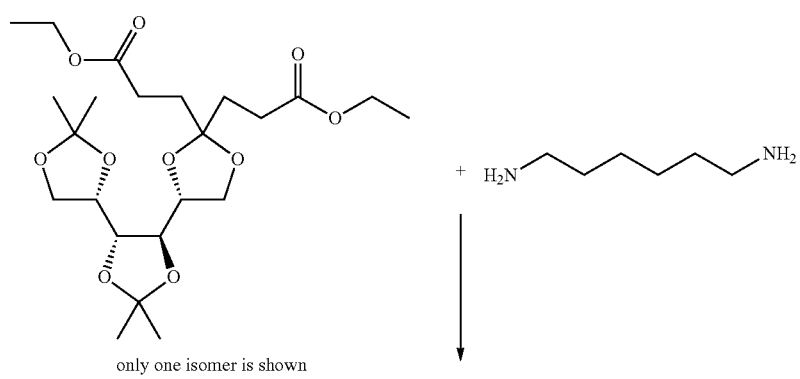

only one isomer is shown

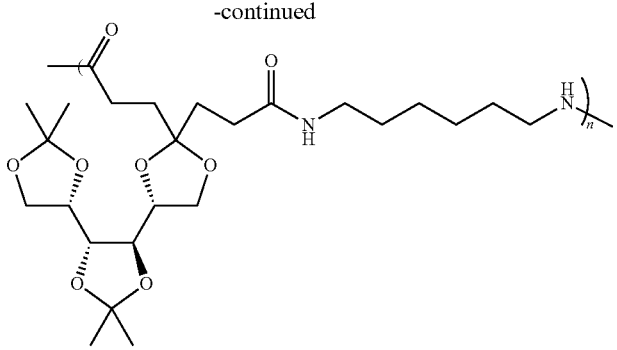

To a flame-dried 250 mL 3-neck flask equipped with a mechanical stirrer and Dean Stark trap were added the purified monopimelic ketal synthesized according to the procedure of Example 24 (23.73 g, 0.0500 mol), 1,6-hexanediamine (11.84 g, 0.102 mol, obtained from Acros Organics of Geel, Belgium), and ethylene glycol (0.31 g, 0.00499 mol, obtained from the Sigma-Aldrich Company of St. Louis, Mo.). The system was placed under nitrogen blanket. The contents of the flask were stirred at an initial oil bath temperature of about 170° C. under nitrogen, and the oil bath temperature was raised gradually to about 210° C. at a ramping rate of about 3° C./hour. After about 11 hours, about 1.6 mL of a colorless liquid collected in the Dean Stark trap. The liquid was drained, and the reaction system was placed under vacuum (0.3-1 Torr). The reaction was cooled to room temperature and backfilled with nitrogen, and additional aliquot of 1,6-hexanediamine (0.35 g, 3.01 mmol) was added. The flask was degassed at room temperature with five repetitions of evacuating the flask to approximately 5 Torr followed by backfilling with nitrogen. While under vacuum of about 1.7 Torr, the reaction was heated in an oil bath at a temperature set to 210° C. After 2 hours, the vacuum was lowered to 300 mTorr. The reaction was continued under these conditions for an additional 16 hours. Then the contents of the flask were cooled to ambient temperature and the vacuum backfilled with nitrogen. The crude polymer was isolated as an orange solid. Yield: 21.33 g. $T_g$=67.0° C.

Example 30

Polyamide Synthesized from Bis-Acetonide, Mono-Pimelate Ketal of Sorbitol and 1,6-Hexamethylenediamine Via Ester Aminolysis

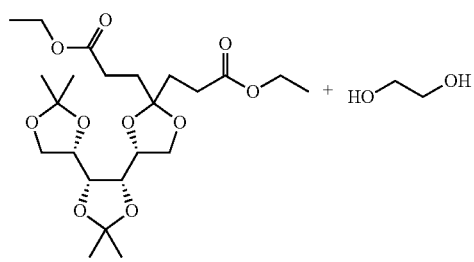

(only one isomer shown)

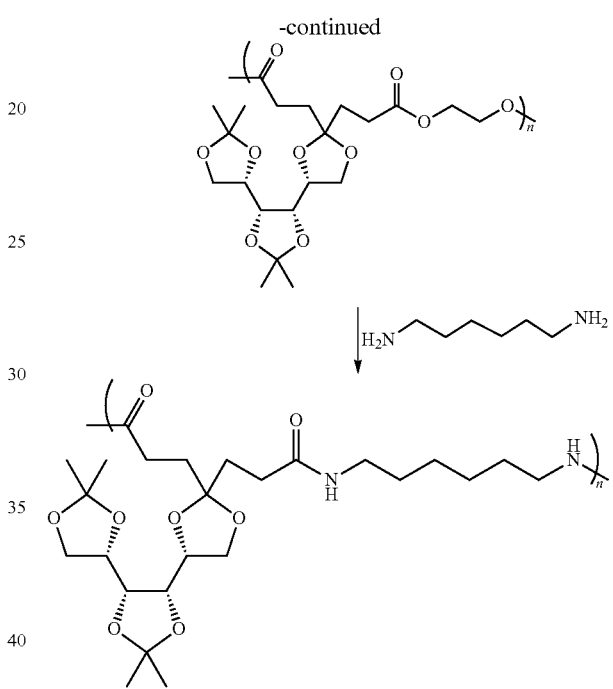

To a flame-dried 250 mL 3-neck flask equipped with a mechanical stirrer and Dean Stark trap were added the purified monopimelic ketal of sorbitol, synthesized according to the procedure of Example 24 (23.50 g, 0.0495 mol) and ethylene glycol (5.538 mL, 0.0990 mol, obtained from the Sigma-Aldrich Company of St. Louis, Mo.). The contents of the flask were placed under nitrogen and stirred in an oil bath set to a temperature of 120° C. for 3 hours, and then cooled to 60° C. Ti(OBu)$_4$ (5.9 µL, 200 ppm) (obtained from Acros Organics of Geel, Belgium) was added to the reaction mixture while maintaining the nitrogen blanket. The contents of the flask were then stirred for 11 hours under nitrogen in an oil bath set to a temperature of 190° C. About 2 mL of colorless liquid collected in the Dean Stark trap and was drained. Then the flask was placed under vacuum of about 3-4 Torr. Heating and vacuum were continued for an additional 20 hours. The reaction was then cooled gradually to 120° C. A small sample of the resulting brown polymer was taken for DSC measurement; $T_g$=−7.3° C.

To the flask was added 1,6-hexamethylenediamine (5.46 g, 0.0470 mol) (obtained from Acros Organics of Geel, Belgium) at room temperature under nitrogen. The flask was heated under nitrogen in an oil bath set to a temperature of about 120° C. and stirred to mix the contents. Stirring was continued for 14.5 hours in the oil bath which was set to a temperature of 190° C. About 2 mL of a liquid collected in the Dean Stark trap and was drained, then the flask was placed under vacuum while in the 190° C. oil bath. Over the next 5 hours the temperature of the oil bath was gradually raised from 190° C. to 220° C., and the vacuum was lowered from 3 Torr to 200 mTorr. Heating and vacuum were then continued for an additional 19 hours. The flask was then cooled to 180° C. under nitrogen, and a yellow-orange polymer was collected. Total yield of polymer was 22.20 g. DSC analysis showed the polymer had a $T_g$ of 78.3° C.

Example 31

Ketalization of Pentaerythritol Using Methylisobutyl Ketone (MIBK)

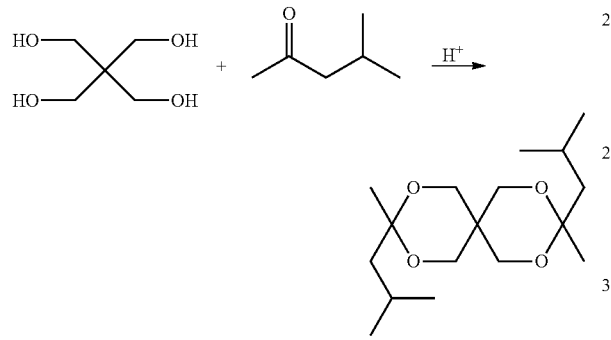

To a 250 mL 3-neck round bottom flask equipped with a magnetic stir bar and a Dean Stark trap equipped with a condenser and nitrogen inlet/outlet were added pentaerythritol (24.6 g, 0.181 mol, obtained from the Sigma-Aldrich Company of St. Louis, Mo.), 4-methyl-2-pentanone (MIBK) (64.57 g, 0.645 mol, obtained from the Sigma-Aldrich Company of St. Louis, Mo.), and 98% $H_2SO_4$ (3.6 µL, about 75 ppm based on total weight of reagents, obtained from Fisher Scientific of Waltham, Mass.). The Dean Stark trap was filled with MIBK and the flask placed under nitrogen. The flask was placed in an oil bath and heated sufficiently to allow the reaction mixture to reflux. The reaction was monitored by the amount of water collected in the Dean Stark trap given that water and MIBK form an azeotrope at 88° C. that subsequently separated into the two distinct layers. Water stopped collecting in the trap after approximately 21 hours of refluxing. The reaction was removed from the oil bath and was allowed to cool to ambient temperature.

Then 150 mesh activated, basic $Al_2O_3$ (about 9 g, or about 10 wt. % based on the total weight of reagents, obtained from the Sigma-Aldrich Company of St. Louis, Mo.) was added to the flask and stirred for approximately 1 hour. The $Al_2O_3$ was removed by vacuum filtration over a sintered glass funnel. The remaining MIBK along with the mono-ketal impurity were removed on a rotary evaporator using an oil bath set to 180° C. and reducing the pressure in the evaporator to about 6.5 Torr. Some solid particles were visible in the reaction mixture, so about 75 mL of hexane was added to the crude mixture and then the solid particles removed by vacuum filtration over a sintered glass funnel. The hexane was then removed using the rotary evaporator. The reaction product was observed to form a white, crystalline solid crystallized upon cooling. The yield of solid obtained based on the starting pentaerythritol was 61.5%. A sample was analyzed by $^1H$ NMR (300 MHz, $CDCl_3$ solvent) to confirm the identity of product as the bis-MIBK adduct of pentaerythritol.

Example 32

Transketalization of MIBK Trisketal of Sorbitol with Acetone

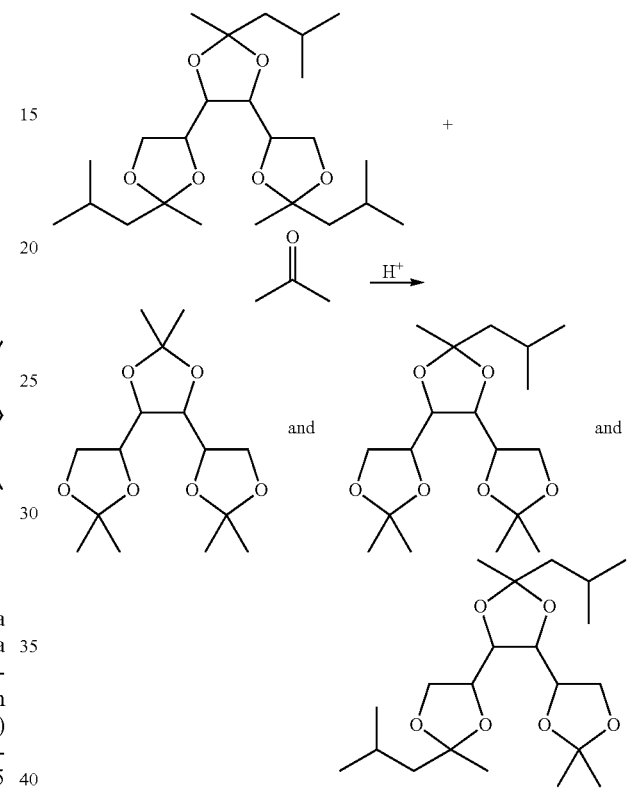

*only representative isomers shown

To a 20 mL scintillation vial equipped with a magnetic stir bar were added tris-MIBK ketal of sorbitol, synthesized according to the procedure of Example 6, (5.22 g, 12 mmol), acetone (4.26 g, 73 mmol, obtained from Fisher Scientific of Waltham, Mass.), and 98% $H_2SO_4$ (0.2 µL, about 40 ppm based on total weight of reagents, obtained from Fisher Scientific of Waltham, Mass.). The contents were stirred at room temperature and sampled periodically to measure the extent of transketalization using GC-MS. The GC-MS percentages of transketalized products are shown in Table 5.

TABLE 5

| | Percent by GC-MS of transketalization products. | | | |
|---|---|---|---|---|
| Time (hrs.) | tris-MIBK ketal (0 exchanges) | mono-acetonide (1 exchange) | bis-acetonide (2 exchanges) | tris-acetonide (3 exchanges) |
| 0 | 89.7% | Not Detected (ND) | ND | ND |
| 17 | 11.4% | 39.2% | 43.1% | 0.1% |
| 20.28 | 7.2% | 34.8% | 51.8% | 0.1% |
| 24.25 | 3.5% | 28.2% | 61.9% | 0.2% |
| 41.03 | 0.7% | 16.9% | 74.5% | 0.5% |
| 47.28 | 0.4% | 14.5% | 77.1% | 0.6% |

Example 33

Transketalization Between ST-MIBK and Ethyl Levulinate

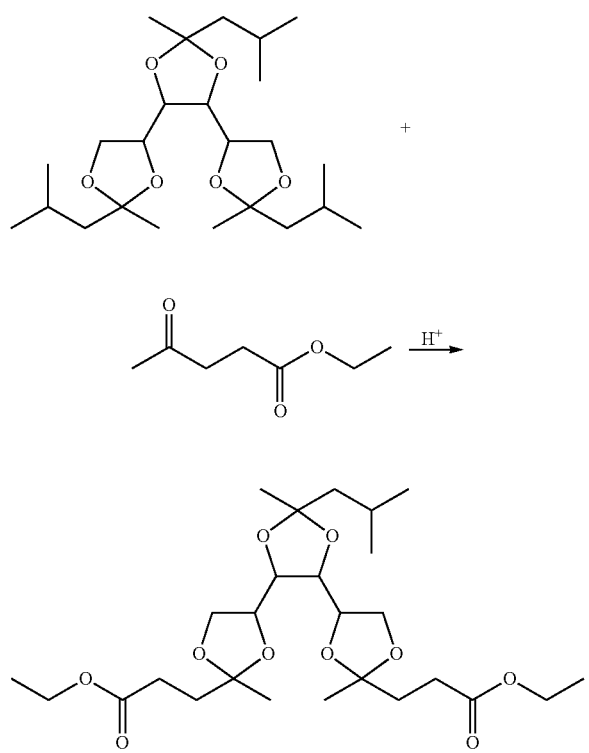

To a 1 L 3-neck round bottom flask equipped with a magnetic stir bar and a Dean Stark trap equipped with a condenser and a nitrogen inlet/outlet were added the tris-MIBK ketal of sorbitol synthesized according to the procedure of Example 6 (151.30 g, 0.35 mol), ethyl levulinate (207.74 g, 1.44 mol, obtained from the Langfang Triple Well Chemicals Company, Ltd. of Langfang City, HeBei, China), and 98% $H_2SO_4$ (14.6 μL, about 75 ppm based on total weight of reagents, obtained from Fisher Scientific of Waltham, Mass.). The flask was placed in an oil bath and the oil bath set to 90° C. The pressure inside the flask was reduced to about 35-50 Torr using a Teflon pump. These conditions were maintained for 11.5 hours. The flask was then backfilled with nitrogen and cooled to room temperature.

Then 150 mesh activated, basic $Al_2O_3$ (about 35 g, about 10 wt. %, obtained from the Sigma-Aldrich Company of St. Louis, Mo.) was added to the flask and stirred for approximately 1 hour. The $Al_2O_3$ was removed by vacuum filtration over a sintered glass funnel. MIBK and unreacted ethyl levulinate were distilled out of the mixture using a rotary evaporator using an oil bath set to about 60° C. and pressure of about 8 Torr. The oil bath temperature slowly ramped from 60° C. to 180° C. during rotation and collection of liquids. The undistilled liquid was then analyzed by GC-FID and found to contain about 2.5% tris-MIBK ketal of sorbitol, about 7.7% mono-levulinate bis-MIBK ketal of sorbitol, about 82.7% mono-MIBK bis-levulinate ketal of sorbitol, and about 6.1% tris-levulinate ketal of sorbitol.

Example 34

Transketalization of MEK Trisketal of Sorbitol with Ethyl Levulinate

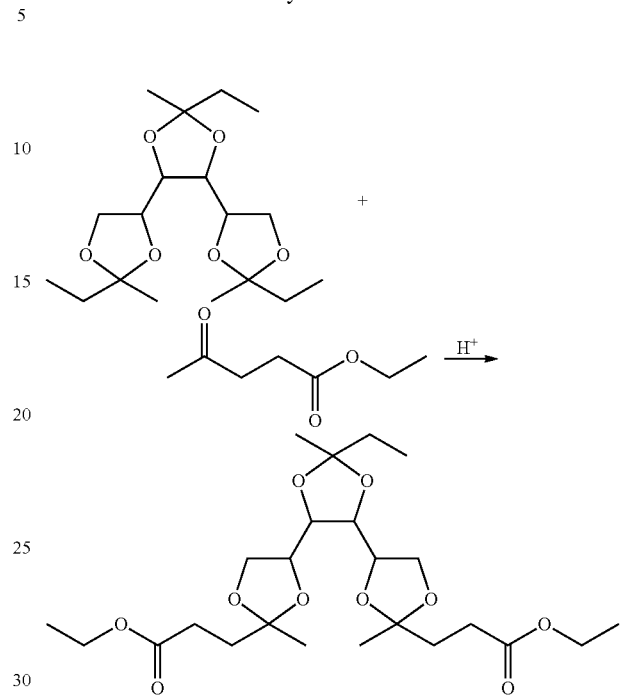

To a 250 mL 3-neck round bottom flask equipped with a magnetic stir bar and a Dean Stark trap topped with a condenser and a nitrogen inlet/outlet were added tris-MEK ketal of sorbitol synthesized according to the procedure of Example 5 (29.35 g, 85 mmol), ethyl levulinate (49.22 g, 341 mmol, obtained from the Langfang Triple Well Chemicals Company, Ltd. of Langfang City, HeBei, China), and 98% $H_2SO_4$ (3.2 μL, about 75 ppm based on total weight of reagents, obtained from Fisher Scientific of Waltham, Mass.). The flask was placed in an oil bath, and the bath temperature set to 70° C. The pressure in the flask was reduced to between 8-20 Torr. These conditions were maintained for about 25 hours at which point the flask was backfilled with nitrogen and the flask cooled to room temperature.

Then 150 mesh activated, basic $Al_2O_3$ (about 8 g, or 10 wt. % based on the total weight of reagents, obtained from the Sigma-Aldrich Company of St. Louis, Mo.) was added to the flask and stirred for approximately 1 hour. The $Al_2O_3$ was removed by vacuum filtration over a sintered glass funnel. The MIBK and unreacted ethyl levulinate were stripped using rotary evaporator, and the sample analyzed by GC-FID. The stripped reaction mixture was found to contain about 2.1% ethyl levulinate, about 0.7% of the tris-MEK ketal of sorbitol, about 15.2% bis-MEK, mono-levulinate ketal of sorbitol, about 78.6% mono-MEK, bis-levulinate ketal of sorbitol about 3.4% tris-levulinate ketal of sorbitol. The bis-levulinate ketal of sorbitol was separated using a Kugelrohr apparatus wherein the mixture was heated to 208° C. at a pressure of about 300 mTorr which was sufficient to remove the bis-MEK, mono-levulinate ketal of sorbitol. The undistilled liquid was analyzed and found to contain about 1.3% bis-MEK, mono-levulinate ketal of sorbitol, about 92.4% mono-MEK, bis-levulinate ketal of sorbitol, and about 6.3% tris-levulinate ketal of sorbitol.

Example 35

Transketalization of Trisacetonide Ketal of Sorbitol with Ethyl Pyruvate

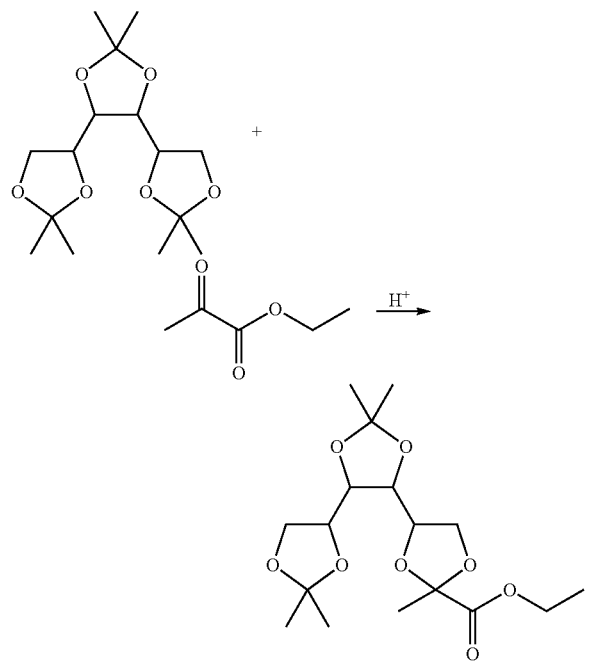

To a 100 mL 3-neck round bottom flask equipped with a magnetic stir bar and a dean stark trap topped with a condenser and a nitrogen inlet/outlet were added tris-acetonide of sorbitol, synthesized according to the procedure of Example 1 (12.54 g, 41.5 mmol), ethyl pyruvate (29.06 g, 250 mmol, obtained from the Sigma-Aldrich Company of St, Louis, Mo.), and 98% $H_2SO_4$ (1.70 μL, about 75 ppm based on total weight of reagents, obtained from Fisher Scientific of Waltham, Mass.). The flask was placed under nitrogen and immersed in an oil bath set to a temperature of about 100° C. and stirred for approximately 21 hours. The temperature was then decreased to 60° C. over the course of the next 2 hours. The pressure in the flask was then reduced to approximately 13 Torr and maintained for 1 hour. The flask was backfilled with nitrogen and cooled to room temperature.

The crude mixture was analyzed by GC-MS, which showed that approximately 20% of the tris-acetonide of sorbitol had undergone ketal exchange to give the bis-acetonide mono-pyruvate ketal of sorbitol.

Example 36

Transketalization of Acetone Trisketal of Sorbitol with Ethyl Acetoacetate Mono, Bis, and Tris Ketal Exchange Products

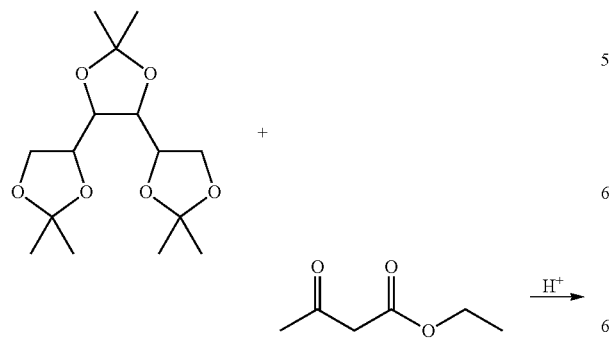

To a 100 mL 3-neck round bottom flask equipped with a magnetic stir bar and a Dean Stark trap topped with a condenser and a nitrogen inlet/outlet were added tris-acetonide of sorbitol, synthesized according to the procedure of Example 1 (5.51 g, 18 mmol), ethyl acetoacetate (14.23 g, 109 mmol, obtained from Acros Organics of Geel, Belgium), and 98% $H_2SO_4$ (0.8 μL, about 75 ppm based on total weight of reagents, obtained from Fisher Scientific of Waltham, Mass.). The flask was placed under nitrogen, immersed in an oil bath set to a temperature of 100° C., and stirred for approximately 5 hours. Then the flask was cooled to room temperature.

Then 150 mesh activated, basic $Al_2O_3$ (about 2 g, or 10 wt. % based on the total weight of all reagents, obtained from the Sigma-Aldrich Company of St. Louis, Mo.) was added to the flask and stirred for approximately 1 hour. The $Al_2O_3$ was removed by vacuum filtration over a sintered glass funnel. The crude mixture was placed on a rotary evaporator in order to remove the unreacted ethyl acetoacetate by reducing the pressure in the flask to about 8 Torr, and rotating the evaporation flask in an oil bath set to a temperature of about 60° C. The temperature of the oil bath was gradually ramped from 60° C.-115° C. and maintained at 115° C. for 10 minutes. The undistilled liquid was then analyzed by GC-FID and found to contain about 3.3% ethyl acetoacetate, about 2.6% tris-acetonide of sorbitol, about 28.0% bis-acetonide mono-acetoacetate ketal of sorbitol, about 59.4% mono-acetonide bis-acetoacetate ketal of sorbitol, and about 1.8% tris-acetoacetate ketal of sorbitol.

Example 37

Transketalization of MIBK Bisketal of Diglycerol with Ethyl Levulinate

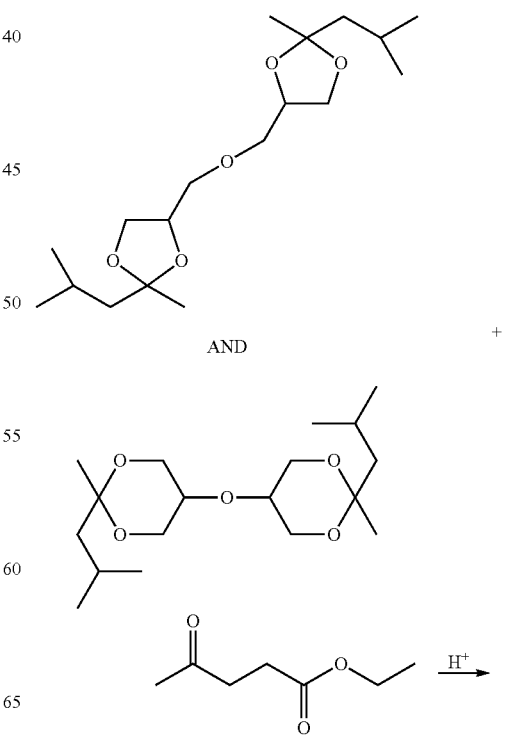

-continued

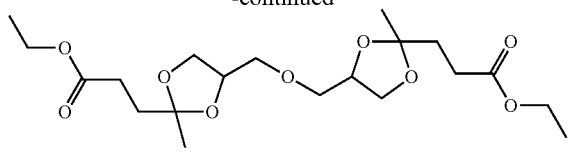

AND

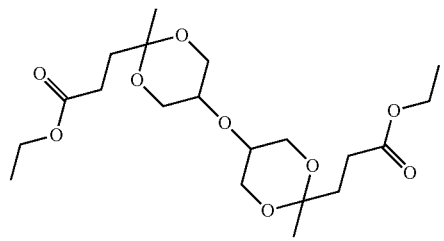

-continued

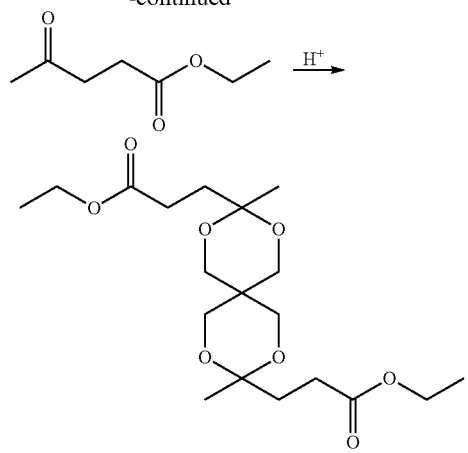

To a 100 mL 3-neck round bottom flask equipped with a magnetic stir bar and a Dean Stark trap topped with a condenser and a nitrogen inlet/outlet were added the bis-MIBK ketal of diglycerol, synthesized according to the procedure of Example 10 (13.25 g, 0.04 mol), ethyl levulinate (23.13 g, 0.16 mol, obtained from the Langfang Triple Well Chemicals Company, Ltd. of Langfang City, HeBei, China), and 98% $H_2SO_4$ (1.48 µL, about 75 ppm based on total weight of reagents, obtained from Fisher Scientific of Waltham, Mass.). The flask was immersed in an oil bath and the temperature of the bath set to about 70° C. The pressure in the flask was reduced to between 15 and 30 Torr using a Teflon pump. These conditions were maintained for about 15.5 hours. The flask was then backfilled with nitrogen and cooled to room temperature.

Then 150 mesh activated, basic $Al_2O_3$ (about 4 g, or 10 wt. % based on the total weight of reagents, obtained from the Sigma-Aldrich Company of St. Louis, Mo.) was added to the flask and stirred for approximately 1 hour. The $Al_2O_3$ was removed by vacuum filtration over a sintered glass funnel. The unreacted ethyl levulinate was stripped from the reaction mixture using a rotary evaporator. The undistilled liquid was found to contain about 98.2% of the bis-levulinate ketal of diglycerol by GC-FID and GC-MS (90% 5-membered ketal ring, 10% 6-membered ketal ring). The recovered product amounted to a 76% yield based on the starting bis-MIBK ketal of diglycerol. A sample was analyzed by $^1H$ NMR. (300 MHz, $CDCl_3$ solvent) to confirm the identity of product as the diglycerol bisketal of ethyl levulinate.

Example 38

Transketalization of MIBK Bisketal of Pentaerythritol with Ethyl Levulinate

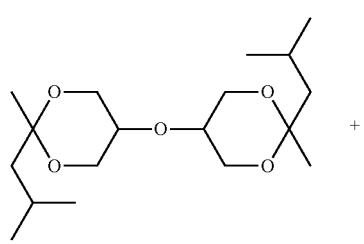 +

To a 100 mL 3-neck round bottom flask equipped with a magnetic stir bar and a Dean Stark trap topped with a condenser and a nitrogen inlet/outlet were added the bis-MIBK ketal of pentaerythritol, obtained using the process of Example 31 (11.17 g, 37 mmol), ethyl levulinate (18.90 g, 131 mmol, obtained from the Langfang Triple Well Chemicals Company, Ltd. of Langfang City, HeBei, China), and 98% $H_2SO_4$ (1.24 L, about 75 ppm based on total weight of reagents, obtained from Fisher Scientific of Waltham, Mass.). The flask was placed in an oil bath heated to 70° C. and the pressure in the flask was reduced to about 15-30 Torr, and the flask was stirred for about 16 hours. Then the flask backfilled with nitrogen and cooled to room temperature.

Then 150 mesh activated, basic $Al_2O_3$ (about 3 g, or 10 wt. % based on the total weight of reagents, obtained from the Sigma-Aldrich Company of St. Louis, Mo.) was added to the flask and stirred for approximately 1 hour. The $Al_2O_3$ was removed by vacuum filtration over a sintered glass funnel. The unreacted ethyl levulinate was distilled out of the mixture using a rotary evaporator. The undistilled liquid was analyzed by GC-FID and found to contain about 2.8% ethyl levulinate with the remainder being the bis-levulinate ketal of pentaerythritol. Based on the starting amount of bis-acetonide ketal of pentaerythritol, the amount of recovered product amounted to a 76.5% yield. A sample was analyzed by $^1H$ NMR (300 MHz, $CDCl_3$ solvent) to confirm the identity of product as the ethyl levulinate bisketal of pentaerythritol.

Example 39C

Direct Synthesis of Tris-Levulinate Ketal of Sorbitol

A 500 ml 3-neck round bottom flask was charged with 54.65 g (0.3 mol) D-sorbitol (obtained from Acros Organics of Geel, Belgium) and 346.01 g (2.4 mol) ethyl levulinate (obtained from the Sigma Aldrich Company of St. Louis, Mo.). The flask was equipped with a Dean Stark trap, mechanical stirrer, and thermocouple. The contents of the flask were heated to 105° C., at which point 16.0 µl of concentrated sulfuric acid (98%, obtained from the Sigma Aldrich Company) was added to the reaction flask via a metered microliter pipette. A vacuum was applied to the reaction flask, slowly bringing the pressure down to 40 torr. This pressure was maintained with stirring while liquid was observed to collect in the Dean Stark trap. About 4 hours after addition of sulfuric acid, liquid had stopped collecting in the Dean Stark trap and the vacuum was released and a small sample was removed from the reaction flask and analyzed by GC-MS. Aside from the excess ethyl levulinate, the only product observed in the flask was the ethyl levulinate trisketal of sorbitol ("Et-TLSK").

The combined contents of the reaction flask and other batches of Et-TLSK made using the same procedure, totaling about 900 g, were added to the addition flask of a short path wiped film evaporator equipped with carbon blades. A vacuum was applied to the apparatus until the pressure in the apparatus reached 100 millitorr. While under vacuum the entire apparatus was heated to 150° C. The wiped film column blades were rotated at 70% at the maximum rate available on the apparatus. The cold finger of the wiped film apparatus was adjusted to 0° C. using a refrigerated chiller. Upon reaching the target temperature the contents of the reaction flask were dripped into the wiped film column at a rate of 160 drops/minute. After 3 hours, 15 minutes the contents of the addition flask had been emptied into the column. The non-distilled residue that was captured was analyzed by GC-MS and $^1$H NMR. Et-TLSK purity by GC-MS was 99.90%; by $^1$H NMR it was 99.39%.

Examples 40C-45

Compounding of Ketal Compounds with PVC

Compounds of the invention were screened for their effect on glass transition temperature (Tg) of polyvinyl chloride (PVC), and their effects were compared to that of a comparative amount of dioctyl phthalate (DOP, obtained from the Sigma Aldrich Company of St. Louis, Mo.). The comparison was made by thermal compounding of each material with PVC (#2095, batch #1497388, used as provided from the Georgia Gulf Corporation of Atlanta, Ga.) as described herein.

First, a stabilized PVC mixture was formed by admixing 66.5 g of the polyvinyl chloride, 2.5 g of Vikoflex 7170 epoxidized soybean oil (from Arkema, Inc. of Philadelphia, Pa.) and 1.0 g Thermo-Chek SP175 thermal stabilizer (from Ferro Corp. of Cleveland, Ohio). Then 3.5 g of stabilized PVC mixture was admixed with the compound to be screened ("plasticizer") to form a PVC/plasticizer admixture in the desired ratio. For example, to form a PVC/plasticizer mixture with 30 wt % plasticizer, 1.5 g of the plasticizer was admixed with the 3.5 g of stabilized PVC mixture.

The screws of a HAAKE MiniLab II compounder (obtained from Thermo Scientific of Waltham, Mass.) were set to co-rotate at 150 rpm. The system was set under a continual nitrogen purge. Compounding temperature was set at 165° C. The PVC/plasticizer admixture was fed into the compounder using a manual feed (column and hand-held piston). Blending time was between 10-15 minutes, with about 10 minute runs being the most common. The result of blending was a compounded mixture.

The compounded mixture was emptied into a stainless steel window mold measuring 10.0 cm×10.0 cm×1 mm. After partially filling the mold with the compounded mixture, the mold was covered with Teflon coated aluminum foil (BYTAC®, obtained from Fisher Scientific of Waltham, Mass.). A second sheet of Teflon coated aluminum foil was placed under the mold. A 0.1524 cm thick steel plate was placed on top and a second plate placed beneath the Teflon covered aluminum foil, to form a compression molding "sandwich". The sandwich was placed in a Carver Model 4122 pneumatic heated platen press (obtained from Carver, Inc. of Wabash, Ind.). The press was brought into contact with the sandwich and then preheated to 165° C. for 5 minutes. The press was then closed and force was applied in sequential steps starting at 453.6 kg (1,000 lbs) then the force was released, 1134 kg (2500 lb) then released, 1814 kg (4,000 lb) then released, and 2268 kg (5,000 lb) and held for 1 minute. The mold was then removed from the press and placed in a water bath at ambient temperature for 5 minutes. The sample was removed from the water bath and a solid, flexible molded sheet comprising the compounded mixture was removed from the mold.

The glass transition temperature ($T_g$) for each extruded product was measured using DSC. The composition of the compounded mixtures and the resulting Tg measurements are shown in Table 6.

TABLE 6

PVC compounding with plasticizers, and resulting $T_g$ of the compounded mixtures.

| Example No. | Compounding Temp., ° C. | Polyketal, Example No. | Weight % polyketal in stabilized PVC | Tg, ° C. |
|---|---|---|---|---|
| 40C | 180 | None | N/A | 67.22 |
| 41C | 160 | N/A - DOP | 30 | −7 |
| 42 | 165 | MIBK trisketal, Ex. 5 | 33.3 | 66.5 |
| 43 | 165 | Bis-MIBK, mono-ethyl levulinate ketal, Ex. 11, 13$^{(2)}$ | 33.3 | 1.6 |
| 44 | 165 | Mono-MIBK, bis-ethyl levulinate ketal, Ex. 33 | 33.3 | −6.6 |
| 45 | 165 | Et-TLSK, Ex. 39C | 33.3 | 6.2 |

(1) DOP is dioctyl phthalate, obtained from the Sigma Aldrich Company of St. Louis, MO.
$^{(2)}$Synthesis of Ex. 11; purification of Ex. 13, wherein the fraction employed here is the fraction containing primarily the mono-ethyl levulinate, bis-acetonide ketal of sorbitol A number of embodiments of the disclosure have been described. Nevertheless, it will be understood that various modifications may be made without departing from the spirit and scope of the disclosure. The various embodiments described above are provided by way of illustration only and should not be construed to limit the claims attached hereto. The present invention may suitably comprise, consist of, or consist essentially of, any of the disclosed or recited elements. Thus, the invention illustratively disclosed herein can be suitably practiced in the absence of any element which is not specifically disclosed herein. Various modifications and changes will be recognized that may be made without following the example embodiments and applications illustrated and described herein, and without departing from the true spirit and scope of the following claims.

We claim:
1. A compound comprising structure I

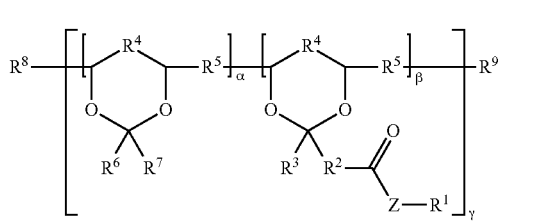

wherein
$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety, wherein $R^1$ is the same or different for each occurrence;

$R^2$ is a covalent bond or a linear or branched alkyl group wherein $R^2$ is the same or different for each occurrence;

$R^3$ is the same or different for each occurrence and is a linear, branched, or cyclic alkyl group, or at least one $R^3$ is

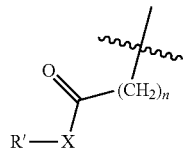

wherein
n is 0, 1, or 2,
R' is a linear or branched alkyl having between 1 and 6 carbon atoms, and
X is O or NR, wherein R is hydrogen or a linear or branched alkyl group having six or less carbon atoms;

$R^4$ is a covalent bond, methylene, or alkylmethylene, wherein a covalent bond indicates a 5-membered ring and a methylene or alkylmethylene indicates a 6-membered ring, wherein $R^4$ is the same or different for each occurrence;

$R^5$ is a covalent bond, methylene, ethylene, hydroxymethylene, $-CH_2-O-CH_2-$, or a polymeric moiety, wherein $R^5$ is the same or different for each occurrence;

$R^6$ and $R^7$ are independently linear, branched, or cyclic alkyl groups;

$R^8$ and $R^9$ are independently hydrogen, a linear, branched, or cyclic alkyl, a linear, branched, or cyclic alkenyl, alkynyl, aryl, alkaryl, or a polymeric moiety;

Z is O or NR, wherein R is hydrogen or a linear or branched alkyl group having six or less carbon atoms wherein Z is the same or different for each occurrence;

γ is an integer of at least 1; and
the structure I comprises at least one α unit and at least one β unit.

2. The compound of claim 1 wherein γ is 1, α is 1, and β is 1, $R^2$ is $-CH_2CH_2-$, $R^3$ is $CH_3-$, $R^8$ and $R^9$ are hydrogen, Z is O, and all $R^4$ and $R^5$ are covalent bonds.

3. The compound of claim 1 wherein $R^1$ is a cation or a linear or branched alkyl group having between 1 and 8 carbon atoms.

4. The compound of claim 1 wherein γ is 2, the sum of all α is 1, the sum of all β is 2, all $R^2$ are $-CH_2-$, all $R^3$ are $CH_3-$, $R^8$ and $R^9$ are hydrogen, all Z are O, and all $R^4$ and $R^5$ are covalent bonds.

5. The compound of claim 4 wherein $R^6$ and $R^7$ are independently methyl, ethyl, and isobutyl.

6. The compound of claim 4 wherein $R^1$ is sodium cation, ethyl, or n-butyl.

7. The compound of claim 1 wherein γ is 2, the sum of all α is 2, the sum of all β is 1, all $R^2$ are $-CH_2CH_2-$, all $R^3$ are $CH_3-$, $R^8$ and $R^9$ are hydrogen, all Z are O, and all $R^4$ and $R^5$ are covalent bonds.

* * * * *